(12) United States Patent
Srinimukesh et al.

(10) Patent No.: US 11,684,474 B2
(45) Date of Patent: Jun. 27, 2023

(54) DELIVERY SYSTEM FOR AIDED REPLACEMENT VALVE RECAPTURE AND REPOSITIONING POST-DEPLOYMENT

(71) Applicant: Edwards Lifesciences Corporation, Irvine, CA (US)

(72) Inventors: Harish Manickam Srinimukesh, Costa Mesa, CA (US); Travis Zenyo Oba, Yorba Linda, CA (US); David Robert Landon, Costa Mesa, CA (US); Glen T. Rabito, Lake Forest, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 442 days.

(21) Appl. No.: 16/934,879

(22) Filed: Jul. 21, 2020

(65) Prior Publication Data
US 2020/0345494 A1    Nov. 5, 2020

Related U.S. Application Data

(63) Continuation of application No. PCT/US2019/014999, filed on Jan. 24, 2019.

(60) Provisional application No. 62/622,036, filed on Jan. 25, 2018.

(51) Int. Cl.
*A61F 2/24* (2006.01)

(52) U.S. Cl.
CPC .......... *A61F 2/2439* (2013.01); *A61F 2/2436* (2013.01); *A61F 2220/0008* (2013.01); *A61F 2250/0098* (2013.01)

(58) Field of Classification Search
CPC ............ A61F 2/2439; A61F 2002/9511; A61F 2002/9534
See application file for complete search history.

(56) References Cited

U.S. PATENT DOCUMENTS

| | | |
|---|---|---|
| 3,657,744 A | 4/1972 | Ersek |
| 3,671,979 A | 6/1972 | Moulopoulos |
| 3,739,402 A | 6/1973 | Cooley et al. |

(Continued)

FOREIGN PATENT DOCUMENTS

| | | |
|---|---|---|
| CA | 2304325 A1 | 10/2000 |
| CA | 2827556 A1 | 7/2012 |

(Continued)

OTHER PUBLICATIONS

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. of 2014.

(Continued)

*Primary Examiner* — Shaun L David
(74) *Attorney, Agent, or Firm* — Knobbe Martens Olson & Bear LLP

(57) ABSTRACT

Disclosed herein are embodiments of a delivery system which can be used to recapture and/or reposition a replacement valve, such as a replacement mitral valve, after initial deployment of the valve. Embodiments of the disclosure can use the crimping/tensioning of sutures in order to re-crimp the replacement valve after release, though longitudinal or rotational forces.

15 Claims, 38 Drawing Sheets

(56) References Cited

U.S. PATENT DOCUMENTS

| | | |
|---|---|---|
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,994,077 A | 2/1991 | Dobben |
| 5,197,978 A | 3/1993 | Hess |
| 5,315,996 A | 5/1994 | Lundquist |
| 5,326,371 A | 7/1994 | Love et al. |
| 5,332,402 A | 7/1994 | Teitelbaum |
| 5,368,564 A | 11/1994 | Savage |
| 5,370,685 A | 12/1994 | Stevens |
| 5,397,355 A | 3/1995 | Marin et al. |
| 5,411,552 A | 5/1995 | Andersen et al. |
| 5,415,667 A | 5/1995 | Frater |
| 5,439,446 A | 8/1995 | Barry |
| 5,439,466 A | 8/1995 | Kilejian |
| 5,441,483 A | 8/1995 | Avitall |
| 5,474,563 A | 12/1995 | Myler et al. |
| 5,545,214 A | 8/1996 | Stevens |
| 5,554,185 A | 9/1996 | Block et al. |
| 5,573,520 A | 11/1996 | Schwartz et al. |
| 5,575,818 A | 11/1996 | Pinchuk |
| 5,607,444 A | 3/1997 | Lam |
| 5,669,919 A | 9/1997 | Sanders et al. |
| 5,693,061 A | 12/1997 | Pierce et al. |
| 5,697,382 A | 12/1997 | Love et al. |
| D390,957 S | 2/1998 | Fontaine |
| 5,725,519 A | 3/1998 | Penner et al. |
| 5,769,812 A | 6/1998 | Stevens et al. |
| 5,782,809 A | 7/1998 | Umeno et al. |
| 5,807,398 A | 9/1998 | Shaknovich |
| 5,810,873 A | 9/1998 | Morales |
| 5,840,081 A | 11/1998 | Andersen et al. |
| 5,855,601 A | 1/1999 | Bessler et al. |
| 5,868,777 A | 2/1999 | Lam |
| 5,868,782 A | 2/1999 | Frantzen |
| 5,879,381 A | 3/1999 | Moriuchi et al. |
| 5,902,334 A | 5/1999 | Dwyer et al. |
| 5,935,108 A | 8/1999 | Katoh et al. |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,086,612 A | 7/2000 | Jansen |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt et al. |
| 6,168,614 B1 | 1/2001 | Andersen et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,440,164 B1 | 8/2002 | DiMatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,527,800 B1 | 3/2003 | McGuckin, Jr. et al. |
| 6,540,778 B1 | 4/2003 | Quiachon et al. |
| 6,540,782 B1 | 4/2003 | Snyders |
| 6,582,462 B1 | 6/2003 | Andersen et al. |
| 6,602,281 B1 | 8/2003 | Klein |
| 6,610,088 B1 | 8/2003 | Gabbay |
| 6,623,518 B2 | 9/2003 | Thompson et al. |
| 6,629,534 B1 | 10/2003 | St. Goar et al. |
| 6,641,606 B2 | 11/2003 | Ouriel et al. |
| 6,652,578 B2 | 11/2003 | Bailey et al. |
| 6,664,058 B2 | 12/2003 | Kumar et al. |
| D484,979 S | 1/2004 | Fontaine |
| 6,676,698 B2 | 1/2004 | McGuckin, Jr. et al. |
| 6,682,537 B2 | 1/2004 | Ouriel et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,846,325 B2 | 1/2005 | Liddicoat |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 6,974,464 B2 | 12/2005 | Quijano et al. |
| 7,018,401 B1 | 3/2006 | Hyodoh et al. |
| 7,018,406 B2 | 3/2006 | Seguin et al. |
| 7,044,962 B2 | 5/2006 | Elliott |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,153,322 B2 | 12/2006 | Alt |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| D553,747 S | 10/2007 | Fliedner |
| 7,276,078 B2 | 10/2007 | Spenser et al. |
| 7,329,278 B2 | 2/2008 | Seguin et al. |
| 7,329,279 B2 | 2/2008 | Haug et al. |
| 7,331,992 B2 | 2/2008 | Randall et al. |
| 7,354,450 B2 | 4/2008 | Bicek et al. |
| 7,381,198 B2 | 6/2008 | Noriega et al. |
| 7,381,219 B2 | 6/2008 | Salahieh et al. |
| 7,393,360 B2 | 7/2008 | Spenser et al. |
| 7,402,168 B2 | 7/2008 | Sanderson et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,569,071 B2 | 8/2009 | Haverkost et al. |
| 7,585,321 B2 | 9/2009 | Cribier |
| 7,608,114 B2 | 10/2009 | Levine et al. |
| 7,615,072 B2 | 11/2009 | Rust et al. |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,632,298 B2 | 12/2009 | Hijlkema et al. |
| 7,637,902 B2 | 12/2009 | Eversull et al. |
| 7,658,759 B2 | 2/2010 | Case et al. |
| 7,708,775 B2 | 5/2010 | Rowe et al. |
| 7,748,389 B2 | 7/2010 | Salahieh et al. |
| 7,749,266 B2 | 7/2010 | Forster et al. |

(56) References Cited

U.S. PATENT DOCUMENTS

| | | |
|---|---|---|
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,785,360 B2 | 8/2010 | Freitag |
| 7,803,185 B2 | 9/2010 | Gabbay |
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| D635,261 S | 3/2011 | Rossi |
| D635,262 S | 3/2011 | Rossi |
| 7,914,466 B2 | 3/2011 | Davis et al. |
| 7,914,569 B2 | 3/2011 | Nguyen et al. |
| 7,918,819 B2 | 4/2011 | Karmarkar et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,988,724 B2 | 8/2011 | Salahieh et al. |
| 7,993,392 B2 | 8/2011 | Righini et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,057,538 B2 | 11/2011 | Bergin et al. |
| 8,070,799 B2 | 12/2011 | Righini et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,444 B2 | 1/2012 | Lentz et al. |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,926 B2 | 5/2012 | Hartley et al. |
| 8,167,932 B2 | 5/2012 | Bourang et al. |
| 8,167,934 B2 | 5/2012 | Styrc et al. |
| 8,177,799 B2 | 5/2012 | Orban, III |
| 8,182,528 B2 | 5/2012 | Salahieh et al. |
| 8,182,530 B2 | 5/2012 | Huber |
| 8,197,528 B2 | 6/2012 | Colgan et al. |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| 8,221,493 B2 | 7/2012 | Boyle et al. |
| 8,226,710 B2 | 7/2012 | Nguyen et al. |
| D665,079 S | 8/2012 | Zago |
| D665,080 S | 8/2012 | Zago |
| 8,236,045 B2 | 8/2012 | Benichou et al. |
| 8,241,350 B2 | 8/2012 | Randall et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,262,563 B2 | 9/2012 | Bakos et al. |
| 8,287,584 B2 | 10/2012 | Salahieh et al. |
| 8,303,653 B2 | 11/2012 | Bonhoeffer et al. |
| 8,308,798 B2 | 11/2012 | Pintor et al. |
| 8,313,525 B2 | 11/2012 | Tuval et al. |
| 8,317,854 B1 | 11/2012 | Ryan et al. |
| 8,323,241 B2 | 12/2012 | Salahieh et al. |
| 8,323,335 B2 | 12/2012 | Rowe et al. |
| 8,348,995 B2 | 1/2013 | Tuval et al. |
| 8,353,953 B2 | 1/2013 | Giannetti et al. |
| 8,361,137 B2 | 1/2013 | Perouse |
| 8,403,982 B2 | 3/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,425,593 B2 | 4/2013 | Braido et al. |
| 8,444,689 B2 | 5/2013 | Zhang |
| 8,449,599 B2 | 5/2013 | Chau et al. |
| 8,449,625 B2 | 5/2013 | Campbell et al. |
| 8,454,685 B2 | 6/2013 | Hariton et al. |
| 8,460,365 B2 | 6/2013 | Haverkost et al. |
| 8,460,368 B2 | 6/2013 | Taylor et al. |
| 8,465,541 B2 | 6/2013 | Dwork |
| 8,470,020 B2 | 6/2013 | Schaeffer et al. |
| 8,470,023 B2 | 6/2013 | Eidenschink et al. |
| 8,470,025 B2 | 6/2013 | Lenihan et al. |
| 8,470,028 B2 | 6/2013 | Thornton et al. |
| 8,475,521 B2 | 7/2013 | Suri et al. |
| 8,475,522 B2 | 7/2013 | Jimenez et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,785 B2 | 8/2013 | Gunderson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,535,368 B2 | 9/2013 | Headley, Jr. et al. |
| 8,562,663 B2 | 10/2013 | Mearns et al. |
| 8,568,472 B2 | 10/2013 | Marchand et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,579,966 B2 | 11/2013 | Seguin et al. |
| 8,584,849 B2 | 11/2013 | McCaffrey |
| 8,585,749 B2 | 11/2013 | Shelso |
| 8,585,755 B2 | 11/2013 | Chau et al. |
| 8,585,756 B2 | 11/2013 | Bonhoeffer et al. |
| 8,591,460 B2 | 11/2013 | Wilson et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,623,075 B2 | 1/2014 | Murray, III et al. |
| 8,640,521 B2 | 2/2014 | Righini et al. |
| 8,641,757 B2 | 2/2014 | Pintor et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,672,992 B2 | 3/2014 | Or |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,084 B2 | 4/2014 | Rolando et al. |
| 8,685,086 B2 | 4/2014 | Navia et al. |
| 8,707,957 B2 | 4/2014 | Callister et al. |
| 8,721,707 B2 | 5/2014 | Boucher et al. |
| 8,721,708 B2 | 5/2014 | Seguin et al. |
| 8,721,713 B2 | 5/2014 | Tower et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,753,384 B2 | 6/2014 | Leanna |
| 8,758,432 B2 | 6/2014 | Solem |
| 8,764,814 B2 | 7/2014 | Solem |
| 8,764,818 B2 | 7/2014 | Gregg |
| 8,771,338 B2 | 7/2014 | Schaeffer et al. |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,019 B2 | 7/2014 | Knippel et al. |
| 8,778,020 B2 | 7/2014 | Gregg et al. |
| 8,784,337 B2 | 7/2014 | Voeller et al. |

(56) References Cited

U.S. PATENT DOCUMENTS

| | | |
|---|---|---|
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,355 B2 * | 8/2014 | Alkhatib ............... A61F 2/2436 623/2.11 |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,814,931 B2 | 8/2014 | Wang et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,852,267 B2 | 10/2014 | Cattaneo |
| 8,858,620 B2 | 10/2014 | Salahieh et al. |
| 8,870,790 B2 | 10/2014 | Davis et al. |
| 8,870,947 B2 | 10/2014 | Shaw |
| 8,870,948 B1 | 10/2014 | Erzberger et al. |
| 8,870,950 B2 | 10/2014 | Hacohen |
| 8,876,883 B2 | 11/2014 | Rust |
| 8,876,892 B2 | 11/2014 | Tran et al. |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,894,703 B2 | 11/2014 | Salahieh et al. |
| 8,900,163 B2 | 12/2014 | Jacobsen et al. |
| 8,911,455 B2 | 12/2014 | Quadri et al. |
| 8,915,865 B2 | 12/2014 | Jacobsen et al. |
| 8,926,692 B2 | 1/2015 | Dwork |
| 8,926,693 B2 | 1/2015 | Duffy et al. |
| 8,926,694 B2 | 1/2015 | Costello |
| 8,939,960 B2 | 1/2015 | Rosenman et al. |
| 8,945,146 B2 | 2/2015 | Steingisser et al. |
| 8,945,209 B2 | 2/2015 | Bonyuet et al. |
| 8,951,243 B2 | 2/2015 | Crisostomo et al. |
| 8,951,299 B2 | 2/2015 | Paul et al. |
| 8,961,583 B2 | 2/2015 | Hojeibane et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,270 B2 | 4/2015 | Perkins et al. |
| 9,005,273 B2 | 4/2015 | Salahieh et al. |
| 9,005,278 B2 | 4/2015 | Pintor et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,029,418 B2 | 5/2015 | Dove et al. |
| 9,034,032 B2 | 5/2015 | McLean et al. |
| 9,034,033 B2 | 5/2015 | McLean et al. |
| 9,039,676 B2 | 5/2015 | Klima |
| 9,039,757 B2 | 5/2015 | McLean et al. |
| 9,055,937 B2 | 6/2015 | Rowe et al. |
| 9,061,119 B2 | 6/2015 | Le et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,084,694 B2 | 7/2015 | Goodin et al. |
| 9,125,738 B2 | 9/2015 | Figulla et al. |
| 9,138,312 B2 | 9/2015 | Tuval et al. |
| 9,155,619 B2 | 10/2015 | Liu et al. |
| 9,161,834 B2 | 10/2015 | Taylor et al. |
| 9,168,129 B2 | 10/2015 | Valdez et al. |
| 9,173,737 B2 | 11/2015 | Hill et al. |
| 9,173,738 B2 | 11/2015 | Murray, III et al. |
| 9,180,004 B2 | 11/2015 | Alkhatib |
| 9,186,249 B2 | 11/2015 | Rolando et al. |
| 9,192,469 B2 | 11/2015 | Mearns et al. |
| 9,216,056 B2 | 12/2015 | Datta et al. |
| 9,220,594 B2 | 12/2015 | Braido et al. |
| 9,241,790 B2 | 1/2016 | Lane et al. |
| 9,241,794 B2 | 1/2016 | Braido et al. |
| 9,248,014 B2 | 2/2016 | Lane et al. |
| 9,271,856 B2 | 3/2016 | Duffy et al. |
| 9,277,990 B2 | 3/2016 | Klima et al. |
| 9,277,993 B2 | 3/2016 | Gamarra et al. |
| 9,289,291 B2 | 3/2016 | Gorman, III et al. |
| 9,289,296 B2 | 3/2016 | Braido et al. |
| 9,295,551 B2 | 3/2016 | Straubinger et al. |
| 9,308,105 B2 | 4/2016 | Carlson et al. |
| 9,326,815 B2 | 5/2016 | Watson |
| 9,326,871 B2 | 5/2016 | Schaeffer et al. |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,364,321 B2 | 6/2016 | Alkhatib et al. |
| 9,370,423 B2 | 6/2016 | Ryan |
| 9,375,312 B2 | 6/2016 | Weber |
| 9,414,915 B2 | 8/2016 | Lombardi et al. |
| 9,445,897 B2 | 9/2016 | Bishop et al. |
| 9,456,877 B2 | 10/2016 | Weitzner et al. |
| 9,504,564 B2 | 11/2016 | Nguyen et al. |
| 9,532,870 B2 | 1/2017 | Cooper et al. |
| 9,572,662 B2 | 2/2017 | Morriss et al. |
| 9,579,193 B2 | 2/2017 | Rafiee |
| 9,579,196 B2 | 2/2017 | Morriss et al. |
| 9,585,751 B2 | 3/2017 | Morriss et al. |
| 9,592,120 B2 | 3/2017 | Tuval et al. |
| 9,597,181 B2 | 3/2017 | Christianson et al. |
| 9,597,182 B2 | 3/2017 | Straubinger et al. |
| 9,629,718 B2 | 4/2017 | Gloss et al. |
| 9,675,452 B2 | 6/2017 | Valdez et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,717,593 B2 | 8/2017 | Alkhatib et al. |
| 9,737,398 B2 | 8/2017 | Bruchman et al. |
| 9,737,400 B2 | 8/2017 | Fish et al. |
| 9,750,606 B2 | 9/2017 | Ganesan et al. |
| 9,763,780 B2 | 9/2017 | Morriss et al. |
| 9,770,329 B2 | 9/2017 | Lane et al. |
| 9,775,705 B2 | 10/2017 | Ottma et al. |
| 9,788,945 B2 | 10/2017 | Ottma et al. |
| 9,795,479 B2 | 10/2017 | Lim et al. |
| 9,833,313 B2 | 12/2017 | Board et al. |
| 9,833,315 B2 | 12/2017 | Vidlund et al. |
| 9,839,511 B2 | 12/2017 | Ma et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,695 B2 | 1/2018 | Stacchino et al. |
| 9,867,697 B2 | 1/2018 | Alkhatib et al. |
| 9,867,698 B2 | 1/2018 | Kovalsky et al. |
| 9,877,830 B2 | 1/2018 | Lim et al. |
| 9,889,002 B2 | 2/2018 | Bonhoeffer et al. |
| 9,889,029 B2 | 2/2018 | Li et al. |
| 9,895,225 B2 | 2/2018 | Rolando et al. |
| 9,901,443 B2 | 2/2018 | Morriss et al. |
| 9,907,681 B2 | 3/2018 | Tobis et al. |
| 9,913,714 B2 | 3/2018 | Tuval et al. |
| 9,925,045 B2 | 3/2018 | Creaven et al. |
| 9,931,232 B2 | 4/2018 | Gunderson et al. |
| 9,962,260 B2 | 5/2018 | Krans et al. |
| 9,974,651 B2 | 5/2018 | Hariton et al. |
| 9,987,463 B2 | 6/2018 | Guo et al. |
| 10,010,418 B2 | 7/2018 | Marchand et al. |
| 10,039,642 B2 | 8/2018 | Hillukka |
| 10,058,420 B2 | 8/2018 | Levi |
| 10,058,422 B2 | 8/2018 | Braido |
| 10,064,718 B2 | 9/2018 | Keidar |
| 10,070,954 B2 | 9/2018 | Braido et al. |
| 10,080,656 B2 | 9/2018 | Schweich, Jr. et al. |
| 10,092,400 B2 | 10/2018 | Jimenez et al. |
| 10,098,736 B2 | 10/2018 | Carmi et al. |
| 10,117,744 B2 | 11/2018 | Ratz et al. |
| 10,123,871 B2 | 11/2018 | Liu et al. |
| 10,130,467 B2 | 11/2018 | Braido et al. |

(56) References Cited

U.S. PATENT DOCUMENTS

| | | |
|---|---|---|
| 10,130,470 B2 | 11/2018 | Thomas et al. |
| 10,149,758 B2 | 12/2018 | Racchini et al. |
| 10,149,760 B2 | 12/2018 | Johnson et al. |
| 10,154,921 B2 | 12/2018 | Stante et al. |
| 10,172,732 B2 | 1/2019 | Murphy et al. |
| 10,179,044 B2 | 1/2019 | Ratz et al. |
| 10,188,536 B2 | 1/2019 | Lombardi et al. |
| 10,201,417 B2 | 2/2019 | Lin et al. |
| 10,213,301 B2 | 2/2019 | Ganesan et al. |
| 10,226,309 B2 | 3/2019 | Ho et al. |
| 10,231,827 B2 | 3/2019 | Mulvihill |
| 2001/0007956 A1 | 7/2001 | Letac et al. |
| 2001/0047200 A1 | 11/2001 | White et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0111619 A1 | 8/2002 | Keast et al. |
| 2003/0069522 A1 | 4/2003 | Jacobsen et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0243230 A1 | 12/2004 | Navia et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0159811 A1 | 7/2005 | Lane |
| 2005/0177131 A1 | 8/2005 | Lentz et al. |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020247 A1 | 1/2006 | Kagan et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0100687 A1 | 5/2006 | Fahey et al. |
| 2006/0100695 A1 | 5/2006 | Peacock et al. |
| 2006/0116625 A1 | 6/2006 | Renati et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241564 A1 | 10/2006 | Corcoran et al. |
| 2006/0241745 A1 | 10/2006 | Solem |
| 2006/0259135 A1 | 11/2006 | Navia et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0219620 A1 | 9/2007 | Eells et al. |
| 2007/0250151 A1 | 10/2007 | Pereira |
| 2007/0255394 A1 | 11/2007 | Ryan |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0082164 A1 | 4/2008 | Friedman |
| 2008/0082165 A1 | 4/2008 | Wilson et al. |
| 2008/0097571 A1 | 4/2008 | Denison et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177373 A1 | 7/2008 | Huang et al. |
| 2008/0177381 A1 | 7/2008 | Navia et al. |
| 2008/0183273 A1 | 7/2008 | Mesana et al. |
| 2008/0208307 A1 | 8/2008 | Ben-Muvhar et al. |
| 2008/0208327 A1 | 8/2008 | Rowe |
| 2008/0208328 A1 | 8/2008 | Antocci et al. |
| 2008/0234799 A1 | 9/2008 | Acosta et al. |
| 2008/0243233 A1 | 10/2008 | Ben-Muvhar et al. |
| 2008/0319526 A1 | 12/2008 | Hill et al. |
| 2009/0005863 A1 | 1/2009 | Goetz et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0118810 A1 | 5/2009 | Klein et al. |
| 2009/0125096 A1 | 5/2009 | Chu et al. |
| 2009/0138079 A1 | 5/2009 | Tuval et al. |
| 2009/0149946 A1 | 6/2009 | Dixon |
| 2009/0171438 A1 | 7/2009 | Chuter et al. |
| 2009/0171456 A1 | 7/2009 | Kveen et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2009/0312832 A1 | 12/2009 | Delap |
| 2010/0114299 A1 | 5/2010 | Ben Muvhar et al. |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0264198 A1 | 10/2011 | Murray, III et al. |
| 2011/0288626 A1 | 11/2011 | Straubinger et al. |
| 2011/0313515 A1 | 12/2011 | Quadri et al. |
| 2012/0022639 A1 | 1/2012 | Hacohen et al. |
| 2012/0035702 A1 | 2/2012 | Horvath et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0259405 A1 | 10/2012 | Weber et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0030520 A1 | 1/2013 | Lee et al. |
| 2013/0035759 A1 | 2/2013 | Gross et al. |
| 2013/0053950 A1 | 2/2013 | Rowe et al. |
| 2013/0116705 A1 | 5/2013 | Salahieh et al. |
| 2013/0131788 A1 | 5/2013 | Quadri et al. |
| 2013/0144375 A1 | 6/2013 | Giasolli et al. |
| 2013/0144378 A1 | 6/2013 | Quadri et al. |
| 2013/0172983 A1 | 7/2013 | Clerc et al. |
| 2013/0190861 A1 | 7/2013 | Chau et al. |

(56) References Cited

U.S. PATENT DOCUMENTS

| | | |
|---|---|---|
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0296718 A1 | 11/2013 | Ranganathan et al. |
| 2013/0310923 A1* | 11/2013 | Kheradvar ............ A61B 8/0841 623/2.11 |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0005764 A1 | 1/2014 | Schroeder |
| 2014/0018912 A1 | 1/2014 | Delaloye et al. |
| 2014/0025163 A1 | 1/2014 | Padala et al. |
| 2014/0046427 A1 | 2/2014 | Michalak |
| 2014/0052237 A1 | 2/2014 | Lane et al. |
| 2014/0052242 A1 | 2/2014 | Revuelta et al. |
| 2014/0058502 A1 | 2/2014 | Marchand et al. |
| 2014/0067037 A1* | 3/2014 | Fargahi ................ A61F 2/2439 623/1.12 |
| 2014/0067054 A1 | 3/2014 | Chau et al. |
| 2014/0088565 A1 | 3/2014 | Vongphakdy et al. |
| 2014/0088685 A1 | 3/2014 | Yevzlin et al. |
| 2014/0100651 A1 | 4/2014 | Kheradvar et al. |
| 2014/0100653 A1 | 4/2014 | Savage et al. |
| 2014/0128969 A1 | 5/2014 | Hill et al. |
| 2014/0155990 A1 | 6/2014 | Nyuli et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0215791 A1 | 8/2014 | Soundararajan et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0243957 A1 | 8/2014 | Wang et al. |
| 2014/0257467 A1 | 9/2014 | Lane et al. |
| 2014/0276395 A1 | 9/2014 | Wilson et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324162 A1 | 10/2014 | Knippel et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0331475 A1 | 11/2014 | Duffy et al. |
| 2014/0336754 A1 | 11/2014 | Gurskis et al. |
| 2014/0343669 A1 | 11/2014 | Lane et al. |
| 2014/0343670 A1* | 11/2014 | Bakis .................. A61F 2/2436 623/2.11 |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358221 A1 | 12/2014 | Ho et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0005873 A1 | 1/2015 | Chang et al. |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0099997 A1 | 4/2015 | Cabiri |
| 2015/0119974 A1 | 4/2015 | Rothstein |
| 2015/0127094 A1 | 5/2015 | Salahieh et al. |
| 2015/0142100 A1 | 5/2015 | Morriss et al. |
| 2015/0142103 A1 | 5/2015 | Vidlund |
| 2015/0148731 A1 | 5/2015 | McNamara et al. |
| 2015/0148815 A1 | 5/2015 | Steingisser et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0202044 A1 | 7/2015 | Chau et al. |
| 2015/0209141 A1 | 7/2015 | Braido et al. |
| 2015/0238315 A1 | 8/2015 | Rabito et al. |
| 2015/0238336 A1 | 8/2015 | Johnson et al. |
| 2015/0272737 A1 | 10/2015 | Dale et al. |
| 2015/0282964 A1 | 10/2015 | Beard et al. |
| 2015/0297346 A1 | 10/2015 | Duffy et al. |
| 2015/0328000 A1 | 11/2015 | Ratz et al. |
| 2015/0328001 A1 | 11/2015 | McLean et al. |
| 2015/0328002 A1 | 11/2015 | McLean et al. |
| 2015/0335424 A1 | 11/2015 | McLean et al. |
| 2015/0342736 A1 | 12/2015 | Rabito et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0100885 A1 | 4/2016 | Datta et al. |
| 2016/0113765 A1 | 4/2016 | Ganesan et al. |
| 2016/0113768 A1 | 4/2016 | Ganesan et al. |
| 2016/0135951 A1 | 5/2016 | Salahieh et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235525 A1 | 8/2016 | Rothstein et al. |
| 2016/0270935 A1 | 9/2016 | Rasmussen et al. |
| 2016/0278918 A1 | 9/2016 | Ibeling |
| 2016/0279386 A1 | 9/2016 | Dale et al. |
| 2016/0310267 A1 | 10/2016 | Zeng et al. |
| 2016/0317301 A1 | 11/2016 | Quadri et al. |
| 2016/0346513 A1 | 12/2016 | Swaney |
| 2017/0000603 A1 | 1/2017 | Conklin et al. |
| 2017/0000604 A1 | 1/2017 | Conklin et al. |
| 2017/0035568 A1 | 2/2017 | Lombardi et al. |
| 2017/0056171 A1 | 3/2017 | Cooper et al. |
| 2017/0079780 A1 | 3/2017 | Schweich, Jr. et al. |
| 2017/0128199 A1 | 5/2017 | Gurovich et al. |
| 2017/0128204 A1 | 5/2017 | Morriss et al. |
| 2017/0128209 A1 | 5/2017 | Morriss et al. |
| 2017/0156859 A1* | 6/2017 | Chang .................. A61F 2/2439 |
| 2017/0165064 A1 | 6/2017 | Nyuli et al. |
| 2017/0209266 A1 | 7/2017 | Lane et al. |
| 2017/0216023 A1 | 8/2017 | Lane et al. |
| 2017/0216026 A1 | 8/2017 | Quill et al. |
| 2017/0216029 A1* | 8/2017 | Crowley ............... A61F 2/2418 |
| 2017/0216575 A1 | 8/2017 | Asleson et al. |
| 2017/0252153 A1 | 9/2017 | Chau et al. |
| 2017/0258614 A1 | 9/2017 | Griffin |
| 2017/0273787 A1 | 9/2017 | Passman et al. |
| 2017/0319341 A1 | 11/2017 | Jimenez et al. |
| 2017/0325954 A1 | 11/2017 | Perszyk |
| 2017/0348096 A1 | 12/2017 | Anderson |
| 2018/0000582 A1 | 1/2018 | Tuval et al. |

(56) References Cited

U.S. PATENT DOCUMENTS

| | | | |
|---|---|---|---|
| 2018/0021129 A1 | 1/2018 | Peterson et al. | |
| 2018/0021132 A1 | 1/2018 | Ottma et al. | |
| 2018/0028177 A1 | 2/2018 | van Oepen et al. | |
| 2018/0049873 A1* | 2/2018 | Manash | A61M 25/0068 |
| 2018/0055629 A1 | 3/2018 | Oba et al. | |
| 2018/0055636 A1 | 3/2018 | Valencia et al. | |
| 2018/0085218 A1 | 3/2018 | Eidenschink | |
| 2018/0092744 A1 | 4/2018 | von Oepen et al. | |
| 2018/0104051 A1 | 4/2018 | Salahieh et al. | |
| 2018/0104052 A1 | 4/2018 | Salahieh et al. | |
| 2018/0104055 A1 | 4/2018 | Salahieh et al. | |
| 2018/0104056 A1 | 4/2018 | Salahieh et al. | |
| 2018/0110534 A1 | 4/2018 | Gavala et al. | |
| 2018/0110622 A1* | 4/2018 | Gregg | A61F 2/9517 |
| 2018/0116843 A1 | 5/2018 | Schreck et al. | |
| 2018/0125642 A1 | 5/2018 | White et al. | |
| 2018/0125646 A1 | 5/2018 | Bruchman et al. | |
| 2018/0125651 A1 | 5/2018 | Nasr | |
| 2018/0126127 A1 | 5/2018 | Devereux et al. | |
| 2018/0133006 A1 | 5/2018 | Jones et al. | |
| 2018/0185179 A1 | 7/2018 | Murphy et al. | |
| 2018/0193140 A1 | 7/2018 | Weber | |
| 2018/0206983 A1 | 7/2018 | Noe et al. | |
| 2018/0207010 A1* | 7/2018 | Kheradvar | A61F 2/95 |
| 2018/0235657 A1 | 8/2018 | Abunassar | |
| 2018/0235658 A1 | 8/2018 | Perszyk et al. | |
| 2018/0250126 A1 | 9/2018 | O'Connor et al. | |
| 2018/0250130 A1 | 9/2018 | Hariton et al. | |
| 2018/0256323 A1 | 9/2018 | Hariton et al. | |
| 2018/0271651 A1 | 9/2018 | Christianson et al. | |
| 2018/0271653 A1 | 9/2018 | Vidlund et al. | |
| 2018/0280171 A1* | 10/2018 | Gloss | A61F 2/95 |
| 2018/0296335 A1 | 10/2018 | Miyashiro | |
| 2018/0296336 A1 | 10/2018 | Cooper et al. | |
| 2018/0296378 A1* | 10/2018 | Aristizabal | A61F 2/966 |
| 2018/0296801 A1 | 10/2018 | Tegg et al. | |
| 2018/0303606 A1 | 10/2018 | Rothstein et al. | |
| 2018/0303609 A1 | 10/2018 | Kenny et al. | |
| 2018/0325668 A1 | 11/2018 | Morrissey et al. | |
| 2018/0333259 A1 | 11/2018 | Dibie | |
| 2018/0353292 A1 | 12/2018 | Keidar | |
| 2018/0360603 A1 | 12/2018 | Levi | |
| 2019/0008639 A1 | 1/2019 | Landon et al. | |
| 2019/0008640 A1 | 1/2019 | Cooper et al. | |
| 2019/0021850 A1 | 1/2019 | Nathe et al. | |
| 2019/0030285 A1 | 1/2019 | Prabhu et al. | |
| 2019/0038404 A1 | 2/2019 | Iamberger et al. | |
| 2019/0038405 A1 | 2/2019 | Iamberger et al. | |
| 2019/0069997 A1 | 3/2019 | Ratz et al. | |
| 2019/0070001 A1 | 3/2019 | Calomeni et al. | |
| 2019/0083243 A1 | 3/2019 | Hariton et al. | |
| 2019/0083244 A1 | 3/2019 | Hariton et al. | |
| 2019/0083245 A1 | 3/2019 | Hariton et al. | |
| 2019/0083246 A1 | 3/2019 | Hariton et al. | |
| 2019/0083247 A1 | 3/2019 | Hariton et al. | |
| 2019/0083248 A1 | 3/2019 | Hariton et al. | |
| 2019/0083249 A1 | 3/2019 | Hariton et al. | |
| 2019/0083250 A1 | 3/2019 | Hariton et al. | |
| 2019/0083251 A1 | 3/2019 | Hariton et al. | |
| 2019/0083252 A1 | 3/2019 | Hariton et al. | |
| 2019/0083253 A1 | 3/2019 | Hariton et al. | |
| 2019/0083254 A1 | 3/2019 | Hariton et al. | |
| 2019/0110893 A1 | 4/2019 | Haarer et al. | |
| 2019/0175338 A1 | 6/2019 | White et al. | |
| 2019/0175342 A1 | 6/2019 | Hariton et al. | |
| 2019/0192293 A1 | 6/2019 | Yu et al. | |
| 2019/0247188 A1* | 8/2019 | Wallace | A61B 17/08 |

FOREIGN PATENT DOCUMENTS

| | | |
|---|---|---|
| CN | 1745727 A | 3/2006 |
| DE | 102006052564 B3 | 12/2007 |
| DE | 202007018551 U1 | 12/2008 |
| EP | 0680351 A1 | 11/1995 |
| EP | 0778039 A1 | 6/1997 |
| EP | 0778040 A2 | 6/1997 |
| EP | 0657147 B1 | 8/1999 |
| EP | 0713408 B1 | 10/2001 |
| EP | 1259194 B1 | 2/2005 |
| EP | 1171059 B1 | 11/2005 |
| EP | 1478307 B1 | 11/2006 |
| EP | 1735038 A2 | 12/2006 |
| EP | 1255510 B1 | 4/2007 |
| EP | 1768732 A2 | 4/2007 |
| EP | 1768738 A2 | 4/2007 |
| EP | 1827558 A2 | 9/2007 |
| EP | 1239901 B1 | 10/2007 |
| EP | 1868530 A2 | 12/2007 |
| EP | 1895943 A1 | 3/2008 |
| EP | 1922038 A1 | 5/2008 |
| EP | 1945141 A2 | 7/2008 |
| EP | 1988851 A2 | 11/2008 |
| EP | 2007325 A2 | 12/2008 |
| EP | 2018204 A2 | 1/2009 |
| EP | 1472996 B1 | 9/2009 |
| EP | 2109416 A2 | 10/2009 |
| EP | 1709987 B1 | 12/2009 |
| EP | 1935377 B1 | 3/2010 |
| EP | 1469793 B1 | 6/2010 |
| EP | 1978895 B1 | 6/2010 |
| EP | 2250975 A1 | 11/2010 |
| EP | 0688576 B2 | 12/2010 |
| EP | 2308425 A1 | 4/2011 |
| EP | 1526887 B1 | 9/2011 |
| EP | 2370028 A2 | 10/2011 |
| EP | 2397108 A2 | 12/2011 |
| EP | 2398543 A1 | 12/2011 |
| EP | 1281375 B1 | 2/2012 |
| EP | 2421479 A2 | 2/2012 |
| EP | 2074964 B1 | 3/2012 |
| EP | 2218425 B1 | 5/2012 |
| EP | 2445568 A2 | 5/2012 |
| EP | 2453970 A2 | 5/2012 |
| EP | 2459266 A1 | 6/2012 |
| EP | 2496182 A1 | 9/2012 |
| EP | 2285317 B1 | 12/2012 |
| EP | 2566416 A1 | 3/2013 |
| EP | 2319458 B1 | 4/2013 |
| EP | 2605725 A2 | 6/2013 |
| EP | 2605729 A2 | 6/2013 |
| EP | 2608741 A2 | 7/2013 |
| EP | 2616004 A2 | 7/2013 |
| EP | 2616006 A2 | 7/2013 |
| EP | 2616007 A2 | 7/2013 |
| EP | 2629706 A1 | 8/2013 |
| EP | 2073756 B1 | 10/2013 |
| EP | 2670357 A1 | 12/2013 |
| EP | 2167179 B9 | 2/2014 |
| EP | 2699201 A1 | 2/2014 |
| EP | 1369098 B1 | 4/2014 |
| EP | 2739214 A2 | 6/2014 |
| EP | 2117469 B1 | 7/2014 |
| EP | 2124826 B1 | 7/2014 |
| EP | 2419050 B1 | 7/2014 |
| EP | 2750630 A1 | 7/2014 |
| EP | 2750631 A1 | 7/2014 |
| EP | 2771064 A1 | 9/2014 |
| EP | 2777616 A1 | 9/2014 |
| EP | 2777617 A1 | 9/2014 |
| EP | 1765445 B1 | 3/2015 |
| EP | 2870946 A1 | 5/2015 |
| EP | 2745805 B1 | 6/2015 |
| EP | 2749254 B1 | 6/2015 |
| EP | 2877132 A1 | 6/2015 |
| EP | 2898858 A1 | 7/2015 |
| EP | 2250976 B1 | 8/2015 |
| EP | 2590595 B1 | 8/2015 |
| EP | 2921139 A1 | 9/2015 |
| EP | 1734903 B1 | 10/2015 |
| EP | 2962664 A1 | 1/2016 |
| EP | 2967858 A2 | 1/2016 |
| EP | 2926766 B1 | 2/2016 |
| EP | 2985006 A1 | 2/2016 |
| EP | 2168536 B1 | 4/2016 |

(56) References Cited

FOREIGN PATENT DOCUMENTS

| | | |
|---|---|---|
| EP | 2238947 B2 | 4/2016 |
| EP | 2815725 B1 | 4/2016 |
| EP | 2237746 B1 | 5/2016 |
| EP | 2582326 B1 | 5/2016 |
| EP | 2453969 B1 | 6/2016 |
| EP | 2901966 B1 | 6/2016 |
| EP | 2815723 B1 | 7/2016 |
| EP | 2618779 B1 | 8/2016 |
| EP | 2853238 B1 | 8/2016 |
| EP | 3062745 A1 | 9/2016 |
| EP | 3069696 A1 | 9/2016 |
| EP | 3073965 A1 | 10/2016 |
| EP | 3075354 A2 | 10/2016 |
| EP | 3107497 A1 | 12/2016 |
| EP | 3107500 A1 | 12/2016 |
| EP | 3111888 A1 | 1/2017 |
| EP | 2967931 B1 | 2/2017 |
| EP | 2262451 B1 | 5/2017 |
| EP | 2538880 B1 | 5/2017 |
| EP | 2351541 B1 | 6/2017 |
| EP | 3184083 A1 | 6/2017 |
| EP | 2480167 B1 | 8/2017 |
| EP | 2865355 B1 | 9/2017 |
| EP | 3256073 A1 | 12/2017 |
| EP | 2446915 B1 | 1/2018 |
| EP | 3057541 B1 | 1/2018 |
| EP | 2934392 B1 | 2/2018 |
| EP | 3283011 A1 | 2/2018 |
| EP | 3037064 B1 | 3/2018 |
| EP | 3046511 B1 | 3/2018 |
| EP | 3142603 B1 | 3/2018 |
| EP | 3290004 A1 | 3/2018 |
| EP | 3294220 A1 | 3/2018 |
| EP | 3316822 A1 | 5/2018 |
| EP | 3316823 A1 | 5/2018 |
| EP | 2379322 B1 | 6/2018 |
| EP | 3335672 A2 | 6/2018 |
| EP | 3344190 A1 | 7/2018 |
| EP | 2967845 B1 | 8/2018 |
| EP | 3081195 B1 | 10/2018 |
| EP | 3426193 A1 | 1/2019 |
| EP | 2379009 B1 | 2/2019 |
| EP | 2793991 B1 | 2/2019 |
| EP | 3468480 A1 | 4/2019 |
| EP | 2663259 B1 | 5/2019 |
| EP | 3496664 A1 | 6/2019 |
| GB | 1264471 A | 2/1972 |
| GB | 1315844 A | 5/1973 |
| GB | 2245495 A | 1/1992 |
| GB | 2398245 A | 8/2004 |
| JP | 2002540889 A | 12/2002 |
| JP | 2008541865 A | 11/2008 |

OTHER PUBLICATIONS

Banai, Shmeul et al., The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Bavaria, Joseph E M.D.: "CardiAQ Valve Technologies: Transcatheter Mitral Valve Implantation," Sep. 21, 2009.

Bavaria, Joseph E. M.D et al.: "Transcatheter Mitral Valve Implantation: The Future Gold Standard for MR?," Applicant requests the Examiner to consider this reference to be prior art as of Dec. of 2010.

Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages, Applicant believes this may have been available online as early as Feb. 7, 2011.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first-in/382370.

Boudjemline, Younes, et al., "Steps Toward the Percutaneous Replacement of Atrioventricular Valves," JACC, vol. 46, No. 2, Jul. 19, 2005:360-5.

"CardiAQTM Valve Technologies reports Successful First-in-Human Trans-Apical implantation of its Second Generation Transcatheter Mitral Valve," CardiAQ Valve Technologies Press Release, May 20, 2014.

"Company Overview," at TVT on Jun. 25, 2009.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

CardiAQ Valve Technologies, "Innovations in Heart Valve Therapy," In3 San Francisco, Jun. 18, 2008, PowerPoint presentation in 19 slides.

Condado, Jose Antonio, et al., "Percutaneous Treatment of Heart Valves," Rev Esp Cardio. 2006;59(12):1225-31, Applicant believes this may have been available as early as Dec. of 2006.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Fanning, Jonathon P., et al., "Transcatheter Aortic Valve Implantation (TAVI): Valve Design And Evolution," International Journal of Cardiology 168 (2013) 1822-1831, Applicant believes this may have been available as eariy as Oct. 3, 2013.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitial-valve-replacement-devices-development>.

Feldman, Ted, MD. "Prospects for Percutaneous Valve Therapies," Circulation 2007; 116:2866-2877. Applicant believes that this may be available as early as Dec. 11, 2007.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Horvath et al.: "Transapical Aortic Valve Replacement under Real-time Magnetic Resonance Imaging Guidance: Experimental Results with Balloon- Expandable and Self-Expanding Stents," http://www.ncbi.nlm.nih.gov/pmc/articles/PMC3038190/. Jun. 2011.

Karimi, Houshang, et al., "Percutaneous Valve Therapies," SIS 2007 Yearbook, Chapter 11, pp. 1-11.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

(56) References Cited

OTHER PUBLICATIONS

Mack, Michael, M.D., "Antegrade Transcatheter Mitral valve Implantation: On-Going Experience in Swine Model," Applicant believes this may have been presented on Nov. of 2011 at TCT.
Mack, Michael, M.D., "Antegrade Transcatheter Mitral valve Implantation: A Short-term Experience in Swine Model," Applicant believes this may have been presented on May of 2011 at TVT.
Ma, Liang, et al., "Double-Crowned Valved Stents For Off-Pump Mitral Valve Replacement," European Journal of Cardio-thoracic Surgery 28 (2005) 194-199, Applicant believes this may have been available as early as Aug. of 2005.
Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
NJ350: Vote for Your Favorite New Jersey Innovations, Jun. 27, 2014, http://www.kilmerhouse.com/2014/06/nj350-vote-for-your-favorite-new-jersey-innovations/.
Neovasc corporate presentation, Oct. 2009, available at http://www.neovasc.com/investors/documents/Neovasc-Corporate-Presentation-October.2009.pdf.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Pluth, James R., M.D., et al., "Aortic and Mitral Valve Replacement with Cloth-Covered Braunwald-Cutter Prosthesis, A Three-Year Follow-up," The Annals Of Thoracic Surgery, vol. 20, No. 3, Sep. 1975, pp. 239-248.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. of 2008.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "LSI EMT Spotlight," May 15, 2009.
Ruiz, Carlos E., "Overview of Novel Transcatheter Valve Technologies," Applicant believes this may have been presented on May 27, 2010 at EuroPCR.
Raiz, J. Brent, "In3 Company Overview," Jun. 24, 2009.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Sondergaard, Lars, et al., "Transcatheter Mitral Valve Implantation: CardiAQ™," Applicant believes this may have been presented at TCT 2013.
Sondergaard, Lars, "CardiAQ TMVR FIH—Generation 2," Applicants believe this may have been presented in 2014 at the TVT symposium.
Sondergaard, Lars, et al., "Transcatheter Mitral Valve Implantation: CardiAQ™," Applicant believes this may have been presented at EuroPCR 2013.
Spillner, J. et al., "New Sutureless 'Atrial- Mitral-Valve Prosthesis' For Minimally Invasive Mitral Valve Therapy," Textile Research Journal, 2010, in 7 pages, Applicant believes this may have been available as early as Aug. 9, 2010.
Taramasso et al.: "New devices for TAVI: technologies and initial clinical experiences" http://www.nature.com/nrcardio/journal/v11/n3/full/nrcardio.2013.221..html?message-global=remove#access. Jan. 21, 2014.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
"Update," Applicant believes this may have been presented on Jun. 6, 2010 at TVT.
Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
Vu, Duc-Thang, et al., "Novel Sutureless Mitral Valve Implantation Method Involving A Bayonet Insertion And Release Mechanism: A Proof Of Concept Study In Pigs," The Journal of Thoracic and Cardiovascular Surgery, vol. 143, No. 4, 985-988, Apr. 2012, Applicant believes this may have been available online as early as Feb. 13, 2012.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
Webb, John G., et al., "Transcatheter Aortic Valve Implantation: The Evolution Of Prostheses, Delivery Systems And Approaches," Archives of Cardiovascular Disease (2012) 105, 153-159. Applicant believes this may have been available as early as Mar. 16, 2012.

* cited by examiner

DELIVERY SYSTEM FOR AIDED REPLACEMENT VALVE RECAPTURE AND REPOSITIONING POST-DEPLOYMENT

INCORPORATION BY REFERENCE TO ANY PRIORITY APPLICATIONS

This application is a continuation of International Application No. PCT/US2019/014999, filed Jan. 24, 2019, designating the United States and published in English by the International Bureau on Aug. 1, 2019 as WO 2019/147846, which claims priority to U.S. Provisional App. No. 62/622,036, filed Jan. 25, 2018, the entirety of each of which is hereby incorporated by reference in its entirety.

BACKGROUND

Field

Certain embodiments disclosed herein relate generally to prostheses for implantation within a lumen or body cavity and delivery systems for implanting a prosthesis. In particular, the prostheses and delivery systems relate in some embodiments to replacement heart valves, such as replacement mitral heart valves.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

In some embodiments, a delivery system and method are provided for delivering a replacement heart valve to a native mitral valve location. The delivery system and method may utilize a transseptal or transapical approach. In some embodiments, components of the delivery system facilitate bending of the delivery system to steer a prosthesis from the septum to a location within the native mitral valve. In some embodiments, a capsule is provided for containing the prosthesis for delivery to the native mitral valve location. In other embodiments, the delivery system and method may be adapted for delivery of implants to locations other than the native mitral valve.

The present disclosure includes, but is not limited to, the following embodiments.

Embodiment 1

A delivery system for a replacement valve. The delivery system can comprise a tether configured to releasably hold a replacement valve, a torqueing manifold configured to retain a first end of the tether, and an engagement pin configured to move from a locked position to an unlocked position, the engagement pin configured to releasably retain a second end of the tether, wherein longitudinal translation of the engagement pin from the locked position to the unlocked position releases the second end of the tether and the replacement valve from the delivery system, and wherein rotational movement of the torqueing manifold with respect to the engagement pin is configured to crimp or uncrimp a portion of the replacement valve.

Embodiment 2

The delivery system of Embodiment 1, further comprising a manifold shaft having the torqueing manifold on a distal end of the manifold shaft, the torqueing manifold having at least one protrusion extending distally from a distal end of the torqueing manifold, a bearing rotatably retained within the torqueing manifold, and a pin lock shaft having a release plate located proximal of the bearing and located on a distal end of the pin lock shaft, wherein the pin lock shaft is configured to engage the engagement pin in the locked position and the unlocked position.

Embodiment 3

The delivery system of Embodiment 2, wherein circumferential rotation of the manifold shaft with respect to the pin lock shaft is configured to crimp or uncrimp the portion of the replacement valve.

Embodiment 4

The delivery system of any one of Embodiments 2-3, wherein the engagement pin extends between the release plate and the bearing in the locked position, and wherein the second end of the tether is retained on the engagement pin between the release plate and the bearing in the locked position.

Embodiment 5

The delivery system of any one of Embodiments 2-4, wherein the manifold shaft is located within a lumen of the pin lock shaft, wherein the pin lock shaft is configured to longitudinally and rotationally translate with respect to the manifold shaft, and wherein proximal translation of the pin lock shaft releases the engagement pin from the bearing which releases the second end of the tether from the engagement pin Embodiment 6

The delivery system of any one of Embodiments 2-5, wherein the torqueing manifold comprises a plurality of distally extending protrusions extending around an outer circumference of the distal end of the torqueing manifold.

Embodiment 7

The delivery system of any one of Embodiments 1-6, wherein the engagement pin is generally L-shaped.

Embodiment 8

The delivery system of any one of Embodiments 1-7, further comprising the replacement valve, wherein the replacement valve is a replacement mitral valve.

Embodiment 9

The delivery system of any one of Embodiments 1-8, wherein the tether is configured to pass through an eyelet of the replacement valve.

Embodiment 10

A method of releasing a replacement valve from a delivery system, the method comprising expanding the replacement valve from a compressed configuration to an expanded configuration, the replacement valve having a distal end and a proximal end, the replacement valve releasably attached to the delivery system at a location distal to the replacement valve through at least one tether, and rotating a manifold shaft located radially inwards of the replacement valve in a first direction with respect to a locking shaft, wherein the manifold shaft has a manifold on a distal end located distal to the replacement valve, wherein the at least one tether is connected to the manifold and the locking shaft, and wherein the manifold shaft is located within a lumen of the locking shaft, wherein the rotating the manifold shaft in the first direction loosens the at least one tether to uncrimp the distal end of the replacement valve.

Embodiment 11

The method of Embodiment 10, wherein the expanding the replacement valve comprises proximally translating an outer sheath to uncover the proximal end of the replacement valve, and distally translating a nosecone to uncover the distal end of the replacement valve.

Embodiment 12

The method of Embodiment 10 or Embodiment 11, further comprising rotating the manifold shaft in a second direction opposite the first direction with respect to the locking shaft to crimp the distal end of the replacement valve.

Embodiment 13

The method of Embodiment 12, further comprising proximally translating a nosecone to cover the distal end of the replacement valve when the replacement valve is crimped.

Embodiment 14

The method of any one of Embodiments 10-13, further comprising proximally translating the locking shaft with respect to the manifold shaft to release at least one end of the at least one tether from the delivery system, wherein the release of the at least one end releases the replacement valve from the delivery system.

Embodiment 15

The method of any one of Embodiments 10-14, wherein the replacement valve is releasably attached to the delivery system via a plurality of tethers.

Embodiment 16

A crimping ring for a replacement valve, the crimping ring comprising a generally circular body having an inner lumen extending longitudinally therethrough and a plurality of longitudinally extending apertures on an outer circumference of the body, and a plurality of sutures, each of the sutures extending through one of the plurality of apertures and configured to extend proximally from a replacement valve, wherein applying a proximally directed force on one of the plurality of sutures is configured to cause an angular change in the position of the body and the replacement valve, and wherein applying a proximally directed force on all of the plurality of sutures generally at the same time provides proximal longitudinal translation of the body which is configured to at least partially compress a distal end of the replacement valve.

Embodiment 17

The crimping ring of Embodiment 16, wherein the replacement valve crimp and tilt ring comprises three sutures and wherein the body has three apertures spaced generally evenly around the outer circumference.

Embodiment 18

The crimping ring of any one of Embodiments 16-17, wherein each of the plurality of sutures is wrapped around the body and passes through one of the plurality of apertures.

Embodiment 19

The crimping ring of any one of Embodiments 16-18 further comprising the replacement valve attached to a delivery system via a second plurality of sutures extending through the inner lumen of the body, wherein the replacement valve is a replacement mitral valve.

Embodiment 20

The crimping ring of Embodiment 19, wherein the proximal longitudinal translation of the replacement valve crimp and tilt ring radially compresses the second plurality of sutures and the distal end of the replacement mitral valve prosthesis as the second plurality of sutures and the replacement mitral valve prosthesis pass through the inner lumen.

Embodiment 21

A delivery system for releasing a replacement valve. The delivery system can comprise a torqueing manifold. The torqueing manifold can have a protrusion. The protrusion can extend distally from a distal end. The torqueing manifold can be located on a distal end of a manifold shaft. The delivery system can further comprise a bearing. The bearing can be rotatably retained within the torqueing manifold. The delivery system can further comprise a release plate. The release plate can be located proximal of the bearing. The release plate can be located on a distal end of a pin lock shaft. The delivery system can further comprise an engagement pin. The engagement pin can extend between the release plate and the bearing. The delivery system can further comprise a suture. A first end the suture can be connected to the protrusion. A second end of the suture can be connected to the engagement pin between the release plate and the bearing. The suture can be configured to pass through an engagement aperture in a replacement valve. The manifold shaft can be located within a lumen of the pin lock shaft. The pin lock shaft can be configured to longitudinally translate with respect to the manifold shaft. Proximal translation of the pin lock shaft can release the engagement pin from the bearing and can release the second end of the suture from the engagement pin. Circumferential rotation of the manifold shaft with respect to the pin lock shaft can be configured to crimp or uncrimp the replacement valve.

Embodiment 22

A delivery system for a replacement valve. The delivery system can comprise a suture. The suture can be configured to pass through an eyelet of a replacement valve. The delivery system can comprise an inner member. The inner member can be configured to retain the first end of the suture. The delivery system can comprise an engagement pin. The engagement pin can be configured to move from a locked position to an unlocked position. The engagement pin can be configured to retain a second end of the suture. Longitudinal translation of the engagement pin from the locked position to the unlocked position can release the second end of the suture and the replacement valve from the delivery system. Rotational movement of the inner member with respect to the engagement pin is configured to crimp or uncrimp a portion of the replacement valve.

Embodiment 23

A method of releasing and recapturing a replacement valve from a delivery system. The method can comprise proximally translating an outer sheath to uncover a proximal end of a replacement valve. The method can comprise distally translating a nosecone to uncover a distal end of the replacement valve. The method can comprise rotating a manifold shaft in a first direction to uncrimp the distal end of the replacement valve. The method can comprise rotating the manifold shaft in a second direction to crimp the distal end of the replacement valve. The method can comprise proximally translating the nosecone to cover the distal end of the replacement valve.

Embodiment 24

A replacement valve crimp and tilt ring. The ring can comprise a body having an inner lumen extending longitudinally. The body can have a plurality of apertures on an outer circumference of the body extending longitudinally. The inner lumen can be configured to receive an end of a replacement valve. The ring can comprise a plurality of sutures. Each of the sutures can be connected to one of the plurality of apertures and can extend proximally. Applying a proximally directed force on one of the plurality of sutures causes an angular change in the position of the circular body and the replacement valve. Applying a proximally directed force on all of the plurality of sutures at the same time provides proximal longitudinal translation of the body to at least partially compress the end of the replacement valve.

DETAILED DESCRIPTION

The present specification and drawings provide aspects and features of the disclosure in the context of several embodiments of replacement heart valves, delivery systems, and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery system, etc. should not be taken as limiting, and features of any one embodiment discussed herein can be combined with features of other embodiments as desired and when appropriate. While certain of the embodiments described herein are described in connection with a transapical delivery approach, it should be understood that these embodiments can be used for other delivery approaches such as, for example, transseptal approaches. Moreover, it should be understood that certain of the features described in connection with some embodiments can be incorporated with other embodiments, including those which are described in connection with different delivery approaches.

Transapical Delivery System

Figure 1:
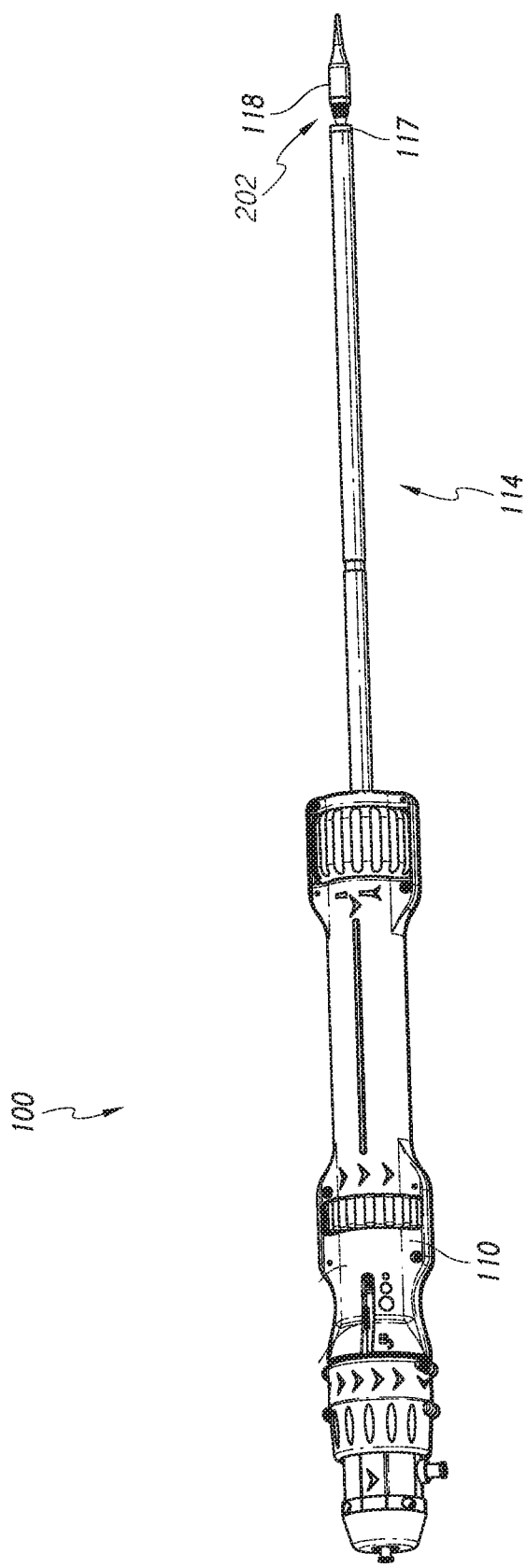
FIG. 1 illustrates an embodiment of a delivery system for a valve.

FIG. 1 illustrates an embodiment of a delivery device or system 100. The delivery system 100 can be used to deploy a prosthesis/implant, such as a replacement heart valve as described elsewhere in this specification, within the body. The delivery system 100 can receive and/or cover portions of the prosthesis such as a first end and second end of the implant.

Figure 2:
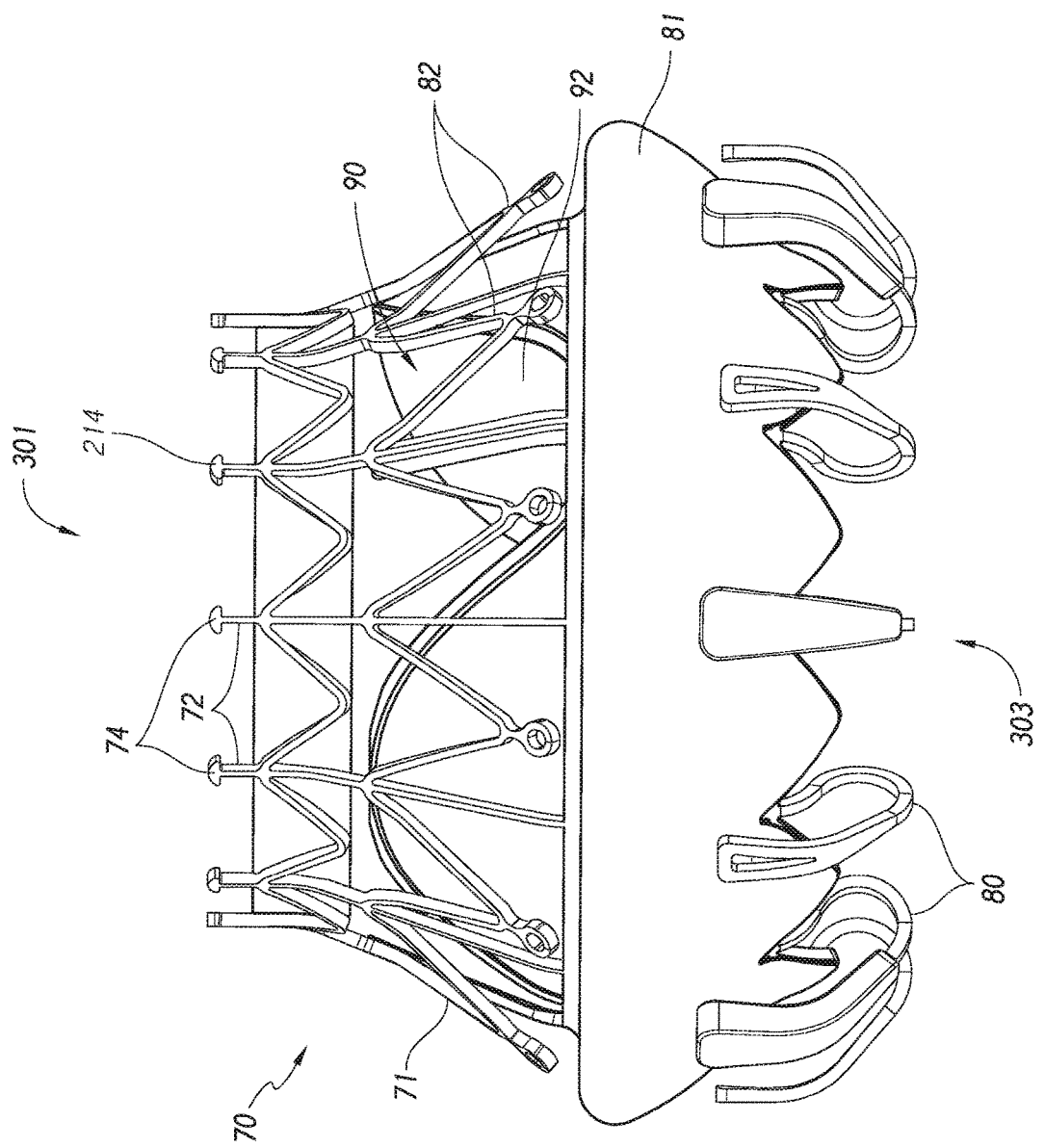
FIGS. 2-6 show a side views of embodiments of a valve prostheses that may be delivered using the delivery systems described herein.

The delivery system 100 can be used to deploy a prosthesis, such as a replacement heart valves as described elsewhere in this specification, within the body. The delivery system 10 can receive and/or cover portions of the prosthesis such as a first end 301 and second end 303 of the prosthesis (or implant) 70 illustrated in FIG. 2 below. For example, the delivery system 100 may be used to deliver an expandable implant or prosthesis 70, where the prosthesis 70 includes the first end 301 (or atrial end) and the second end 303 (or ventricular end), and wherein the second 303 end is configured to be deployed or expanded before the first end 301. In some embodiments, the tabs 74 of the prosthesis 70 shown in FIG. 2 may include eyelets (or apertures) 214 for attaching tethers as discussed below.

Figure 3:
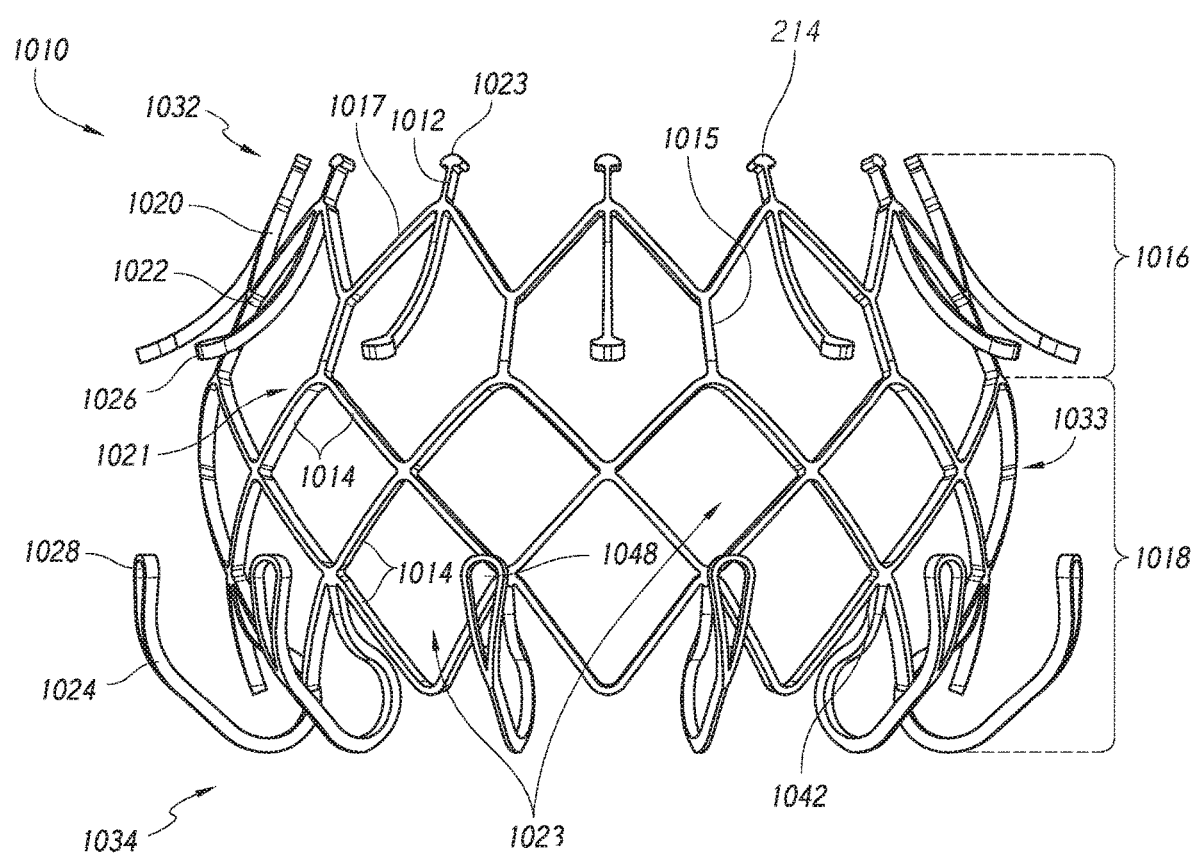

FIG. 3 illustrates an alternate embodiment of a valve prosthesis 1010 which can be used in conjunction with the delivery systems disclosed herein. The illustrated prosthesis 1010 includes a frame 1020 that may be self-expanding or balloon expandable. The prosthesis 1010 may be a replacement valve that can be designed to replace a damaged or diseased native heart valve such as a mitral valve, as discussed above. The additional features of the replacement valve are not shown in FIG. 3 in order to more clearly illustrate features of the frame 1020. It will also be understood that the prosthesis 1010 is not limited to being a replacement valve. In addition, it will be understood in FIG. 3, that only a front portion of the frame 1020 is shown for further ease of illustration. In some embodiments, the tabs 1023 may include eyelets 214 for attaching tethers as discussed below.

Figure 4:
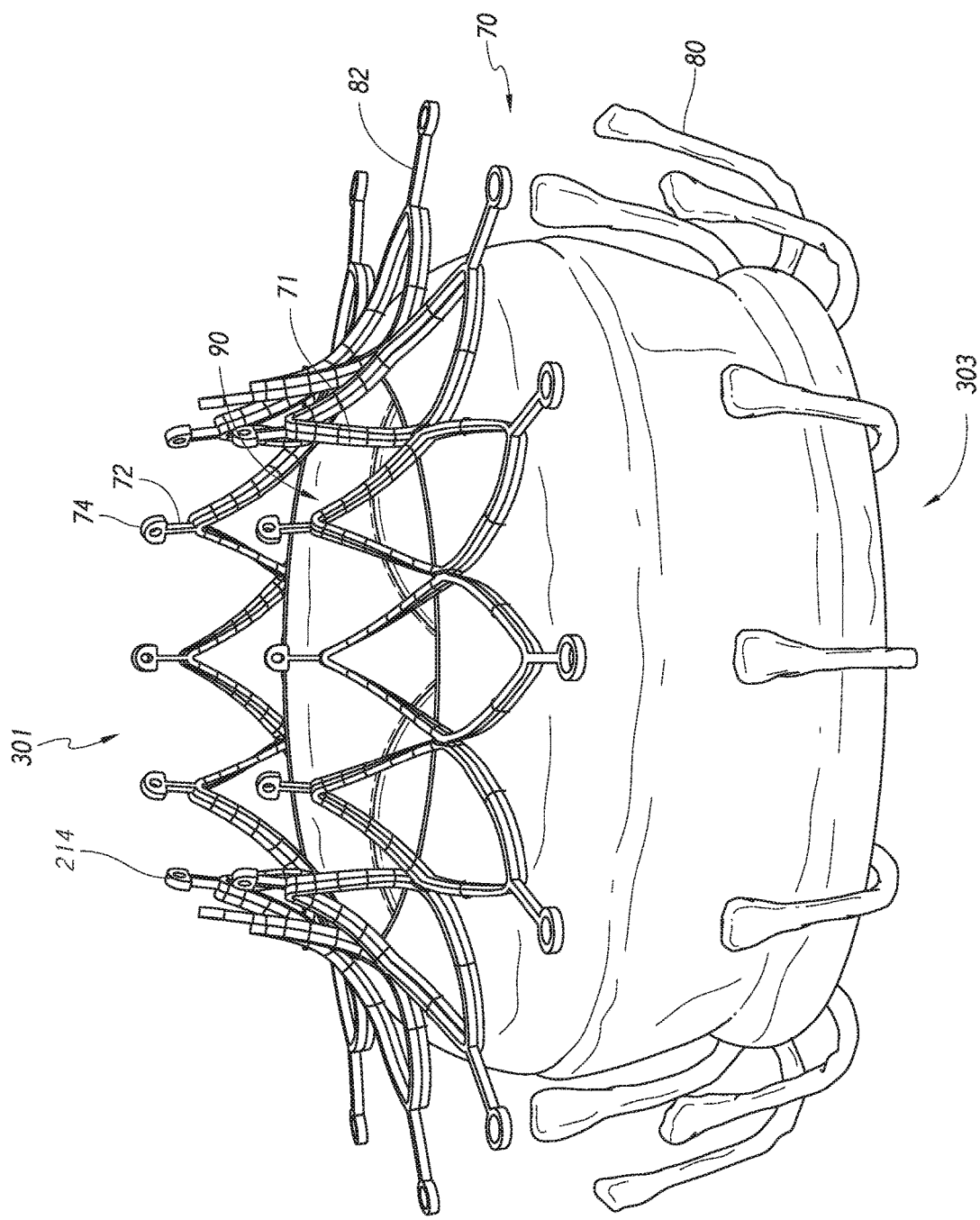
Figure 5:
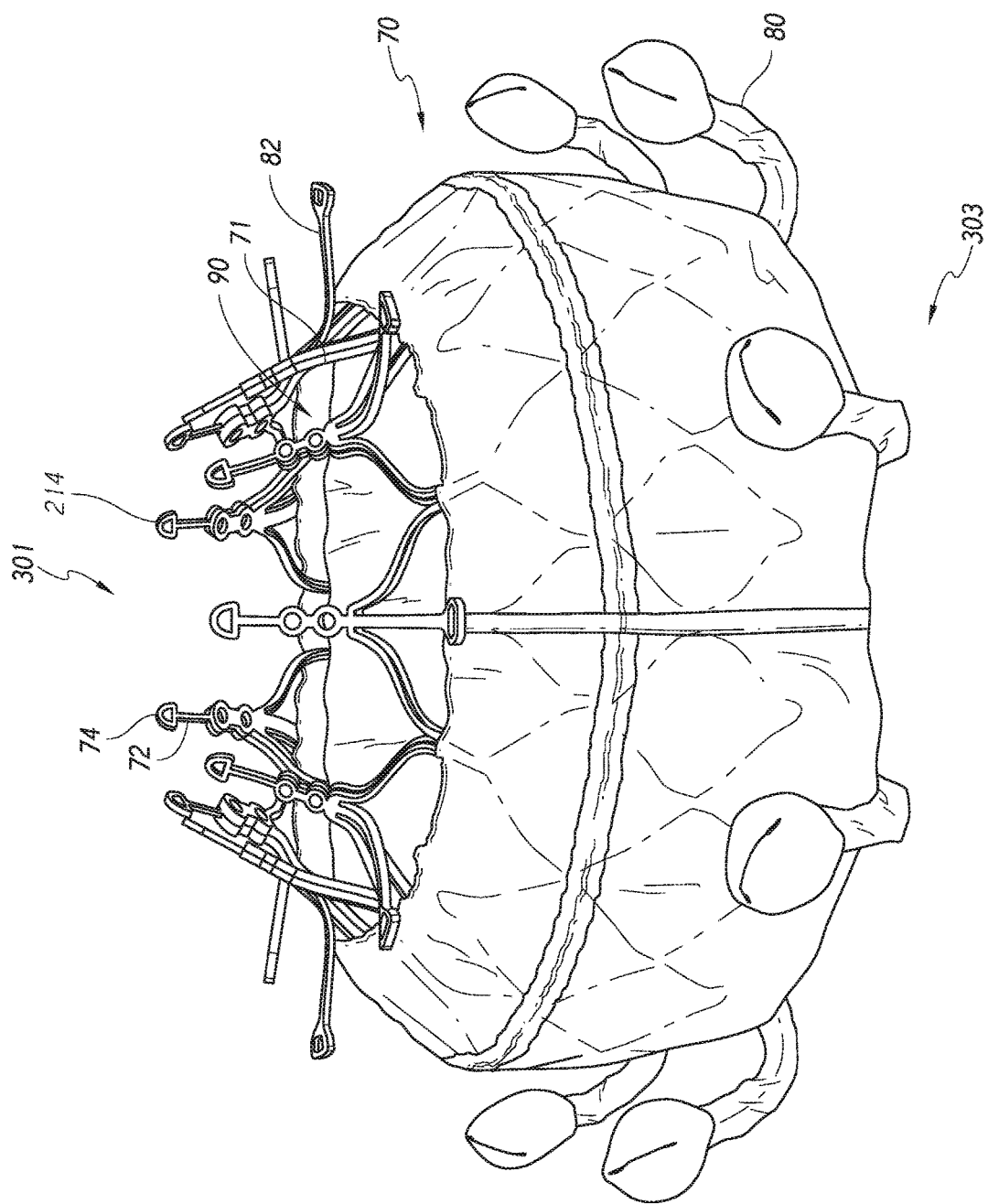
Figure 6:
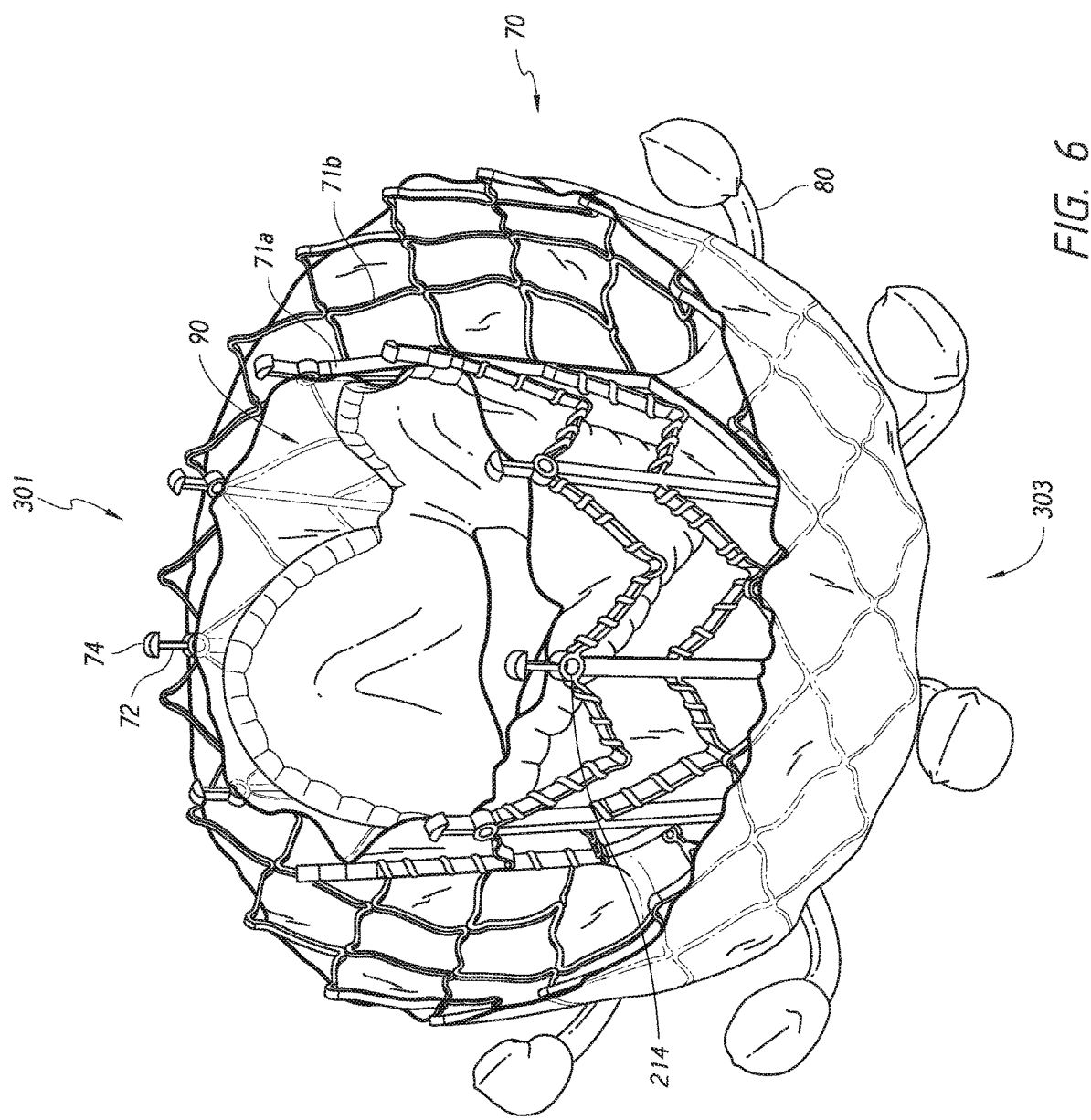

FIGS. 4-6 illustrate alternative embodiment of a prosthesis 70 that can used with the disclosed delivery system 100 and methodology discussed herein. These embodiments can have similar or the same features to the prostheses discussed herein. In some embodiments, the prosthesis may be a single frame prosthesis. In some embodiments, the prosthesis may be a dual frame prosthesis. For example, as shown in FIG. 6, a prosthesis 70 can include an inner frame 71a and an outer frame 71b. In some embodiments, the outer frame 71b can be conformable for placement in the native mitral valve annulus and the inner frame 71a can support the valve assembly 90. As shown, the prostheses 70 of FIGS. 4-6 can contain eyelets (or apertures) 214 for receiving the tethers discussed below. Further details on these specific embodiments can be found in U.S. Patent Publication Nos. 2018/0021129 and 2018/0055629, which have been incorporated by reference in their entirety.

Additional details and example designs for a prosthesis are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, and 2016/0317301 the entirety of these patents and publications are hereby incorporated by reference and made a part of this specification. Further details and embodiments of a replacement heart valve or prosthesis and its method of implantation are described in U.S. Patent Publication No. 2015/0328000, the entirety of which is hereby incorporated by reference and made a part of this specification.

Replacement heart valves can be delivered to a patient's heart mitral valve annulus or other heart valve location in various ways, such as by open surgery, minimally-invasive surgery, and percutaneous or transcatheter delivery through the patient's vasculature. The delivery system 100 illustrated in FIG. 1 can be relatively short to more easily be used in an open heart procedure or other more direct procedures than the percutaneous procedure starting at the leg. At the same time, the delivery system 100 can still be relatively flexible to allow, for example, advancement through the pulmonary veins or the wall of the left atrium and then bending of the delivery device for proper placement at the mitral valve. In some embodiments, the delivery system 100 is particularly suitable for delivering a replacement heart valve to a mitral valve location through a transapical approach (e.g., through the apex of the heart).

With reference first to the embodiment illustrated in FIG. 1, the delivery system 100 can include a handle 110 and a plurality of sheaths and/or shafts such as the illustrated outer elongate hollow member shaft 114. As will be described in further detail below, the plurality of shafts can be sized and shaped to be slidable relative to each other. Accordingly, it should be understood that one or more of the plurality of shafts can be concentric with respect to another of the shafts to facilitate slidable movement of the shafts relative to each other. The plurality of shafts can be coupled to one or more other components of the delivery system 100. In some embodiments, the handle 110 can include a plurality of switches, levers, knobs, or other actuatable/rotatable mechanisms which can be used to control the movement of the one or more shafts of the delivery system 100 and/or to control the operation of other components of the delivery system 100.

With continued reference to the embodiment of FIG. 1, the delivery system 100 can include outer elongate hollow member shaft 114 having a proximal and distal end. As used to describe the components of the delivery system, "proximal" refers to a location of the component that is closer to the handle 110, and "distal" refers to a location of the component that is further from the handle 110. In some embodiments, the proximal end of the outer elongate hollow member shaft 114 can be coupled to the handle 110. In some embodiments, the outer elongate hollow member shaft 114 can be fixed relative to the handle 110. In some embodiments, the outer elongate hollow member shaft 114 can be movable relative to the handle 110. The outer elongate hollow member shaft 114 can include sheath and/or capsule, and may be made of one or multiple members. The outer elongate hollow member shaft 114 can have the same diameter from the proximal to distal end, or the diameter may vary. The outer elongate hollow member shaft 114 can be formed from a variety of materials, including ePTFE and PEEK, as well as other biocompatible materials. Further, the outer elongate hollow member shaft 114 can include a coating, such as a hydrophilic coating.

In some embodiments, the outer elongate hollow member shaft 114 can cover at least a portion of a collapsed or compressed prosthesis 70 while the prosthesis 70 is being delivered to the deployment site. For example, the outer elongate hollow member shaft 114 can cover at least the second end 303 of the prosthesis 70 while the first end 301 of the prosthesis 70 is received within a hollow nose cone 118, described further below. In some embodiments, the outer elongate hollow member shaft 114 can also cover the first end 301 of the prosthesis 70. The outer elongate hollow member shaft 114 can be sized and shaped such that the outer elongate hollow member shaft 114 can retain the prosthesis 70 in a compressed state as it is delivered to the deployment site. Accordingly, the outer elongate hollow member shaft 114 can function as a "capsule" for receiving the prosthesis 70. As shown in the illustrated embodiment, the outer elongate hollow member shaft 114 can have a constant or substantially constant outer diameter throughout the entirety, or a substantial portion of the entirety, of its length. The outer elongate hollow member shaft 114 can be moveable relative to the nose cone 118 to uncover the second end 303 of the prosthesis 70 while the first end 301 of the prosthesis 70 remains engaged to tether retention mechanism (described below) within the nose cone 118 and remains covered by the nose cone 118.

The outer elongate hollow member shaft 114 can include a marker 117 positioned proximate the distal end, such as a radiopaque marker that allows for visualization by a physician. In some embodiments, the outer elongate hollow member shaft 114 can be formed of multiple layers of material, such that the outer elongate hollow member shaft 114 includes at least a first radial portion and a second radial portion. This can advantageously allow for the use of two types of material for the outer elongate hollow member shaft 114. For example, at least a portion of the first portion can be positioned radially outward from the second portion relative to a central longitudinal axis of the outer elongate hollow member shaft 114. The first portion, which may be considered an outer layer, can be formed from a relatively rigid material, such as PEBAX, ULTEM, PEEK and any other biocompatible material as desired. This can advantageously provide some degree of rigidity for the outer portion of the elongate hollow member shaft 114. The second portion, which may be considered an inner layer, can be formed from a more compliant material, such as PTFE, ePTFE and any other biocompatible material as desired. This can advantageously provide a more compliant inner surface for the outer elongate hollow member shaft 114, which can be beneficial when contacting other components of the delivery system 100 and the prosthesis. In some embodiments, the second portion can be a liner which is applied to the first portion.

While the outer elongate hollow member shaft 114 can be formed with multiple portions formed from multiple materials, it is also contemplated that the outer elongate hollow member shaft 114 can be a formed from a single material.

Additionally, the innermost shaft in the delivery system 100 can be the nose cone shaft which has a proximal end operably connected to the handle 110 and a distal end coupled to nose cone 118. The nose cone shaft may be hollow along its length to receive a guidewire, though in some embodiments the nose cone shaft is not hollow. Nose cone 118 can include an elongate, hollow portion with a proximally facing opening, and a tapered distal portion (as shown in FIG. 1). The nose cone shaft may be coupled to the nose cone 118 such that the nose cone shaft extends through the proximal opening, though the connection is not limiting. The nose cone 118 can further contain a lumen extending from the distal end of the nose cone shaft to the distal end of the nose cone 118, which can allow a guide wire to pass through. The nose cone 118 can be formed from a relatively rigid, high durometer material. The nose cone 118, including both the elongate, hollow portion and the tapered, distal portion, can have a length, measured from the distalmost end to a proximalmost end, of between approximately 5 mm to 50 mm, between approximately 10 mm to approximately 40 mm, between approximately 15 mm to approximately 25 mm, approximately 20 mm, any other lengths within these ranges, and any other lengths as desired.

The outermost diameter of the nose cone 118 can be similar to, or equal to, the outer diameter of an outer shaft and/or outer component, such as the outer elongate hollow member shaft 114. This can form a generally smooth transition in diameter between the nose cone 118 and the outer shaft and/or the outer component if and when the nose cone 118 is brought into contact with the outer shaft and/or the outer component. In some embodiments, the nose cone 118 can have an outer diameter of approximately 31 Fr or 32 Fr and the outer shaft and/or outer component can have an outer diameter of approximately 31 Fr or 32 Fr.

In some embodiments, the outer diameter of the nose cone 118 can be similar to, or equal to, the inner diameter of the outer elongate hollow member shaft 114 such that nose cone 118 can be partially received within the outer elongate hollow member shaft 114. In some embodiments, the nose cone 118 can have an outer diameter of approximately 30 Fr and the outer shaft and/or outer component can have an inner diameter of approximately 30 Fr. In some embodiments, the outer shaft can be an outermost shaft of the delivery system.

The tether retention configuration discussed below can cooperate with the nose cone 118 to release a first end 301 of the prosthesis from the nose cone 118. The first end 301 of the prosthesis 70 can be placed in a compressed state such that the first end 301 of the prosthesis 70 is retained within the nose cone 118 when the nose cone 118 is in the proximal position. Distal movement of the nose cone 118 can release the first end 301 of the prosthesis 70 from the nose cone 118, allowing it to expand. If the prosthesis 70 is not covered by the outer elongate hollow member shaft 114, once the nose cone 118 is moved distally to uncover the first end 301 of the prosthesis 70, the first end 301 of the prosthesis 70 may completely self-expand from its compressed state to an expanded configuration.

Additional details and example designs for transapical delivery systems are described in U.S. Patent Publication No. 2017/0056169, the entirety of which is hereby incorporated by reference and made a part of this specification. Further details and embodiments of a transapical delivery systems and methods of delivery are described in U.S. Patent Pub. Nos. 2018/0116790 and 2017/0056169, the entirety of each of which is hereby incorporated by reference and made a part of this specification.

Tether Prosthesis Retention

Figure 7:
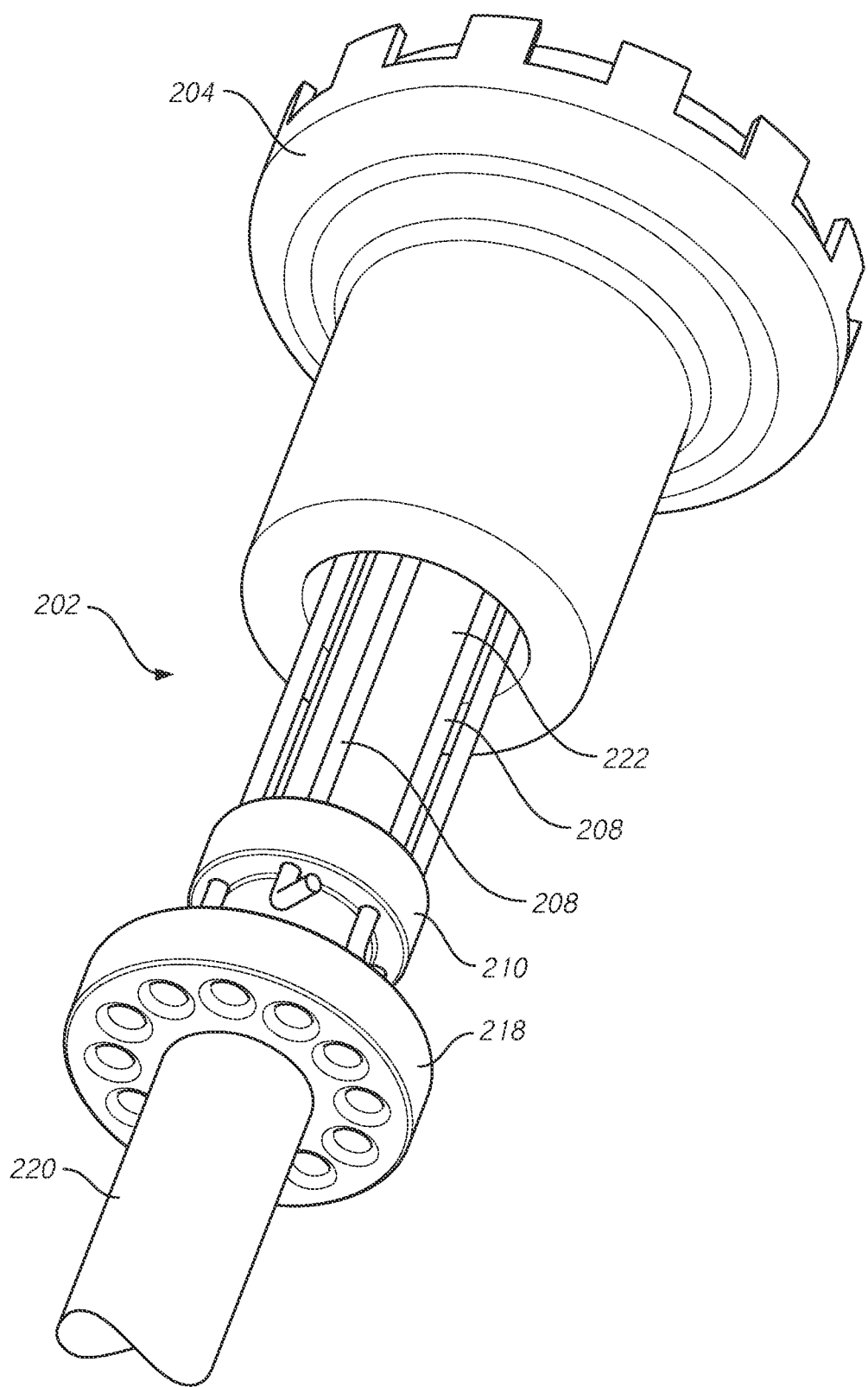
FIG. 7 illustrates a distal end of an embodiment of a delivery system.

FIG. 7 illustrates an embodiment of a distal end 202 of a delivery system 100 using one or more tethers (e.g., sutures, cords, ropes, tapes) to releasably retain the prosthesis 70 on the delivery system 100 after full expansion/partial expansion/release (e.g., tether retention mechanism), while also providing additional functionality of crimping or uncrimping the prosthesis 70, such as for recapture. For convenience of viewing, the nosecone 118, nosecone shaft, and the outer elongate hollow member shaft 114 (discussed above with respect to FIG. 1) have been removed. Similar design and release methodology as discussed in U.S. Patent Publication No. 2017/0056169 can be used, with the inner retention member being replaced by the structure discussed herein. The other components discussed in 2017/0056169 may be incorporated into the delivery system 100, such as the nosecone 118 and the outer elongate hollow member shaft 114 which can constrain the prosthesis 70 in a compressed configuration.

Advantageously, embodiments of the delivery system 100 allow the prosthesis 70 to be fully expanded (e.g., released from the nosecone 118 and the outer elongate hollow member shaft 114) but remain attached to the delivery system 100 through the use of one or more tethers. This allows the prosthesis 70 to be maneuvered after expansion, such as by translating the delivery system 100 or different shafts within the delivery system 100, for optimizing the position of the prosthesis 70 in a patient. The delivery system 100 further allows the prosthesis 70 to be compressed and withdrawn back into one or more sheathing members (e.g., nosecone 118/outer elongate hollow member shaft 114) if positioning and placement is undesirable. Thus, the prosthesis 70 may be recaptured by the delivery system 100 after expansion.

In order to use the tether attachment system, the delivery system 100 discussed above can be modified. For example, the nosecone 118 and outer elongate hollow member shaft 114 shown in FIG. 1 can be used to radially compressibly retain the first end 301 and second end 303 of the prosthesis 70, respectively, when the outer elongate hollow member shaft 114 is in its distalmost position and the nosecone 118 is in its proximalmost position. Thus, the nosecone 118 can be advanced distally and the outer elongate hollow member shaft 114 can be retracted proximally, either simultaneously or separately, to release the prosthesis 70, thereby expanding the prosthesis 70 from a compressed configuration to an expanded configuration, giving the configuration schematically shown in FIG. 8 (with the outer elongate hollow member shaft 114 and nosecone 118 removed for convenience). This operation can be performed by a user at the handle 110 of the delivery system, such as through the use of the knobs shown in FIG. 1.

Figure 8:
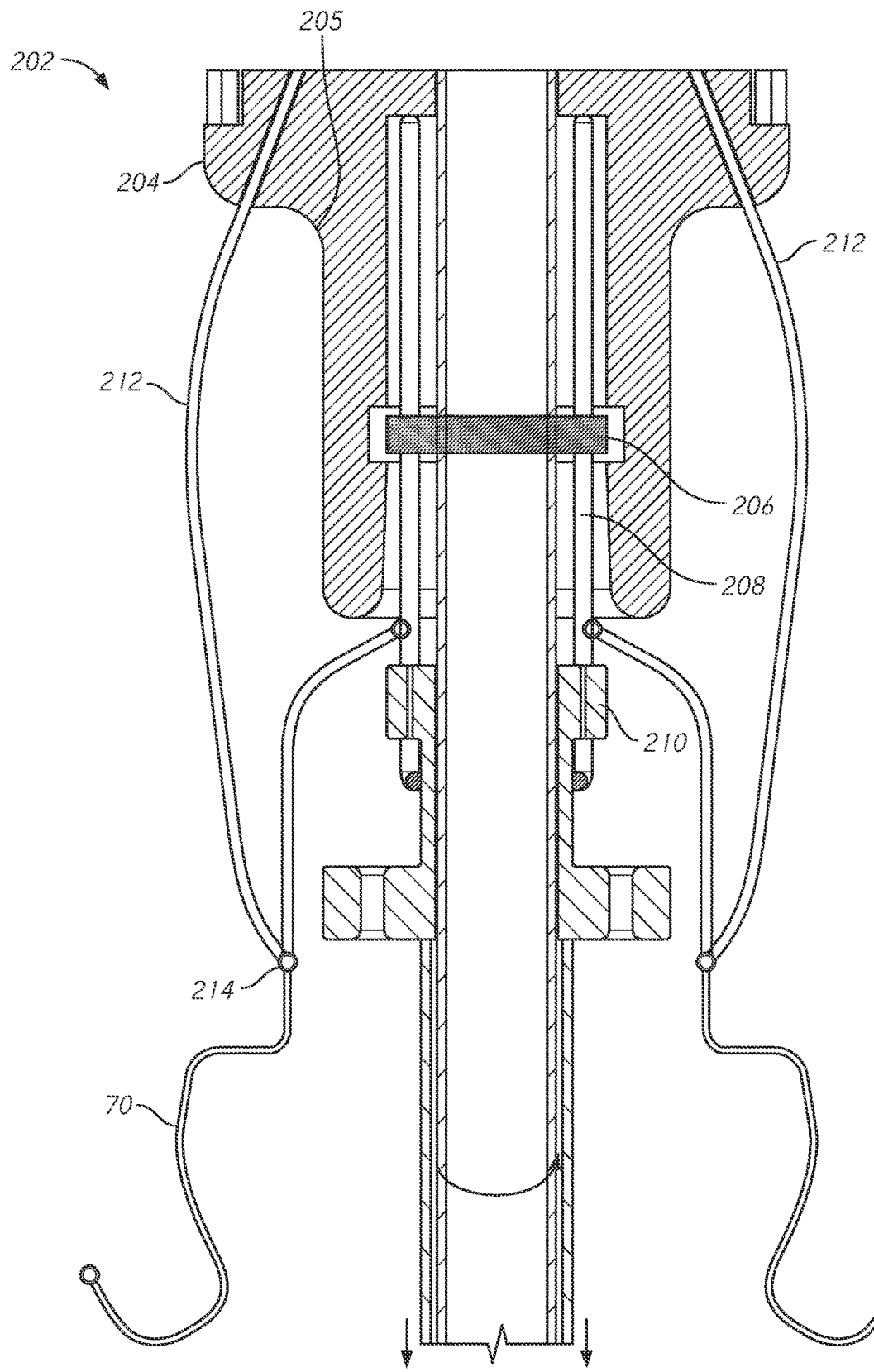
FIG. 8 illustrates an embodiment of a valve prosthesis release structure.

FIG. 8 illustrates a simplified version of distal end 202 of the delivery system 100 for convenience of explanation with the prosthesis 70 in the released (or expanded) position. Starting from the distal-most end, the delivery system 100 can include a manifold (or torqueing manifold, crown, tether attachment mechanism) 204, a bearing 206, one or more release pins 208 (e.g., members, shafts, bars), a release plate 210, and one or more tethers 212, each of which will be discussed below in more detail. In some embodiments, the manifold 204 can fit partially or fully within the nosecone 118 prior to deployment and/or after recapture, and the outer elongate hollow member shaft 114 can be slidable over the remaining components. In the closed configuration, the distal end of the outer elongate hollow member shaft 114 can abut the proximal end of the nosecone 118 to radially constrain the prosthesis 70 in a compressed configuration. The nosecone 118 can translate distally/proximally with respect to the manifold 204. The outer elongate hollow member shaft 114 can translate distally/proximally with respect to the manifold 204. Distal advancement of the nosecone 118 can uncover and release the first end 301 of the prosthesis 70, and proximal advancement of the outer elongate hollow member shaft 114 can uncover and release a second end 303 of the prosthesis 70. In particular, this approach can be used for a transapical delivery approach.

As shown in the schematic of FIG. 8, a first end of the tethers 212 (e.g., fixed end) can be attached to the manifold 204, such as at a distal end of the manifold 204, though the attachment location is not limiting. The tethers 212 can wrap around protrusions 236 at the distal end of the manifold 204 (shown in FIG. 11A) or can be otherwise physically constrained, such as with clamps, locks, friction, etc., on the manifold 204. In some embodiments, the tethers 212 can be chemically adhered to the manifold 204. The tethers 212 can extend proximally from the manifold 204 and pass through the eyelets (e.g., apertures) 214 of the prosthesis 70, such as shown in the first end 301 of the prosthesis of FIGS. 4-6. In some embodiments, the prostheses of FIGS. 2-3 can also include apertures 214 on tabs 74 as indicated. However, alternately the tethers 212 can otherwise wrap around or releasably interact/connect with the prosthesis 70, such as with those shown in FIGS. 2-3, and the disclosure is not so limited by the apertures or attachment mechanism to the prosthesis 70.

After attaching to the prosthesis 70, the tethers 212 can extend distally (e.g., towards the manifold 204) from the prosthesis 70 where the second end of the tethers 212 (e.g., temporary or removable end) can be attached onto, for example, release pins 208. The tethers 212 can attach to the release pins 208 such as by looping around a portion of the release pins 208, though the particular attachment is not limiting. Thus, the prosthesis 70, in particular the first end 301, can be held onto the delivery system 100 through the use of the tethers 212 after expansion of the prosthesis 70. Additionally, as shown, the manifold 204 and/or the release pins 208 and/or bearing 206 can be located generally distally to the prosthesis 70 in the expanded state. In some embodiments, a second manifold can be located proximal to the prosthesis 70, and a similar configuration can be used to attach the second end 303 to the secondary manifold. Alternatively, a tether loop attached to the handle 110 can at least partially surround the second end 303 to slow expansion, such as discussed in U.S. Pat. Publication No. 2017/0056169.

Further, FIG. 8 shows a schematic of prosthesis 70 in the uncrimped and expanded state where the prosthesis 70 is relatively freely floating, though still attached to the delivery system 100 by the tethers 212. As shown, the tethers 212 can be attached to a portion of the first end 301 of the prosthesis 70. As discussed in more detail, the expanded prosthesis 70 can be crimped down (e.g., compressed) so that the first end 301 wraps around and outer circumferential surface 205 of the manifold 204 or other portion of the delivery system 100, either for the initial expansion of the first end 301 or for recapture of the first end 301. Specifically, spooling (or tensioning) and unspooling (or untensioning) of the tethers 212 between the delivery system and the prosthesis 70 can crimp/uncrimp the prosthesis 70.

The delivery system 100 can include the same, more, or less tethers 212 than apertures 214 on the prosthesis 70. In some embodiments, the delivery system 100 can use 1, 2, 3, 4, 5, 6, 7, 8, 9, 10, 11, 12, 13, 14, 15, 16, 17, 18, 19, or 20 tethers 212 for connecting the prosthesis 70 to the delivery system 100. In some embodiments, each aperture 214 contains a different tether 212. In some embodiments, a tether 212 may pass through multiple apertures 214. While FIG. 8 only shows two tethers for convenience, it will be understood that every aperture 214 of the valves of FIGS. 2-6 can receive a different tether, or that apertures may not be required. In some embodiments, a single unbroken tether 212 may be used. The tethers 212 can be configured to stretch in certain embodiments, or relatively unstretchable in other embodiments.

As mentioned above, the second end of the tethers 212 can releasably attach onto release pins 208, such as by a tether loop which can slide along the release pins 208, as shown in FIG. 8. In some embodiments, each tether 212 can attach to a different release pin 208. In some embodiments, a release pin 208 may be attached to by multiple tethers 212. In some embodiments, a tether 212 may attach to more than one release pin 208.

Figure 9:
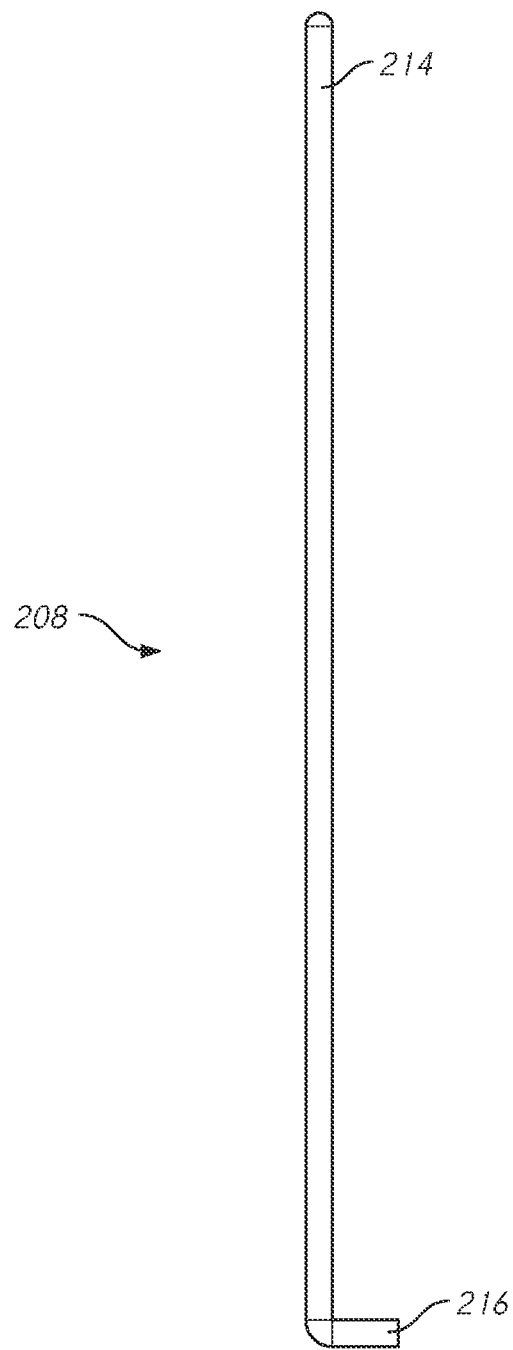
FIG. 9 illustrates an embodiment of a release pin.

In some embodiments, the release pins 208 have a generally L-shape with a straight portion 214 attached to a bent portion 216 to form the L as shown in FIG. 9. In certain implementations, the bent portion 216 can be located at the proximal end of the release pins 208. In some embodiments, straight portion 214 can consist of 90, 95, 98, or 99% of the length of the release pin 208. In some embodiments, the bent portion 216 can be at an angle of about 80, 85, 90, 95, 100, 105, 110, 115, 120, or 125° with respect to the straight portion 214. In some embodiments, the release pins 208 may have enlarged pin heads instead of the bent portion 216, or other mechanism to prevent distal motion through the release plate 210. In some embodiments, the release pins 208 can include threading, where the release pins 208 rotate upon proximal translation.

Figure 10:
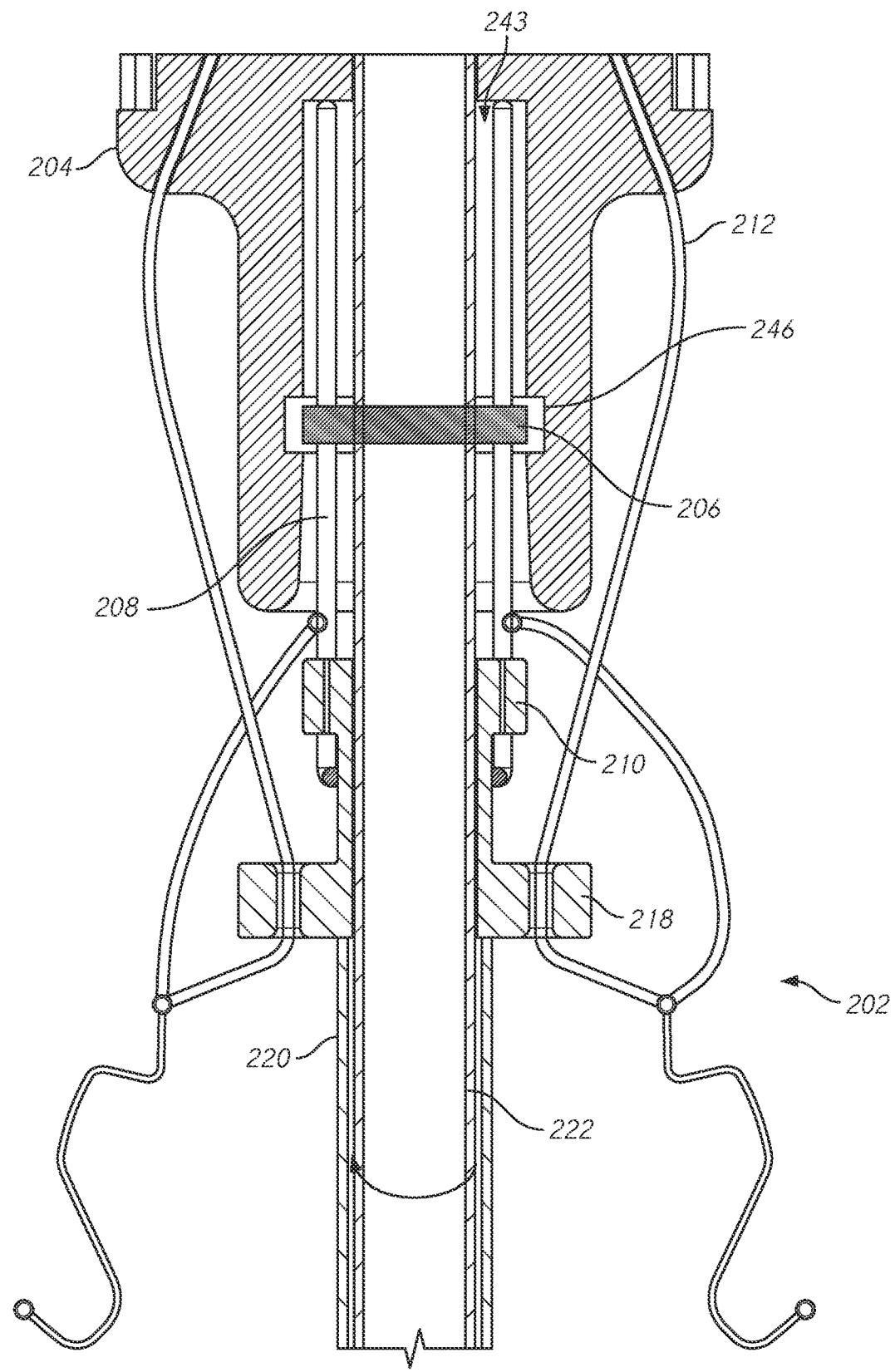
FIG. 10 illustrates an embodiment of a distal end of a delivery system with a valve prosthesis release structure.

As shown in FIG. 10, when in the locked position, the straight portion 214 of the release pins 208 can extend distally towards an inner proximal surface of the manifold 204. In some embodiments, the manifold 204 can include indentations or other capture mechanisms to receive the distal ends of the straight portions 214. As shown, the straight portion 214 can extend through apertures in bearing 206 which can be located within the manifold 204 in order to make sure the pins 208 remain aligned. Near the proximal end of the pins 208, the straight portion 214 of the pins 208 pass through apertures in the release plate 210 and the bent portion 216 remains on the proximal end of the release plate 210, on a pin retention face, preventing any further distal motion of the pins 208 due to the bent portion 216 not fitting through apertures in the release plate 210. Further, excess proximal motion of the pins 208, which could release the tethers 212, is prevented as the pins 208 would abut a distal end of the suture guide 218. Thus, as shown in FIGS. 8 and 10 in the locked position the second end of the tethers 212 are held on the pins 208 between the bearing 206 and the release plate 210, preventing release of the releasable end of the tethers 212 (and thereby preventing release of the prosthesis 70).

When it is desirable to release the prosthesis 70 from the delivery system 100, the release plate 210 can be translated (e.g., pulled, moved) proximally, such as by a user at a handle 110 of the delivery system 100, thus providing a proximal force on the bent portion 216 and pulling the pins 208 proximally with respect to the bearing 206. A user can pull on a portion of a handle 110, or activate an actuator (such as a button or knob) to withdraw the release plate 210. Once the pins 208 are fully pulled proximally through the bearing 206, the straight portions 212 come free from the bearing 206 and the tethers 212 are released as the bearing 206 no longer blocks the path of the second end of the tethers 212 (the first end of the tether 212 continues to remain on the manifold 204). In some embodiments, as the tethers 212 are under tension when attached they will automatically be released from the pins 208 once the pins 208 are released from the bearing 206. In some embodiments, the tethers 212 can be manually removed from the pins 208 by a user. Once the second end of the tethers 212 are released from the pins 208, the prosthesis 70 can fully release from the delivery system 100.

FIG. 10 illustrates a more detailed embodiment of a distal end of the delivery system shown in FIG. 8, and includes some further components which may be used in some embodiments. For example, FIG. 10 illustrates two shafts, the pin lock shaft 220 and the manifold shaft 222, the manifold shaft 222 being concentrically located within a lumen of the pin lock shaft 220. The distal end of the manifold shaft 222 can connect to the manifold 204, such as shown in FIG. 10. The distal end of the pin lock shaft 220 can connect to the release plate 210 and/or the tether guide 218, discussed below. The pin lock shaft 220 can be translated distally and proximally, such as by a user at a handle 110 of the delivery system 100, to release the pins 208 as discussed above. The manifold shaft 222 can further include a lumen for other components, such as a nosecone shaft discussed above, to pass through. Further, either the pin lock shaft 220 or the manifold shaft 222, or both shafts, can be configured for rotational motion with respect to each other, such as by a user at a handle 110 of the delivery system 100, as discussed below. Additionally, the outer elongate hollow member shaft 114 can translate over the pin lock shaft 220 in order to compress the prosthesis 70. Thus, the pin lock shaft 220 and the manifold shaft 222 can be located within a lumen of the outer elongate hollow member shaft 114.

As shown in FIG. 10, some embodiments of the delivery system 100 can include a tether guide 218 located proximal of the release plate 210. The tether guide 218 can include a number of apertures for the tethers 212 to pass through, thus preventing tangling of the tethers 212, and assisting in the crimping/uncrimping of the prosthesis 70. As shown, the tethers can extend from the manifold 204 to enter a distal end of the tether guide 218 and pass out the proximal end of the tether guide 218 through the prosthesis 70 and back distally to the release pin 208. However, this particular approach is not limiting and the tethers may enter/exit either side of the tether guide 218. In some embodiments, the tether guide 218 is attached to the release plate 210. In some embodiments, the tether guide 218 may not be used. In some embodiments, the tether guide 218 may only be a protrusion that prevents proximal motion of the pins 208.

Figure 11A:
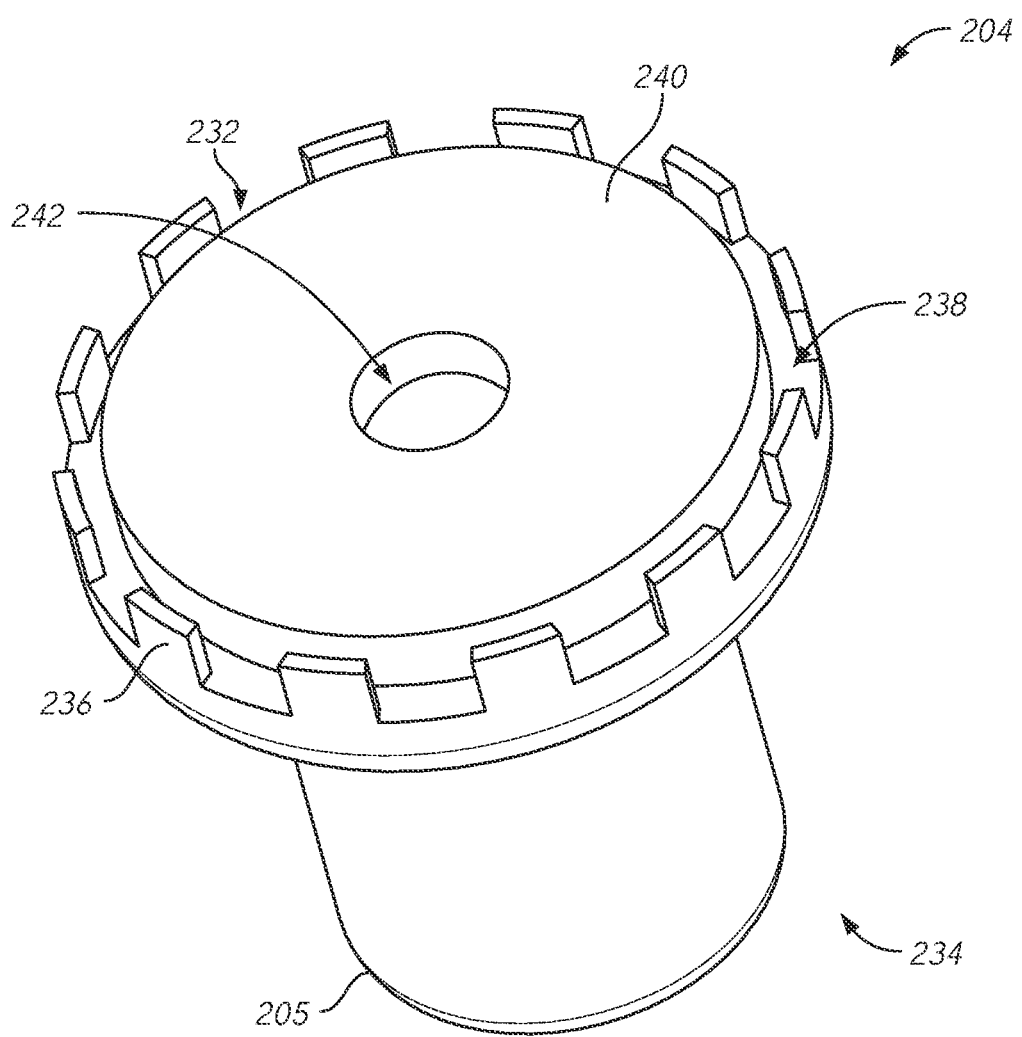
FIGS. 11A-11C illustrate an embodiment of a manifold.
Figure 11B:
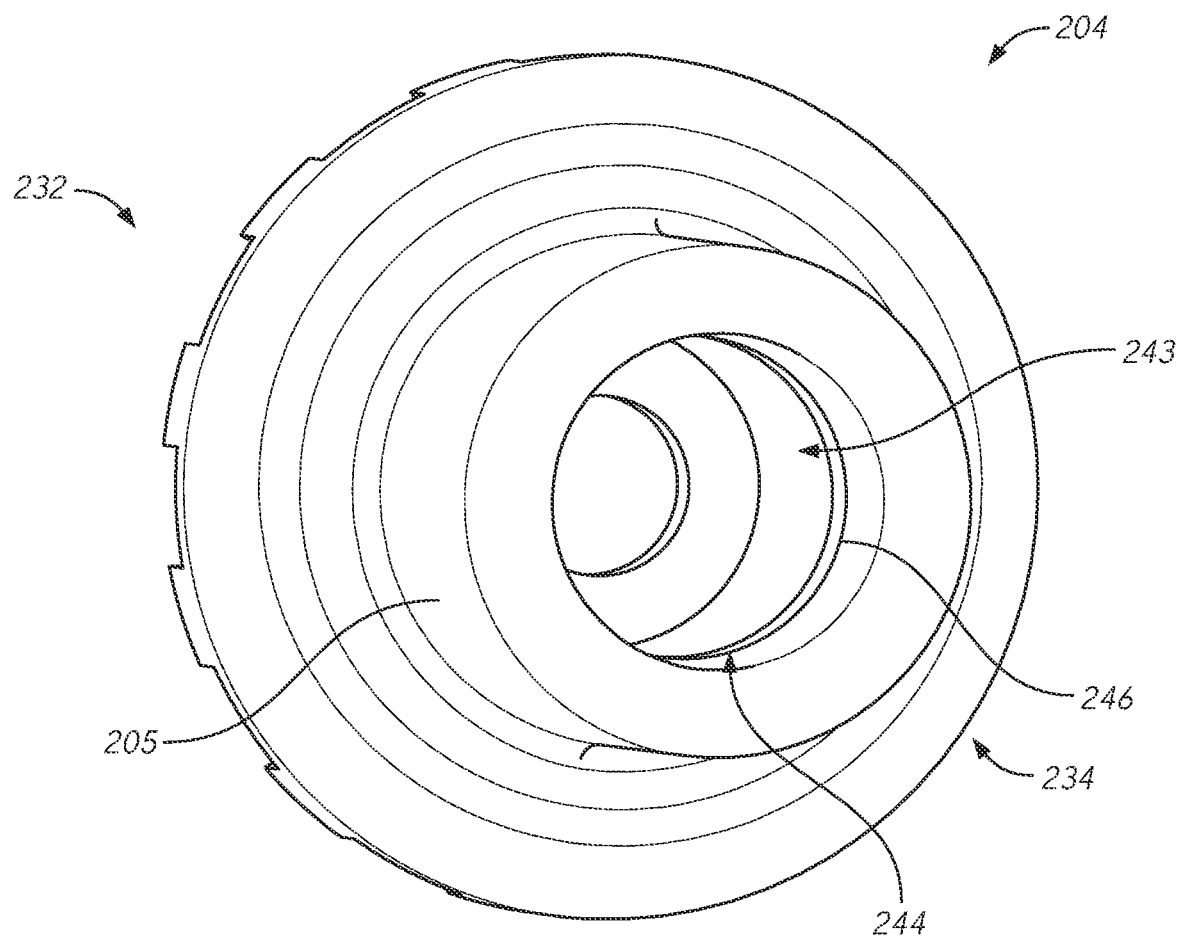
Figure 11C:
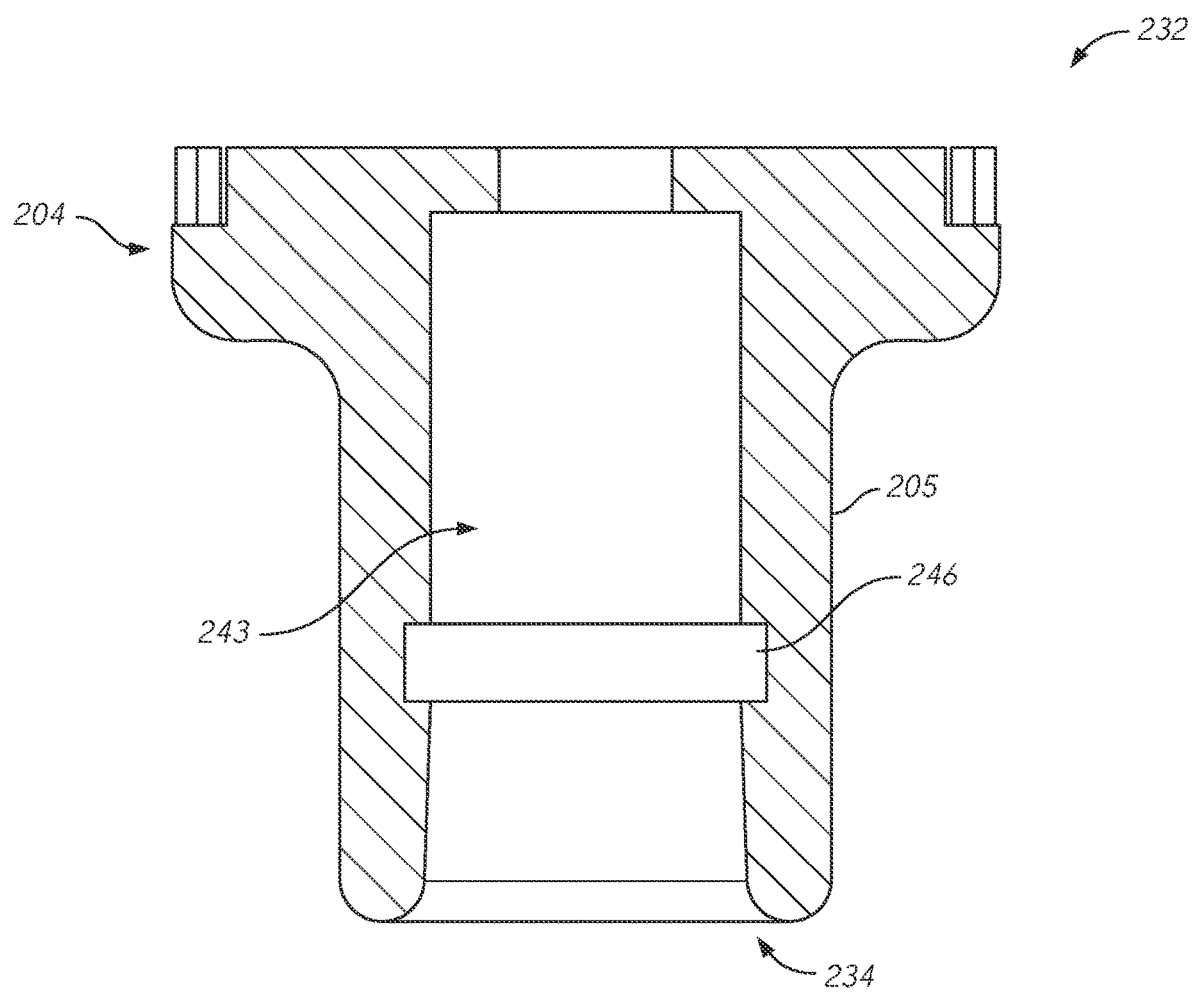

Moving to the individual components, FIGS. 11A-11C illustrate the manifold 204 removed from the delivery system 100. The manifold 206 can include a distal end 232 and a proximal end 234. The manifold 206 can be sized to fit within a nosecone, or to abut against a proximal end of a nosecone. As shown, the distal end 232 can include a crown of tabs (e.g., protrusions, jaws) 236 surrounding a ring-shaped gap 238, which in turn surrounds a raised circular protrusion 240. The protrusion 240 can include an aperture 242 generally in the middle and extending proximally to distally, which can receive one or more shafts, such as a nosecone shaft.

The tabs 236 can be used to wrap/wind one end of the tether 212 around (such as by using a loop), thereby retaining the tether 212 onto the manifold 204. In some embodiments, the tabs 236 can be bent or crushed inwards in order to permanently retain the end of the tether 212. In some embodiments, the tethers 212 can be permanently affixed to the manifold 204 through other means, such as by adhesives or mechanical fastening. As shown, the manifold 204 can include twelve tabs 236 for twelve tethers 212, though the particular number of tabs does not limit the disclosure. There can be the same number of tabs 236 as there are tethers 212. For example, there can be 2, 3, 4, 5, 6, 7, 8, 9, 10, 11, 12, 13, 14, 15, 16, 17, 18, 19, or 20 tabs 236. Moving radially inwards is a gap 238 which has a general ring shape, and inwards of the gap 238 is the raised circular protrusion 240. The gap 238 can be sized configured to allow the protrusions 236 to bend into the gap 238 to hold the tethers 212.

Moving proximally, the diameter of the manifold 204 can be reduced, for example in a step reduction, though in other embodiments there is no reduction of diameter. Therefore, the proximal end 234 of the manifold 204 can have a smaller diameter than the distal end 232, such as ¼, ⅓, or ½ the diameter. This makes it so the first end 301 of the prosthesis 70 can circumferentially surround the proximal end 234 proximal the step, such as at surface 205, in the fully crimped position and be within the diameter of the distal end 232 so that the prosthesis 70 does not get caught by the nosecone 118 upon recapture. As shown in FIG. 11B, the proximal end 234 can include a larger diameter aperture 244, extending proximally to distally, than the aperture 242 on the distal end 232. The aperture 244 can form a hollow space 243, for example generally cylindrical, within the manifold 204. Accordingly, the manifold shaft 222 can fit within the aperture 244 and into the hollow space but not extend through aperture 242. Further, the hollow space can receive the bearing 206, as shown in FIG. 10.

FIG. 11C illustrates a cross section of the manifold 204 with the bearing 206. In some embodiments, the hollow space 243 can include indentations 246 to receive and retain the bearing 206, such as shown in FIG. 10. In some embodiments, the bearing 206 can be snap fit into the manifold 204.

Figure 12:
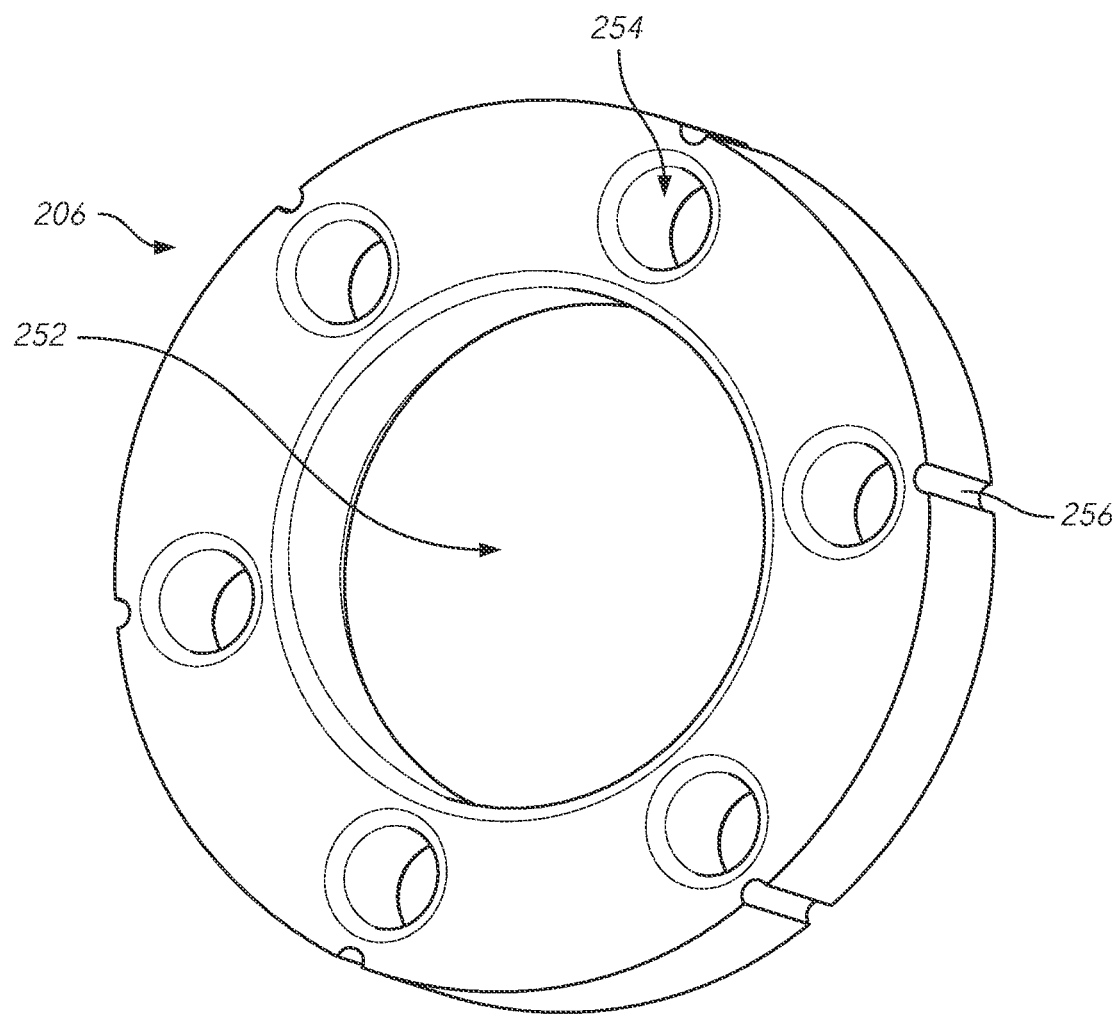
FIG. 12 illustrates an embodiment of a bearing.

Next, FIG. 12 shows the bearing 206. As shown, the bearing 206 can be generally shaped like a ring or cylinder, though the particular shape is not limiting. The bearing 206 can include a center aperture (or lumen) 252 extending proximally to distally which can be sized to receive the manifold shaft 222, which can retain a nosecone shaft in its inner lumen. The bearing 206 can further include a number of smaller apertures 254 around its circumference, extending from the proximal side to the distal side. The apertures 254 can be sized to receive the straight portion 214 of the release pins 208. The apertures 254 can be evenly spaced around the circumference in some embodiments. There can be an equal number of apertures 254 as there are release pins 208, for example 2, 3, 4, 5, 6, 7, 8, 9, 10, 11, or 12 apertures 254. However, there may be more apertures 254 than release pins 208 in some implementations.

Further, in certain implementation the bearing 206 can include notches 256 on an outer circumferential surface of the bearing 206. The notches can be aligned with the apertures 254 in some implementations. In some embodiments, an inner surface of the manifold 204 can include protrusions that mate with the notches 256 for proper initial alignment, though the bearing 206 is free to circumferentially rotate within the manifold 204 after initial insertion. Other implementations include protrusions on the bearing 206 and notches on the inner surface of the manifold 204. In some embodiments, notches are not used on the bearing 206. In some embodiments, the bearing 206 is free to rotate circumferentially within the manifold 204 and around the manifold shaft 222. This allows proper alignment of the release pins 208 with respect to the release plate 210.

Figure 13:
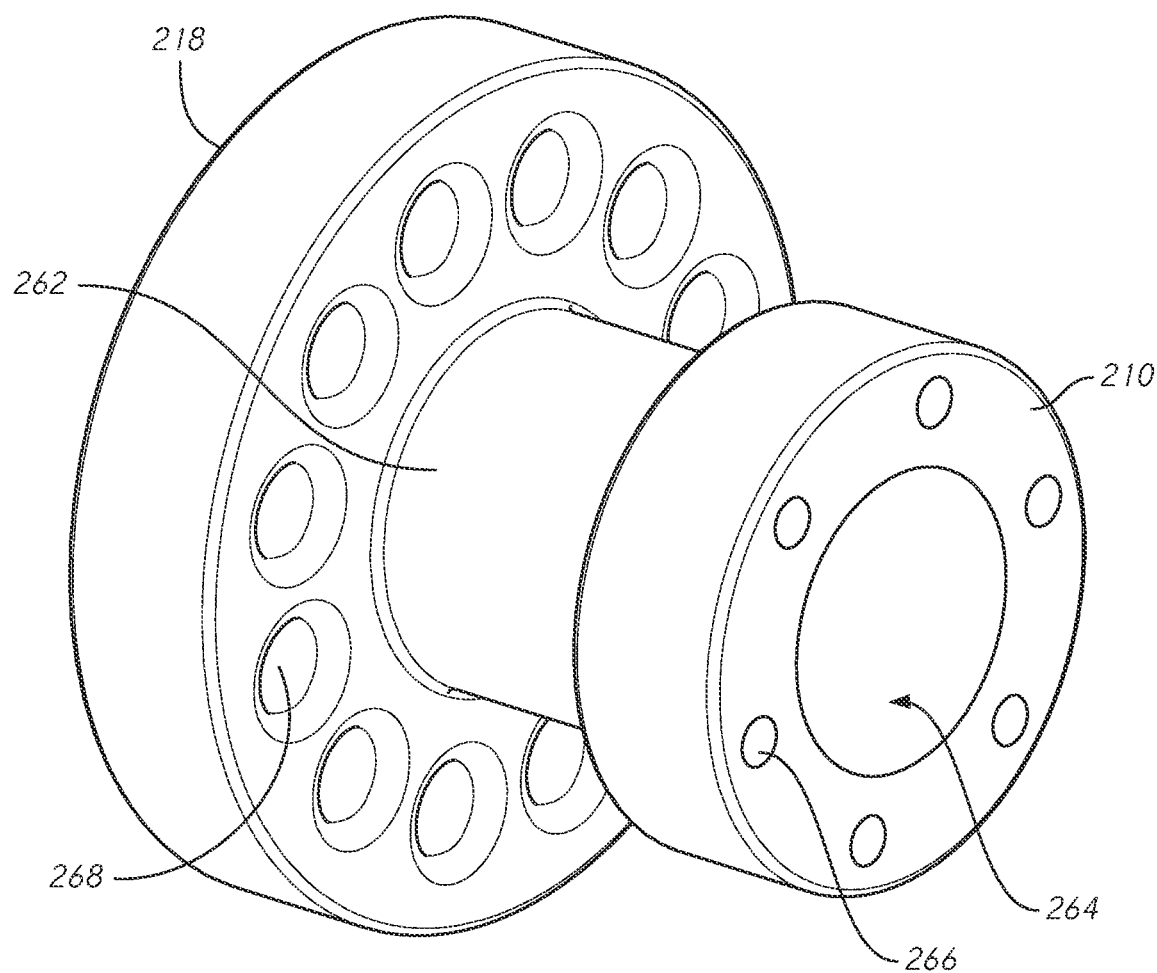
FIG. 13 illustrates an embodiment of a release plate and tether guide.

Moving proximally on the delivery system 100, FIG. 13 illustrates the combination of the release plate 210 and the tether guide 218. As shown, a center shaft 262 can connect the centers of the release plate 210 and tether guide 218 so that the components are longitudinally spaced apart. The release plate 210, tether guide 218, and center shaft 262 can all include a single lumen 264 for a shaft, such as the manifold shaft 222, to pass through. The center shaft 262 may have a smaller diameter than the tether guide 218 and the release plate 210. In some embodiments, a center shaft 262 is not used, and the tether guide 218 and release plate 210 can be two separate components. For example, the release plate 210 can be located at the distal end of the pin lock shaft 220 and the tether guide 218 can be spaced proximally from the release plate 210 on the pin lock shaft 220. Both the release plate 210 and the tether guide 218 can be generally cylindrical or ringlike in shape.

The release plate 210 can be similar to the bearing 206 discussed above, and can have a number of apertures 266 extending proximally to distally and spaced around the outer circumference for receiving the release pins 208. The apertures 266 can be sized to receive the straight portion 214 of the release pins 208, but prevent the bent portion 216 from translating distally. The apertures 266 can be evenly spaced around the circumference in some embodiments, and can generally align with the apertures 254 on the bearing 206. There can be an equal number of apertures 266 as there are release pins 208, for example 2, 3, 4, 5, 6, 7, 8, 9, 10, 11, or 12 apertures 266. In some embodiments, there are more apertures 266 than release pins 208.

The tether guide 218 can also include a number of apertures 268 on an outer circumference extending proximally to distally configured to allow the tethers 212 to pass through. In some embodiments, there can be as many apertures 268 as tethers 212 or as protrusions 236 on the manifold 204. For example, there can be 2, 3, 4, 5, 6, 7, 8, 9, 10, 11, 12, 13, 14, 15, 16, 17, 18, 19, or 20 apertures 268. The tether guide 218 may have the same diameter as the release plate 210, or may have a greater diameter than the release plate 210.

Figure 14:
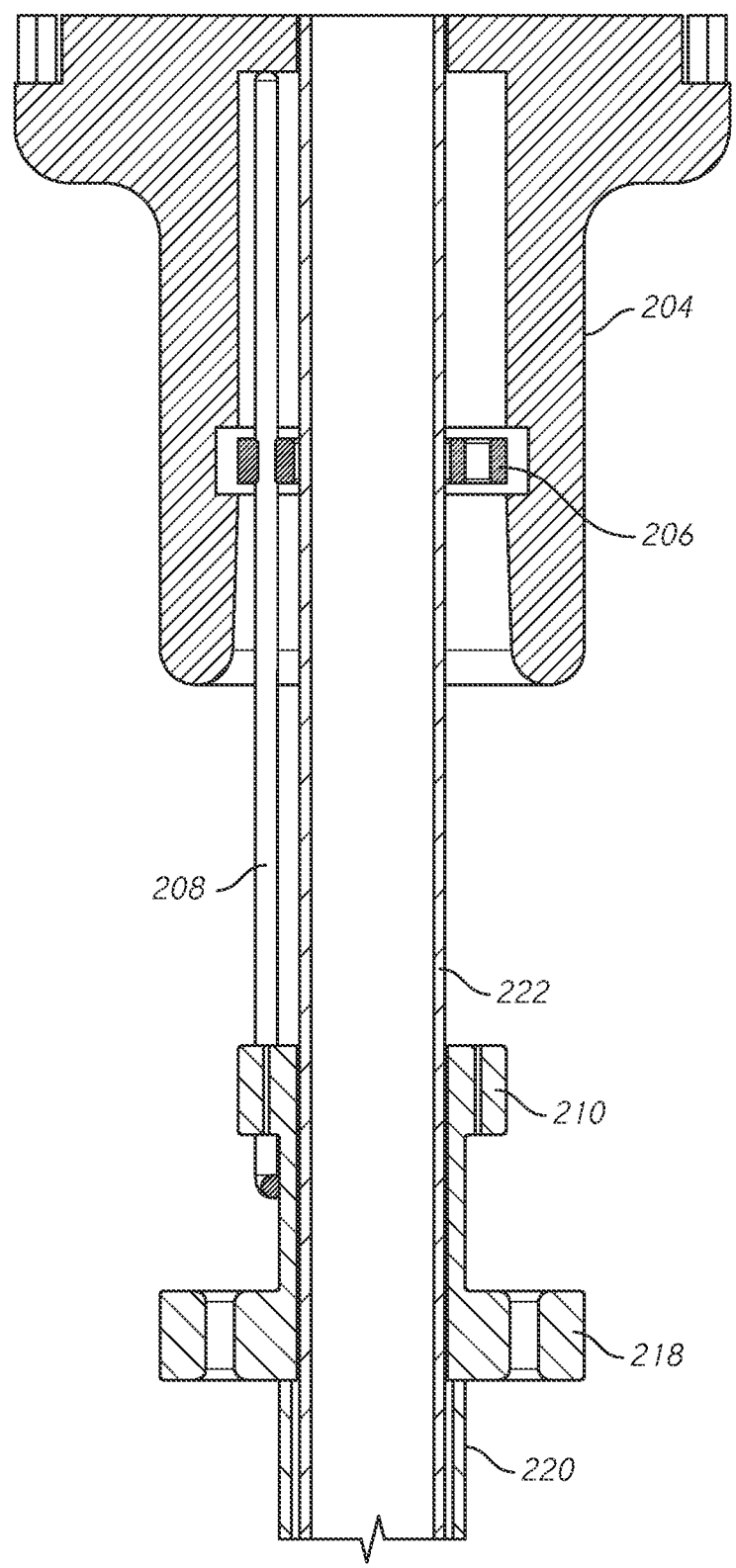
FIG. 14 illustrates a cross section of a distal end of an embodiment of a delivery system.
Figure 15A:
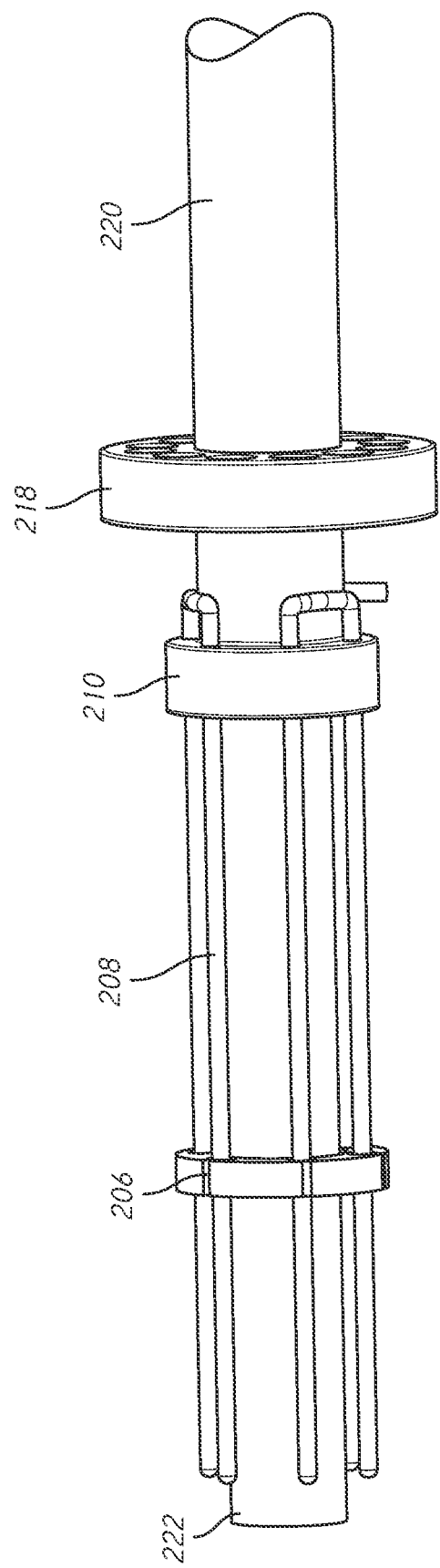
FIGS. 15A-15B illustrate a distal end of an embodiment of a delivery system with the manifold removed.
Figure 15B:
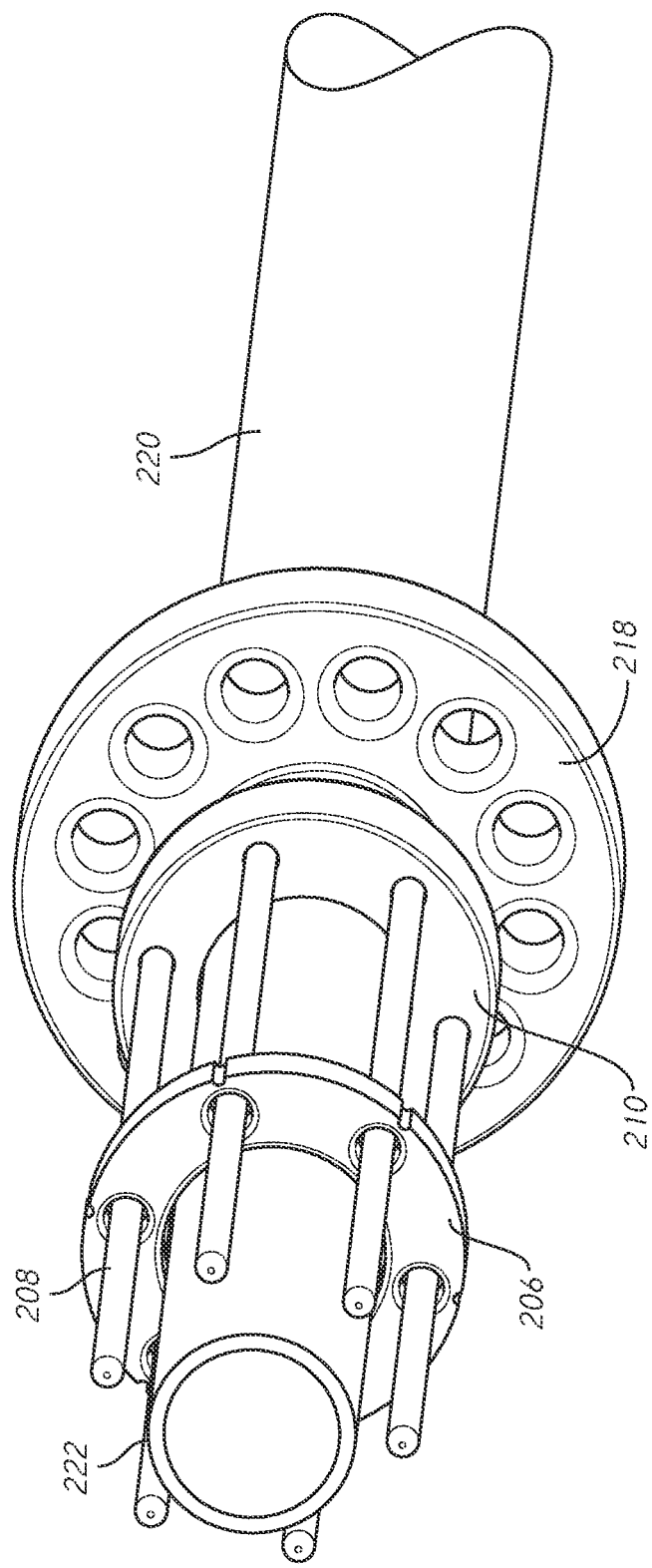

FIG. 14 illustrates a cross section of the distal end of the delivery system showing one pin 208. FIGS. 15A-15B illustrate the distal delivery system with the manifold removed 204 for clarity, showing the connection of the pins 208 between the release plate 210 and the bearing 206.

As discussed above, embodiments of the delivery system 100 can be used to retain the prosthesis 70 after expansion. Thus, the prosthesis 70 can be moved within a patient by moving the delivery system 100 upon release of the prosthesis 70.

Advantageously, components in the delivery system 100 can be torqued or rotated to provide crimping/uncrimping forces onto the prosthesis 70, in particular the first end 301 which is attached by tethers 212. Specifically, the manifold shaft 222 can be circumferentially rotated within the lumen of the pin lock shaft 220. Alternatively, the pin lock shaft 220 can be circumferentially rotated with respect to the manifold shaft 222. This can be done by the user, for example at the handle 110 such as through knobs or other actuators. Thus, the manifold 204 (holding the first end of the tethers 212) can be rotated with respect to the engagement pins 208 (holding the second end of the tethers 212). Accordingly, the tethers 212 will be pulled tight as the ends of the tethers 212 move away from one another, and the tethers 212 will loosen as the ends are moved towards one another. This tightening and loosening of the tethers 212 will pull the first end 301 of the prosthesis 70 radially inwards, thus causing crimping/uncrimping of the prosthesis 70. When the prosthesis 70 is crimped, the nosecone can be slid over the first end 301 of the prosthesis 70 for recapturing of the prosthesis 70.

Embodiments of the disclosed delivery system 100 can be inserted into a patient, such as in a transapical approach. The prosthesis 70 can be generally aligned with the native mitral valve (or other valve). The nosecone 118 can be advanced distally, thereby uncovering the first end 301 of the prosthesis 70, which allows the prosthesis 70 to begin expansion. The prosthesis 70 is still attached to the delivery system 100 by the tethers 212. Further, the outer elongate hollow member shaft 114 can be translated proximally to release the second end 303 of the prosthesis 70, which allows the prosthesis 70 to be fully expanded while still connected to the delivery system 100 by the tethers 212.

Upon full expansion of the prosthesis 70, it can be determined whether the prosthesis 70 is located in the proper position within the patient. If necessary, the manifold shaft 222 and pin lock shaft 220 can be circumferentially rotated with respect to one another to crimp at least the first end 301 of the prosthesis 70. The nosecone 118 can then be proximally retracted to cover the first end 301, so that the prosthesis 70 can be repositioned or withdrawn from the patient.

Once the prosthesis 70 is in the correct position, it can be released from the delivery system 100. For example, the pin lock shaft 220 can be translated proximally, thereby releasing the pins 208 from the bearing 206. Once released, the tethers 212 are released from the pins 208, thereby disconnecting the prosthesis 70 from the delivery system 100. The delivery system 100 can then be withdrawn through a lumen in the prosthesis 70 for removal. In some embodiments, the nosecone is retracted proximally and the outer elongate hollow member shaft can be advanced distally so that the two components contact one another. This can alleviate any issues of the delivery system 100 catching on the prosthesis 70 during removal. In other implementations, the nosecone and outer elongate hollow member shaft do not need to be moved after release of the prosthesis 70 for removal of the delivery system 100.

While the above description discusses the use of tethers and pins for releasable connection of the prosthesis, other engagement mechanisms can be used as well and the disclosure is not so limited. For example, the tethers can be releasably attached by clips, locks or clamps to a portion of the delivery system 110. Additionally, frictional components or chemicals/adhesives can be used which can be overcome by an applied force greater than that applied by the expanded prosthesis 70. Further, other locking structures can be manipulated to release one or more ends of the tether, such as at the handle 110 of the delivery system 100. Thus, while the above tethers can be used to connect the prosthesis 70 to the handle 110, other methods or release can be used, and the disclosure is not so limited.

In some embodiments, a similar structure as described above, but reversed proximally/distally, can be used to retain the second end 303 of the prosthesis 70. For example, the manifold 204 can be located proximal to the prosthesis 70 and the position of the prosthesis 70 and manifold 204 can be reversed (e.g., the first end 301 is proximal to the second end 303). Accordingly, the tether guide 218 and release plate 210 will be aligned distal to the prosthesis 70. Thus, a transseptal delivery system, such as disclosed in U.S. Patent Pub. No. 2017/0056171, hereby incorporated in its entirety, can be used with the components discussed above. For example, the outer retention ring/midshaft and the inner retention ring/inner shaft can be replaced with the manifold/locking shafts discussed above.

Valve Crimp and Tilt Ring

Disclosed are embodiments of a valve crimp and tilt ring (e.g., crimping ring) for aided prosthesis recapture and repositioning post-deployment. In some embodiments, it can be advantageous to be able to reposition the prosthesis 70 after partial or full expansion of the valve from the delivery system. Further, it may be necessary to partially or fully recapture a partially or fully expanded prosthesis 70 for a number of reasons, such as incorrect positioning within a heart. Embodiments of the disclosed ring can be optionally used with respect to the suturing retention mechanism discussed above. However, in some embodiments the ring is not used. Further, the ring system can be used without the suturing retention system discussed above.

In some embodiments, the ring may be used to crimp the prosthesis 70 instead of the rotational torqueing discussed above the manifold shaft 222. In some embodiments, the ring may fit within a nosecone 118 of the delivery system 100. For example, the ring may freely float within the nosecone 118. In some embodiments, the ring can allow the nosecone 118 to have a 30 French outer diameter, a 27 French outer diameter, or less than 30 French or less than 27 French outer diameter.

Figure 16A:
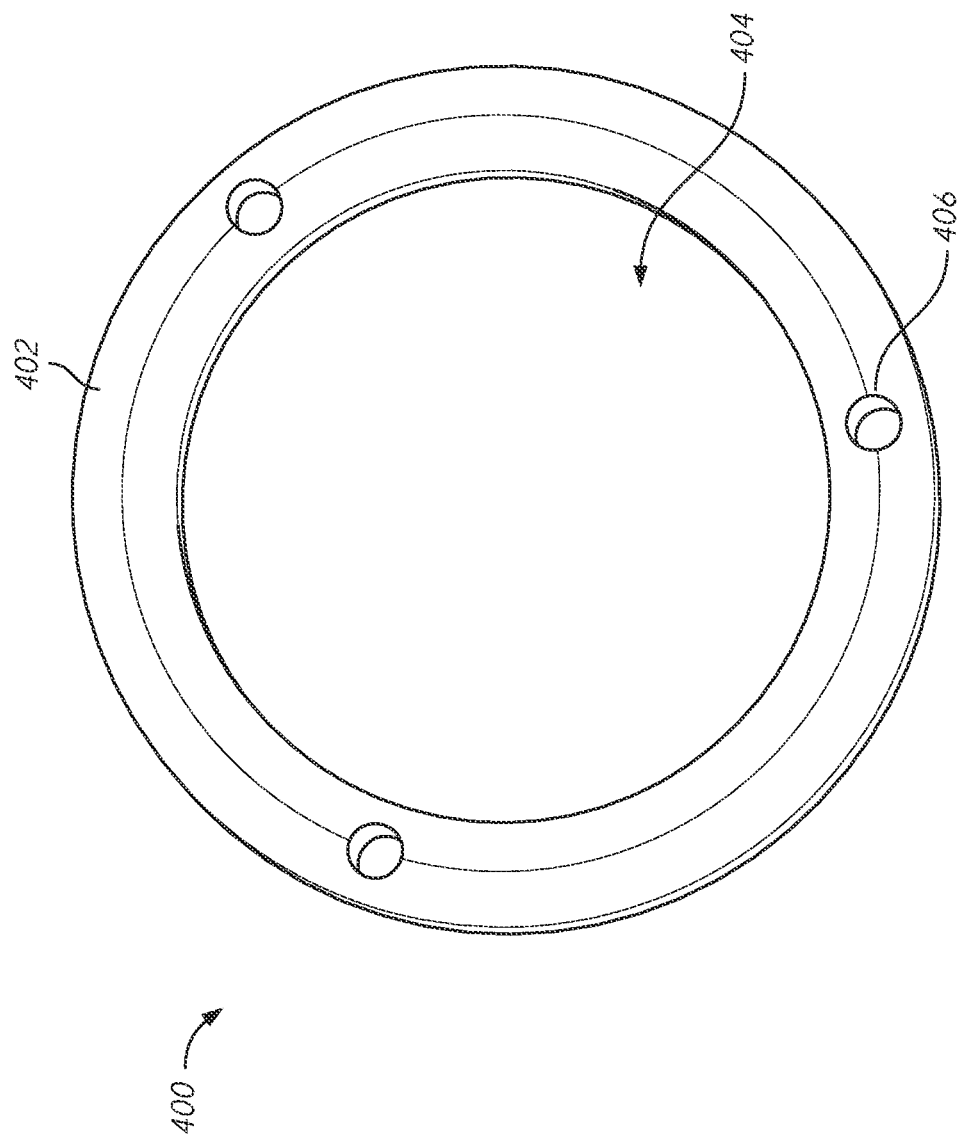
FIGS. 16A-16B illustrate an embodiment of a valve tilt and crimp ring.
Figure 16B:
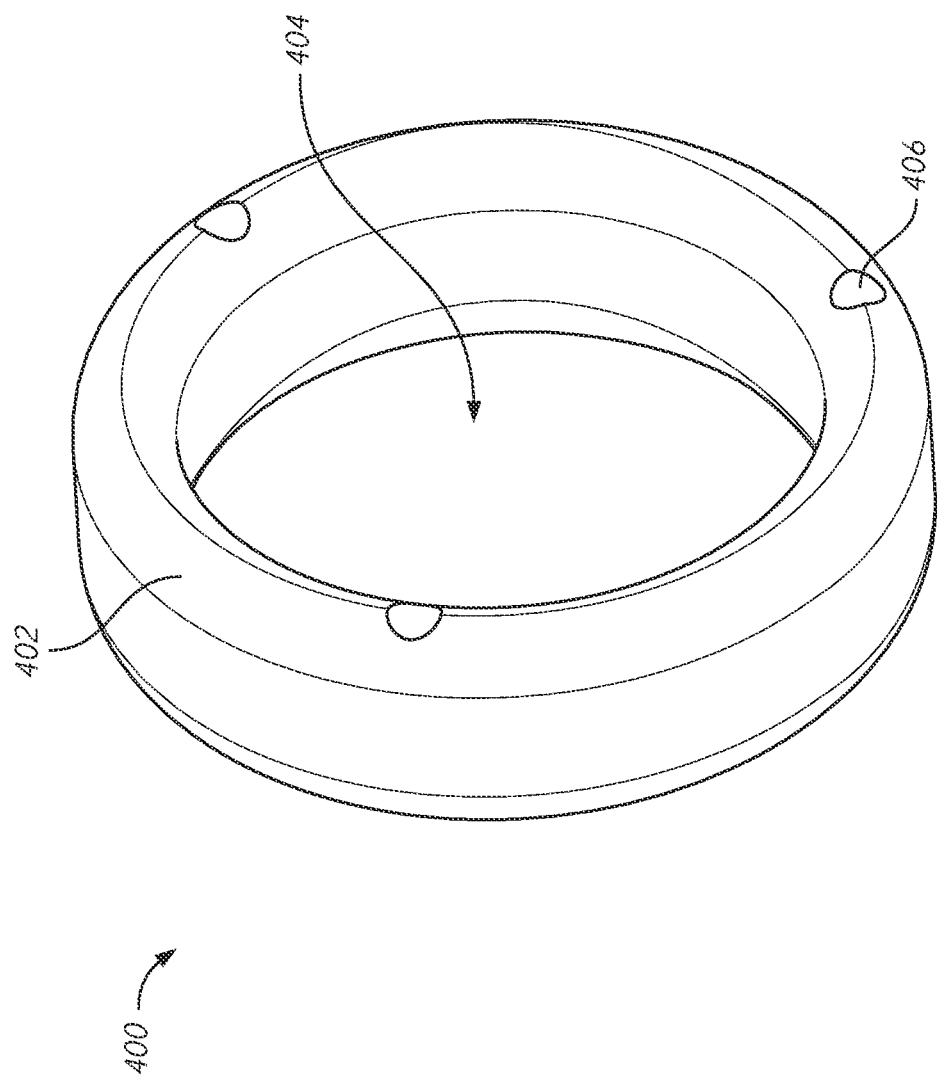

FIGS. 16A-16B illustrate different views of the ring 400. The ring 400 includes a body 402, in some embodiments a generally circular or ring-body, with a large center lumen 404 extending proximally to distally and a number of apertures 406 extending proximally to distally through the body 402. While the ring 400 of FIGS. 16A-16B has a thickness (e.g., proximally to distally) less than the diameter, in some embodiments the thickness can be equal to or greater than the diameter, thereby forming a tube or cylinder instead of a ring.

The lumen 404 can be sized to receive and surround a portion of the prosthesis 70, in particular the first end 301 of the prosthesis 70, along with the tethers 212 attaching the prosthesis 70 to the manifold 204 discussed above. Prior to any crimping, the ring 400 can be located distal to the prosthesis 70.

As mentioned, the ring 400 can include a number of the smaller apertures 406. In some embodiments, they are spaced evenly around the circumference of the ring 400. In some embodiments, they are not spaced evenly around the circumference of the ring 400. The ring 400 can include 1, 2, 4, 5, 6, 7, 8, 9, or 10 apertures 404. In some embodiments, the apertures 406 may be notched.

Figure 17:
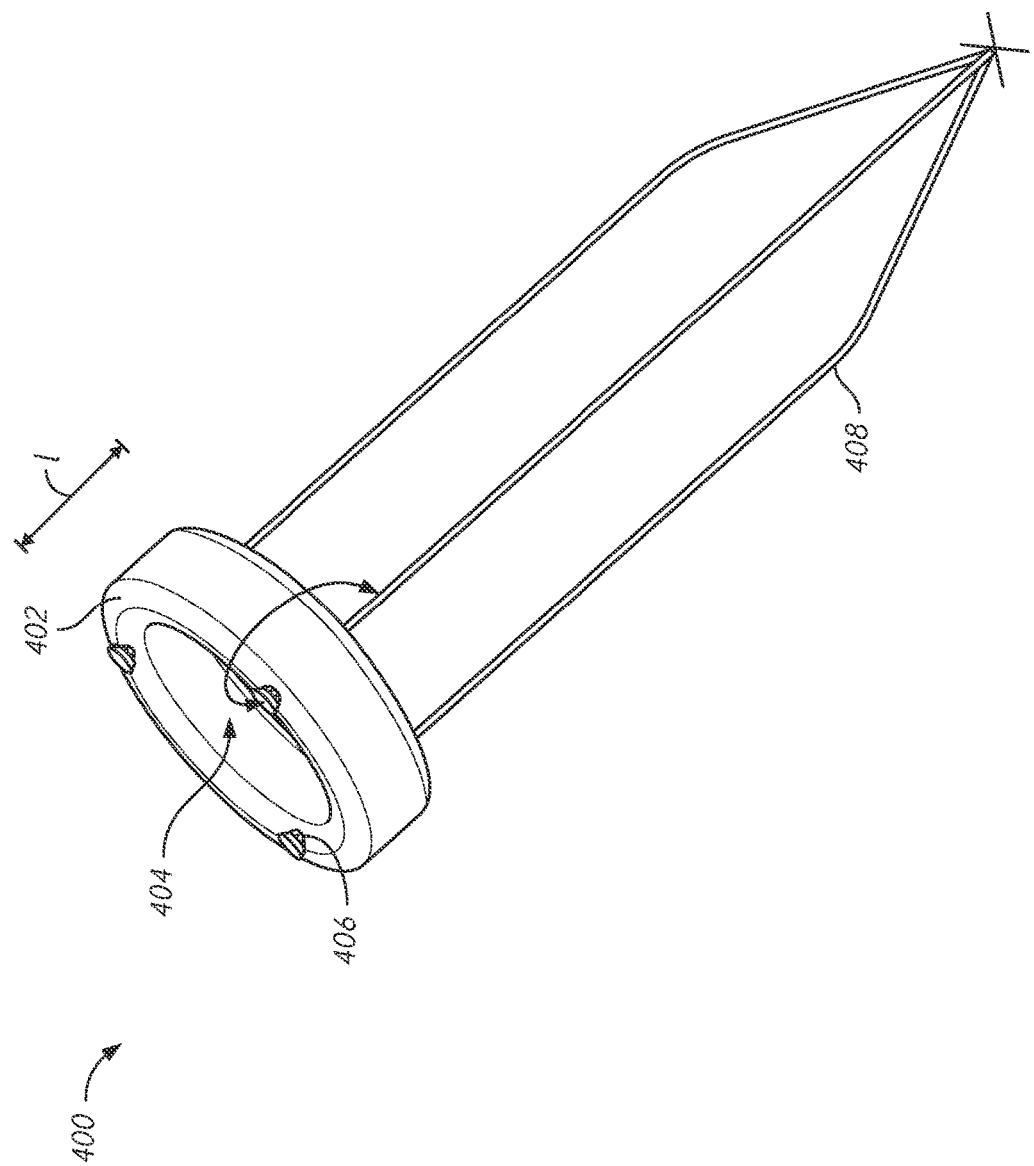
FIG. 17 illustrates an embodiment of a valve tilt and crimp ring with attached sutures.

The apertures 404 can be configured to receive and hold the ends of sutures (e.g., tethers, threads, cords, tapes) which can extend proximally through the delivery system 100, for example through lumens of various shafts. An example of the sutures 408 (in this case three sutures) attaching and extending away is shown in FIG. 17. The sutures 408 may pass through the apertures 404 and form a loop around the ring 400, or can be attached by other mechanical/adhesive methods. The second end of the sutures 408 can extend to a user, either by exiting the delivery system 100 or attaching to knobs/switches/actuators in a handle 110 of the delivery system 100. The prosthesis 70 may be located partially or fully radially within the sutures 408, proximal to the ring 400. There may be no further reattachment of the ring 400 to the delivery system 100.

Figure 18:
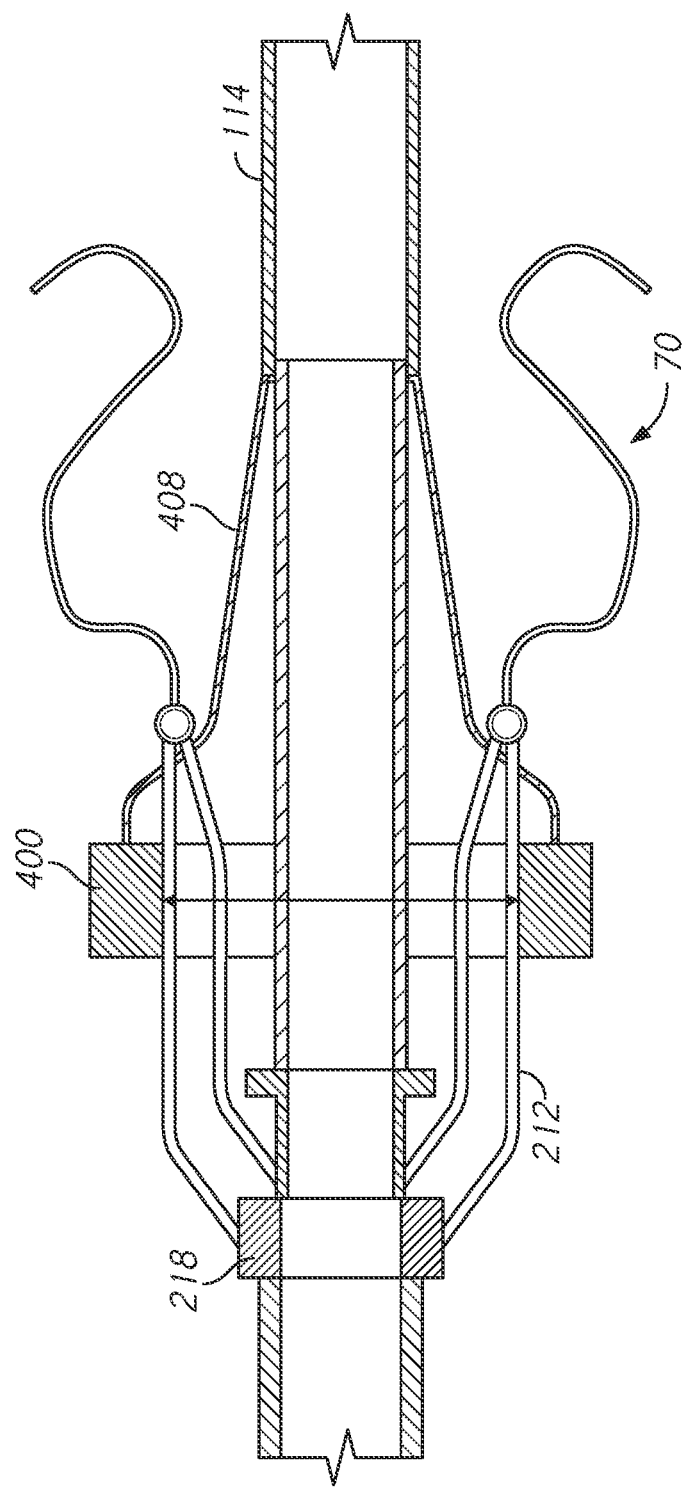
FIG. 18 illustrates an embodiment of the valve tilt and crimp ring during crimping.

When one of the sutures 408 is pulled in a proximal direction, the ring 400 can then tilt in the direction of the pull. As the sutures 212 attached to the prosthesis 70 are held within the ring 400 such as shown in FIG. 18, this force also causes tilting of the prosthesis 70. Thus, the prosthesis 70 can be moved in three-dimensional space upon expansion from the delivery system 100. Stating in another way, unequal loading of tension of the individual sutures 408 allows for tilting of the prosthesis 70 that would be useful in repositioning of the prosthesis 70 during an implantation.

Further, when the ring 400 is pulled proximally by all of the sutures 408 at the same time, the sutures 212 attached to the prostheses 70 can be compressed inwards into the lumen 404 and the first end 301 of the prosthesis 70 can be compressed to fit within the lumen 404 as shown in FIG. 18. Thus, the ring 400 can "ride along" the sutures 212, compressing them radially inwards. Further proximal pulling and motion of the ring 400 can slide along at least a portion of the prosthesis 70, and in some embodiments may slide completely proximal of the prosthesis 70. As the diameter of the lumen 404 is smaller, equal to, or slightly larger, than the diameter of the first end 301, the first end 301 can be compressed to fit within the lumen 404. This can allow the nosecone 118 to slide back over the first end 301, thereby recapturing the prosthesis 70 in the delivery system 100.

Release of Valve

The embodiments of FIGS. 19-24 illustrates steps of a method of operating the delivery system 100 and releasing an intralumenal frame assembly, such as prosthesis 70, to intralumenal tissue at an in situ target location. The steps of this method can be carried out while the prosthesis 70 is in a radially compacted state within the outer elongate hollow member shaft 114. In some embodiments, the longitudinal axis of the prosthesis 70, which runs between the first 301 and second ends 303 of the prosthesis 70, can be parallel to and/or concentric with the longitudinal axis of one or more shafts of the delivery system 100. The steps of this method can be used to transapically deliver a replacement heart valve to a mitral valve location.

Figure 19:
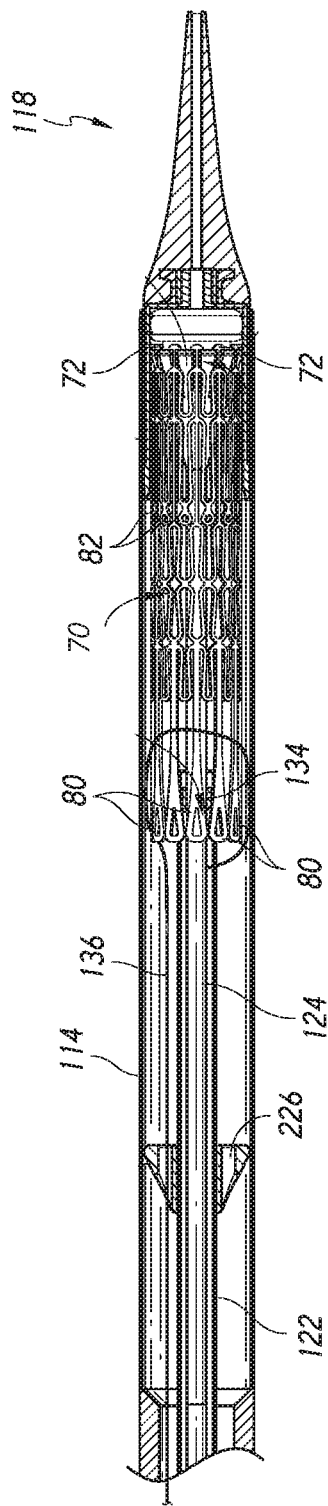
FIG. 19 illustrates a cross section of an embodiment of the delivery device.

FIG. 19 shows a cross section of the delivery system 100 with the prosthesis 70 located in the delivery position. For ease of illustration, the prosthesis 70 is shown in FIG. 19 with only its metal frame illustrated, and the suturing system discussed above has been removed. As shown, the outer elongate hollow member shaft 114 covers the prosthesis 70, thus preventing expansion of the prosthesis 70, in particular the second end 303. Further, the ventricular anchors 80 of the prosthesis 70 extend proximally toward the handle 110, with the outer elongate hollow member shaft 114 radially restraining the ventricular anchors 80 pointing proximally. The outer elongate hollow member shaft 114 extends distally to the nose cone 118, which covers the inner retention member 134. The first end 12 of the prosthesis 70 is positioned with struts 72 held with the suturing system discuss above and covered by the nose cone 118. Further, in some embodiments a tether 136 extends distally from the handle 110, within the outer elongate hollow member shaft 114, through one of the guide members 226, and is wrapped around the prosthesis 70, more preferably wrapping around the ventricular anchors 80 that extend proximally. The tether 136 then extends proximally to the tether retention member 134 located within the locking shaft 122, where the end of the tether 136 is locked in position as described above.

Figure 20:
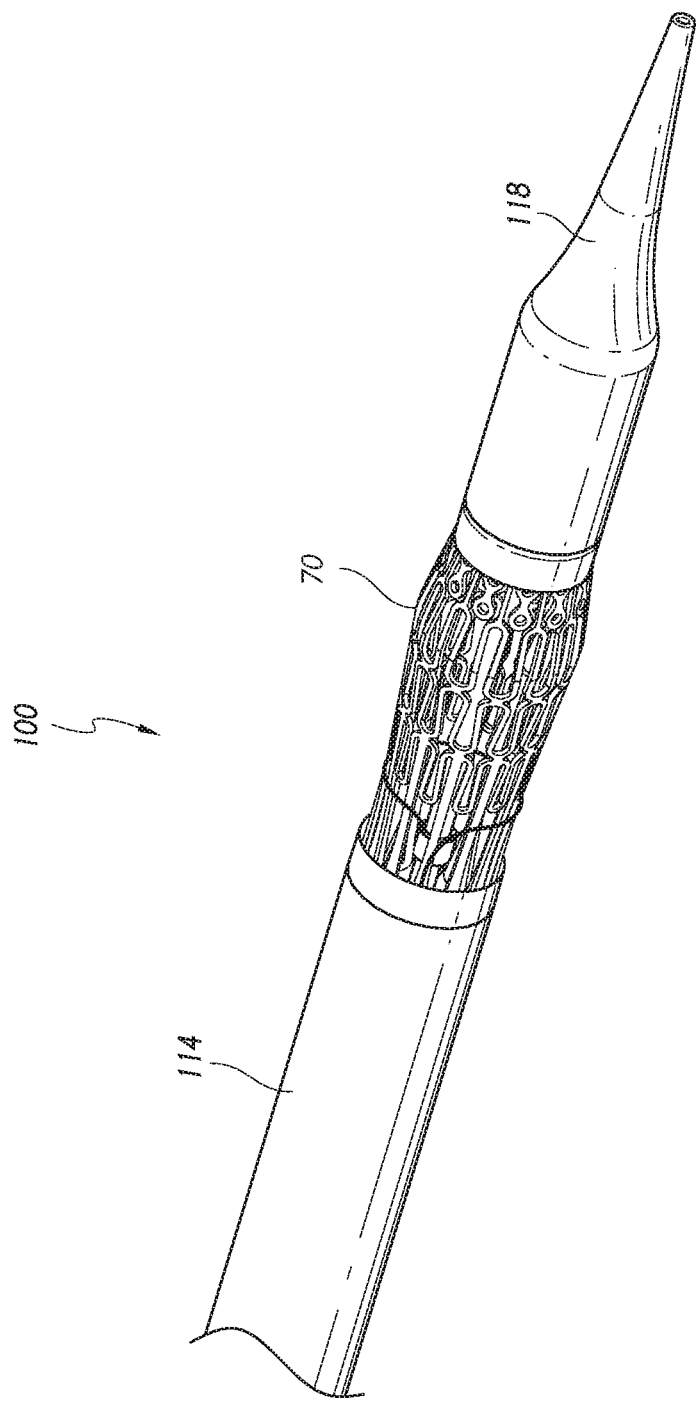
FIGS. 20-24 illustrate an embodiment of an implantation procedure of a replacement valve using the delivery device.

With reference next to the step of FIG. 20, once the delivery system 100 has positioned the prosthesis 70 at the in situ target location, the outer elongate hollow member shaft 114 can be moved relatively away from the nose cone 118, either by proximally retracting the outer elongate hollow member shaft 114 and/or distally advancing the nose cone 118 to uncover at least a portion of the prosthesis 70, in particular the second end 303 of the prosthesis 70. As shown in FIG. 20, there may be a slight bulge in the prosthesis 70 during this phase.

Figure 21:
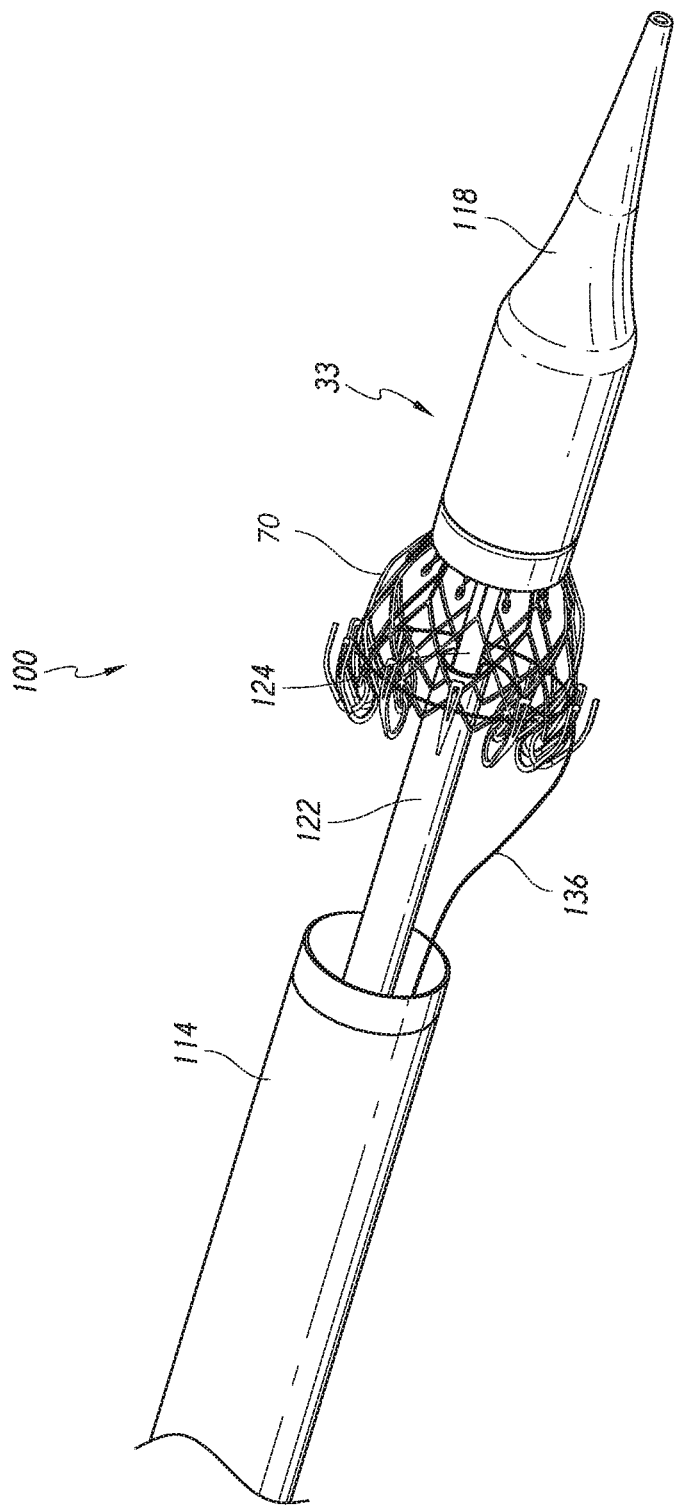

With reference next to the step of FIG. 21, the outer elongate hollow member shaft 114 can be further moved relatively away from the nose cone 118 to further uncover the prosthesis 70. As shown in the illustrated embodiment, the second end 303 of the prosthesis 70 has been uncovered with the tether 136 being the only component restraining the radial dimension of the frame of the prosthesis 70. By maintaining tension on the tether 136, the tether 136 can continue to at least partially restrain the radial dimension of the second end and can advantageously reduce the speed at which the second end radially expands. The tether 136 can be continuously released by the user at the handle 110 until the second end of the prosthesis 70 is fully expanded. In some embodiments, the tether 136 can be configured such that the first end 301 remains in the fully compacted state when the second end 303 is fully uncovered.

It should be noted that the first end 301 of the prosthesis 70 can remain covered by the nose cone 118 during this step such that the first end 301 remains in a radially compacted state. Moreover, as shown in the illustrated embodiment, the second end 303 of the prosthesis 70 has at least partially expanded in the radial dimension with the ventricular anchors 80 having been flipped to extend distally away from the second end of the prosthesis 70 (and distally away from the handle 110). By controlling the expansion of the second end 303 of the prosthesis 70 with the tether 136, the user can minimize the risk of the ventricular anchors 80 catching on surrounding tissue when the ventricular anchors 80 flip from extending proximally to extending distally.

Figure 22:
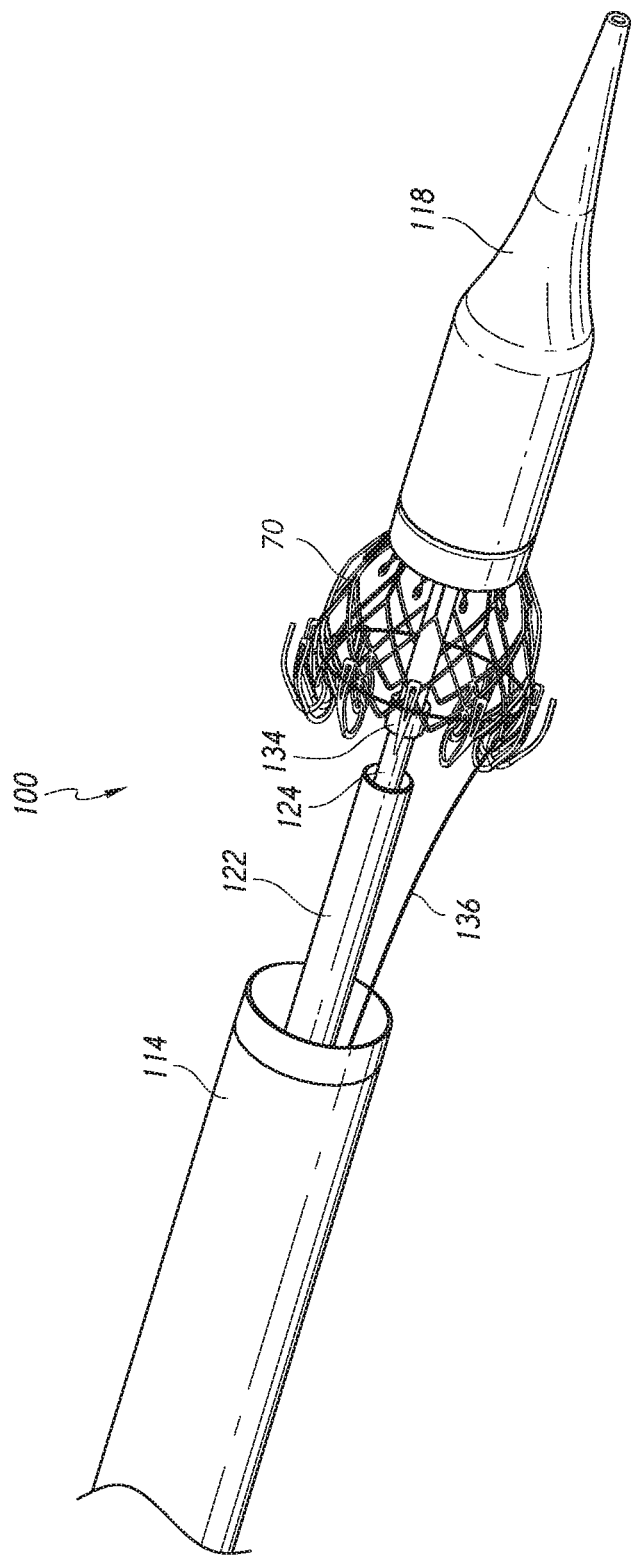

As shown in FIG. 22, once the second end 303 of the prosthesis 70 is fully expanded, the locking shaft 122 can be moved relatively proximally to expose the tether retention member 134, thus allowing the tether 136 to fully release from the tether retention member 134.

Figure 23:
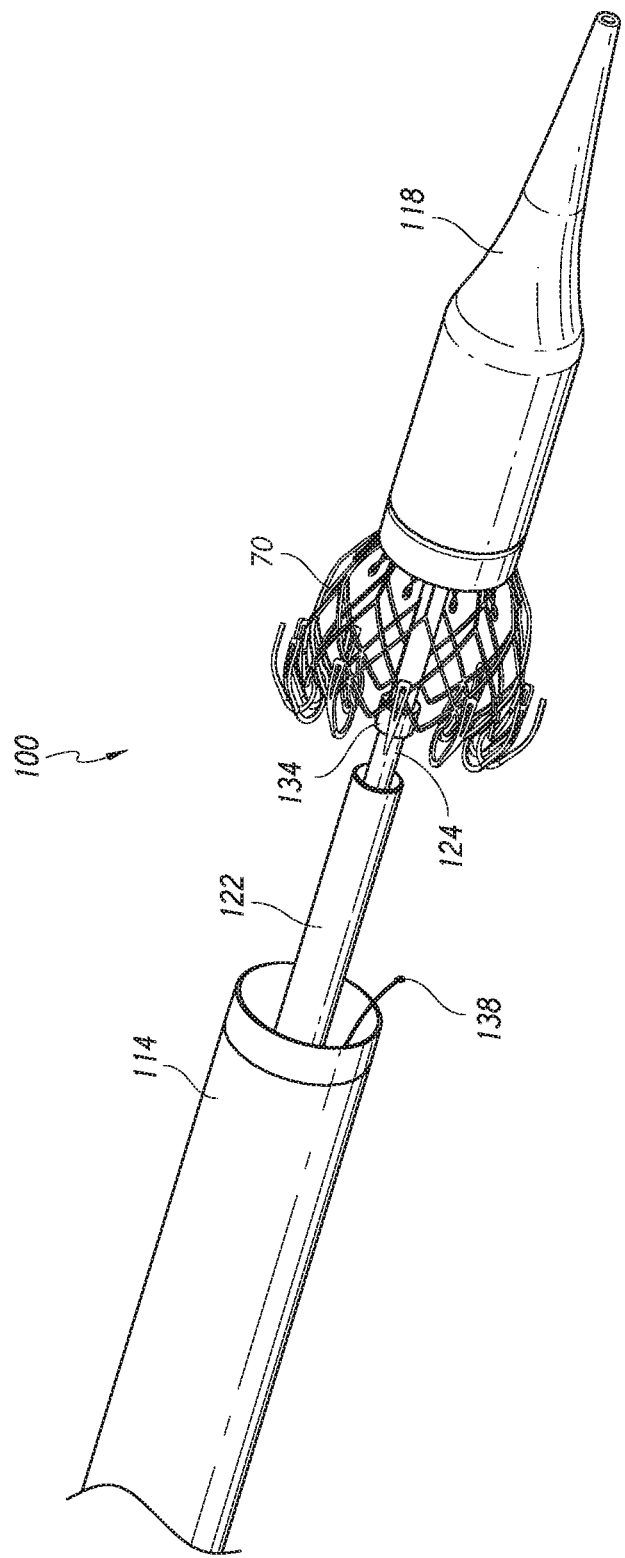

Next, as shown in FIG. 23, the tether retention member 134 has released the end 138 of the tether 136. It should be noted that the first end 301 of the prosthesis 70 can remain covered by the nose cone 118 during this step such that the first end 301 remains in a radially compacted state. As discussed below, the tether 136 and end 138 can be retracted proximally into the delivery system 100 at this point. In some embodiments, the tether 136 and the locking shaft 122 are not used.

Figure 24:
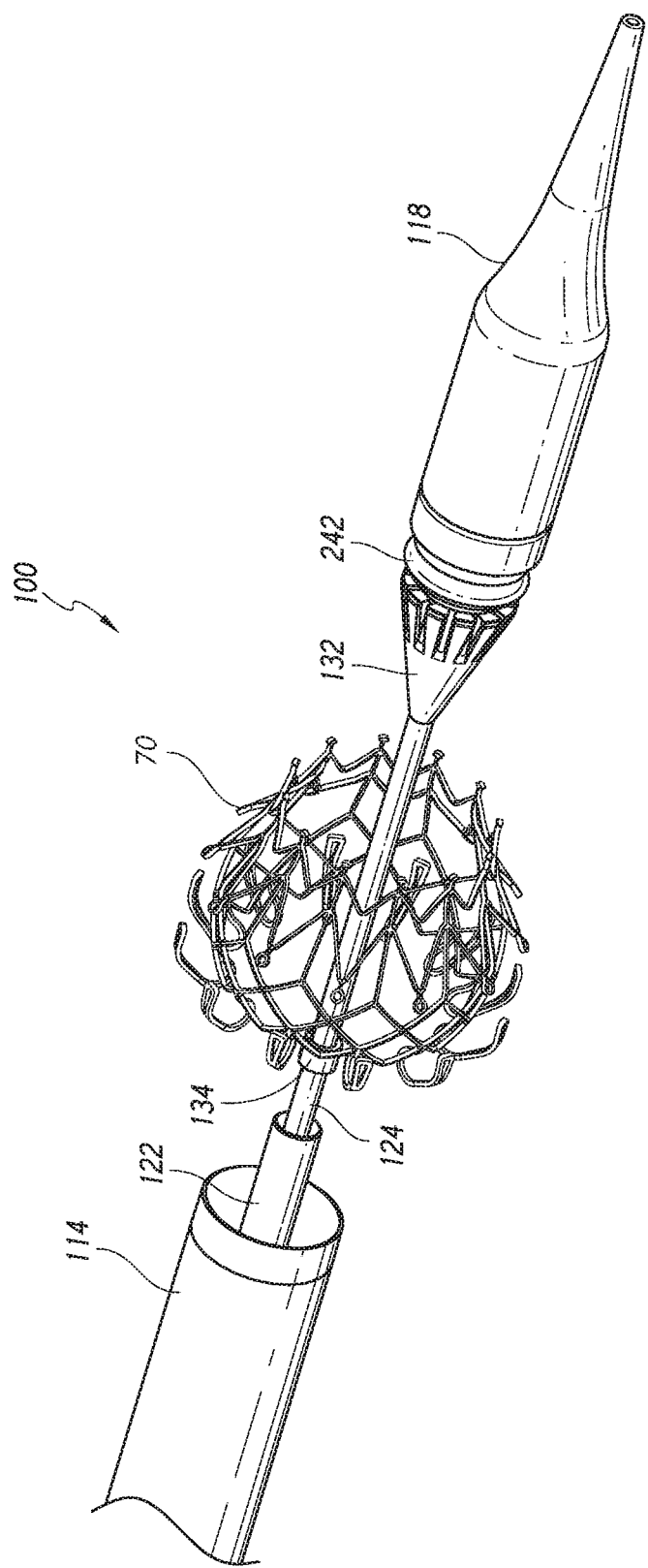

With reference next to the step of FIG. 24, the suture retention mechanism, such as manifold 204, discussed in detail above can be moved relatively away from the nose cone 118 such that the first end of the prosthesis 70 can radially expand to its fully expanded configuration. This can be achieved by either distally moving the nose cone 118 relative to the manifold 204 and/or moving the manifold 204 proximally relative to the nose cone 118. As discussed, the prosthesis 70 can remain attached to the delivery system 100 in the fully expanded state until the sutures are release as discussed above.

After expansion and release of the prosthesis 70, the different distal end attachment components and the nose cone 118 can be withdrawn through the center of the prosthesis 70 and into the outer elongate hollow member shaft 114.

The delivery device 100 may be provided to users with an prosthesis 70 preinstalled, such as illustrated in FIG. 19. In other embodiments, the prosthesis 70 can be loaded onto the delivery device 100 shortly before use, such as by a physician or nurse.

Further discussion on the release of the valve are described in U.S. Pat. Pub. No. 2017/0056169, hereby incorporated by reference in its entirety.

Insertion Methodology

Figure 25:
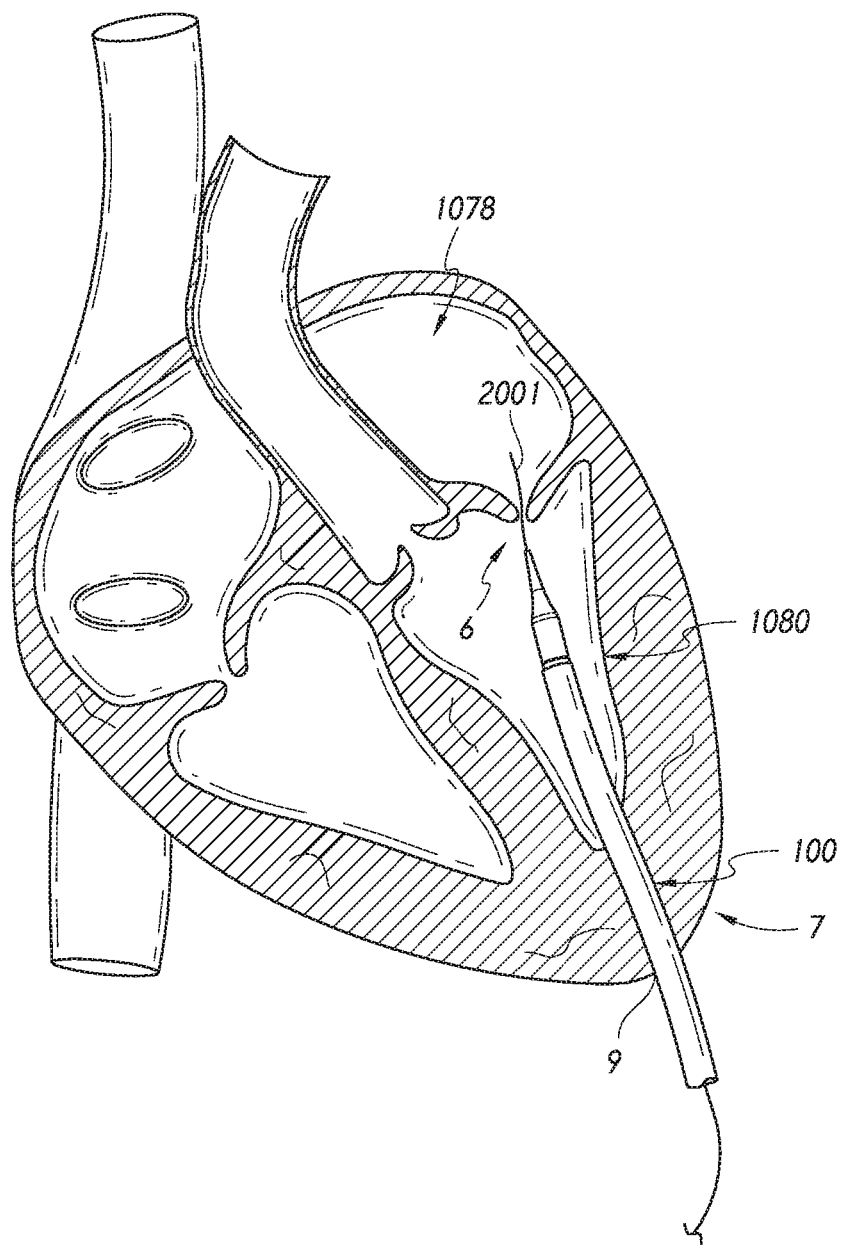
FIG. 25 illustrates a transapical approach for a delivery device.
Figure 26:
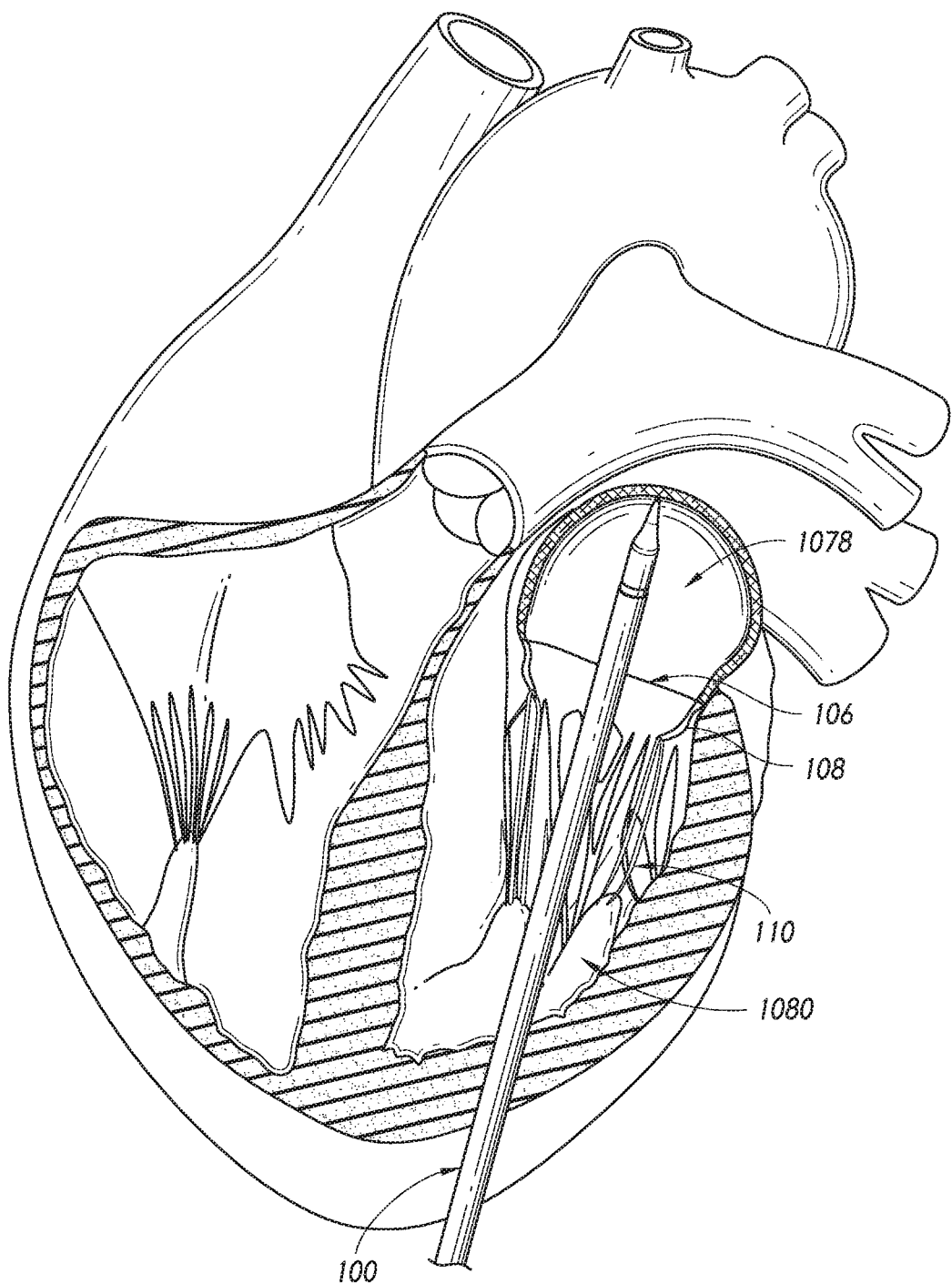
FIGS. 26-28B illustrate steps of a transapical method for delivery of a valve prosthesis to replace a mitral valve.

FIG. 25 illustrates a transapical approach for use with the delivery device 100. As shown, the delivery device 100 can access a mitral valve through the apex 7 of the heart. As depicted in FIG. 25, a guide wire 2001 is advanced into the left ventricle 6 of the heart through a puncture or opening 9 near the apex 7. The heart may be accessed through a limited thoracotomy, small trocar puncture, or small catheter puncture. With the guide wire 2001 in place, the physician can insert the device 100 to the left ventricle 6 and deploy the heart valve as disclosed above. In some embodiments, a guide wire is not used. A balloon can be inserted into the left atrium 1078 and expanded to confirm that the guide wire 2001 has not been advanced through any of the chordae 110 or papillary muscles.

In some embodiments, the prosthesis 70 can be delivered under fluoroscopy so that a user can view certain reference points for proper positioning of the prosthesis 70. Further, echocardiography can be used for proper positioning of the prosthesis 70.

FIGS. 26-28B show different steps of embodiments of a method of delivering the prosthesis 70 to the proper position in the heart.

Prior to insertion of the delivery system 100, the access site into the patient can be dilated. Further, a dilator can be flushed with, for example, heparinized saline prior to use. The delivery system 100 can then be inserted over a guide wire 2001.

The delivery system 100 can be advanced until a distal end of the delivery system 100 through the left ventricle 1070 and mitral annulus 106 into the left atrium 1078. Thus, the distal end of the delivery system 100 can be located in the left atrium 1078. In some embodiments, the delivery system 100 can be rotated, such as under fluoroscopy, into a desired position. The position of the delivery system 100, and the prosthesis 70 inside, can be verified using echocardiography and fluoroscopic guidance.

In some embodiments, the prosthesis 70 can be located, prior to release, above the mitral annulus 106, in line with the mitral annulus 106, just below the mitral annulus 106, or below the mitral annulus 106. In some embodiments, the prosthesis 70 can be located, prior to expansion, fully above the mitral annulus 106, in line with the mitral annulus 106, just below the mitral annulus 106, or fully below the mitral annulus 106. In some embodiments, the prosthesis 70 can be located, prior to expansion, partially above the mitral annulus 106, in line with the mitral annulus 106, or partially below the mitral annulus 106.

In some embodiments, the position of the mitral plane and the height of any papillary muscles 2004 on the fluoroscopy monitor can be marked to indicate an example target landing zone.

Further, the delivery system 100 can be positioned to be coaxial to the mitral annulus 106, or at least as much as possible, while still reducing contact with the left ventricular wall, the left atrial wall, and/or the mitral annulus 106 and reducing delivery system tension. An echo probe can be position to view the anterior mitral leaflet (AML), the posterior mitral leaflet (PML) (leaflets 108), mitral annulus 106, and outflow tract. Using fluoroscopy and echo imaging, the prosthesis 70 can be confirmed to be positioned at a particular depth and coaxiality with the mitral annulus 106.

Afterwards the prosthesis 70 is aligned to be generally perpendicular to the mitral annulus 106, the elongate hollow member shaft 114 can be retracted to expose the left ventricular anchors 80. In some embodiments, once exposed, the elongate hollow member shaft 114 can be reversed in direction to relieve tension on the elongate hollow member shaft 114. The tether 136 can keep the prosthesis 70 from quickly expanding.

Figure 27A:
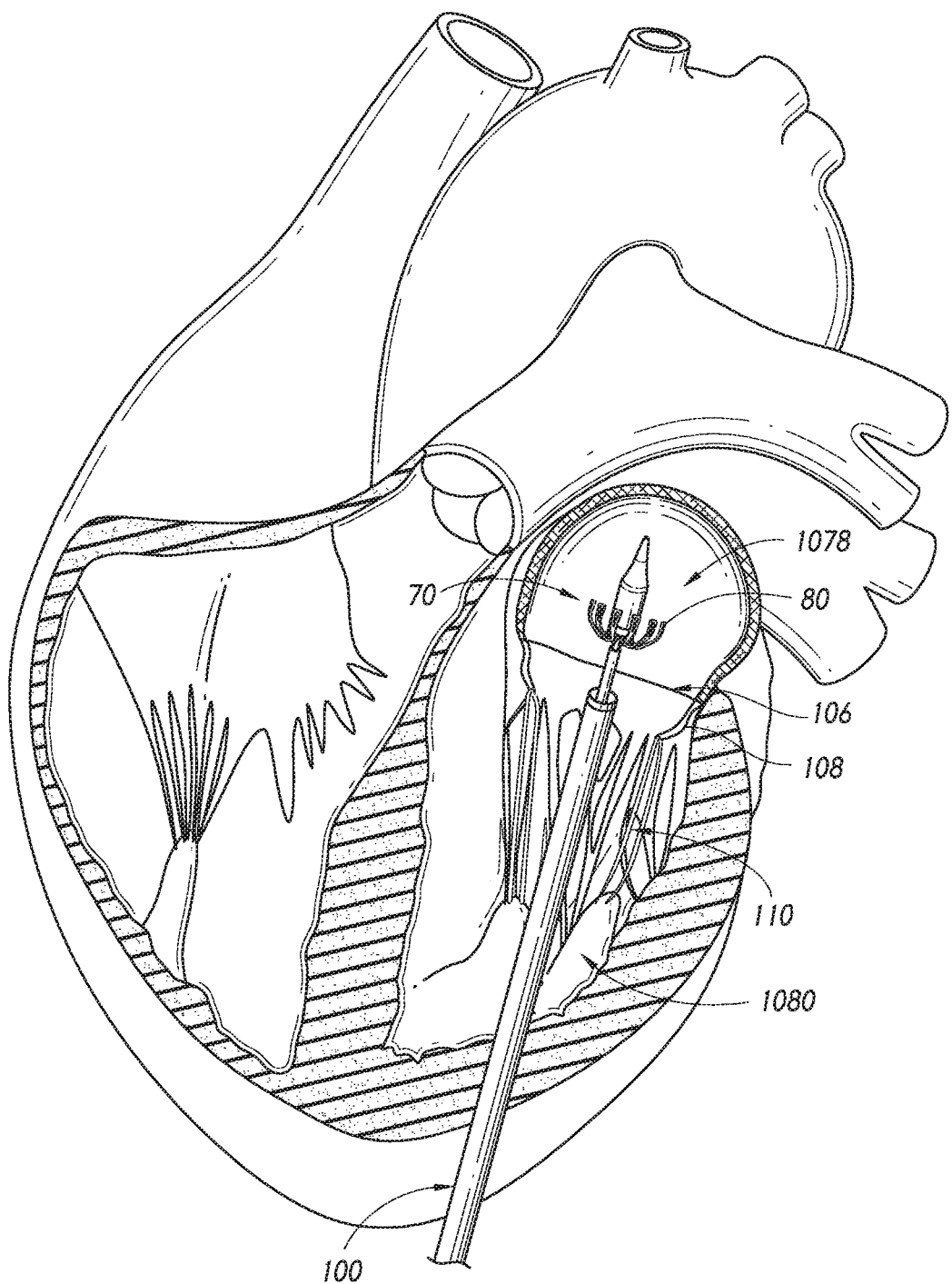

An embodiment of the position of the delivery system 100 for release of the ventricular anchors 80 is shown in FIG. 27A. As shown, the ventricular anchors 80 can be released in the left atrium 1078, such as by proximal movement of the outer elongate hollow member shaft 114. In some embodiments, only the ventricular anchors 80 are released from the delivery system 100. In some embodiments, the ventricular end of the prosthesis 70 does not expand with released of the ventricular anchors 80. However, in some embodiments, one or more of the ventricular anchors 80 can be released in either the left atrium 1078 (e.g., super-annular release), generally aligned with the mitral valve annulus 106 (e.g., intra-annular release), or just below the mitral valve annulus 106 (e.g., sub-annular release). In some embodiments, all of the ventricular anchors 80 can be released together. In other embodiments, a subset of the ventricular anchors 80 can be released while at a first position and another subset of the ventricular anchors 80 can be released while at a second position.

As discussed in detail above, upon release from the delivery system 100, the ventricular anchors 80 can flip from extending distally to extending proximally. Accordingly, in some embodiments, the ventricular anchors 80 can be flipped in either the left atrium 1078 (e.g., super-annular flip), generally aligned with the mitral valve annulus 106 (e.g., intra-annular flip), or below the mitral valve annulus 106 (e.g., sub-annular flip). The ventricular anchors 80 can be released and flipped in the left atrium 1078 (or generally aligned with the mitral valve annulus 106) or in the left ventricle 1080. The atrial anchors 82 can remain within the delivery system 100. In some embodiments, all of the ventricular anchors 80 can be flipped together. In other embodiments, a subset of the ventricular anchors 80 can be flipped while at a first position and another subset of the ventricular anchors 80 can be released while at a second position. For example, some of the ventricular anchors 80 can be flipped in the left atrium 1078 and some of the ventricular anchors 80 can be flipped while generally aligned with the mitral valve annulus 106 or just below the mitral valve annulus 106.

In some embodiments, the ventricular anchors 80 may be positioned in line with the annulus 106 in the non-flipped position. In some embodiments, the ventricular anchors 80 may be position in line with the annulus 106 in the flipped position. In some embodiments, the ventricular anchors 80 may be just below the annulus 106 in the non-flipped position. In some embodiments, the ventricular anchors 80 may be just below the annulus 106 in the flipped position. In some embodiments, prior to flipping the ventricular side of the prosthesis 70 can be located within or below the mitral valve annulus 106. However, flipping the anchors can cause, without any other movement of the delivery system 100, the ventricular side of the prosthesis 70/anchors 80 to move upwards, moving it into the left atrium 1078 or moving it in line with the mitral annulus 106. Thus, in some embodiments the ventricular anchors 80 can begin flipping at the annulus 106 but be fully within the left atrium 1078 upon flipping. In some embodiments the ventricular anchors 80 can begin flipping below the annulus 106 but be generally in line with the annulus 106 upon flipping.

In some embodiments, the ventricular anchors 80 can be distal (e.g., toward the left atrium 1078) of a free edge of the mitral leaflets 108 upon release and flipping. In some embodiments, the ventricular anchors 80 can be aligned with (e.g., toward the left atrium 1078) a free edge of the mitral leaflets 108 upon release and flipping. In some embodiments, the ventricular anchors 80 can be distal (e.g., toward the left atrium 1078) of a free edge of the mitral valve annulus 106 upon release and flipping. In some embodiments, the ventricular anchors 80 can be aligned with (e.g., toward the left atrium 1078) a free edge of the mitral valve annulus 106 upon release and flipping. In some embodiments, the ventricular anchors 80 can be proximal (e.g., toward the left ventricle 1080) of a free edge of the mitral leaflets 108 upon release and flipping.

Thus, in some embodiments the ventricular anchors 80 can be released/flipped above where the chordae 110 attach to the free edge of the native leaflets 108. In some embodiments the ventricular anchors 80 can be released/flipped above where some the chordae 110 attach to the free edge of the native leaflets 108. In some embodiments the ventricular anchors 80 can be released/flipped above where all the chordae 110 attach to the free edge of the native leaflets 108. In some embodiments, the ventricular anchors 80 can be released/flipped above the mitral valve annulus 106. In some embodiments, the ventricular anchors 80 can be released/flipped above the mitral valve leaflets 108. In some embodiments, the ventricular anchors 80 can be released/flipped generally in line with the mitral valve annulus 106. In some embodiments, the ventricular anchors 80 can be released/flipped generally in line with the mitral valve leaflets 108. In some embodiments, the tips of the ventricular anchors 80 can be released/flipped generally in line with the mitral valve annulus 106. In some embodiments, the tips of the ventricular anchors 80 can be released/flipped generally in line with the mitral valve leaflets 108. In some embodiments the ventricular anchors 80 can be released/flipped below where some the chordae 110 attach to the free edge of the native leaflets 108. In some embodiments the ventricular anchors 80 can be released/flipped below where all the chordae 110 attach to the free edge of the native leaflets 108. In some embodiments, the ventricular anchors 80 can be released/flipped below the mitral valve annulus 106. In some embodiments, the ventricular anchors 80 can be released/flipped below the mitral valve leaflets 108.

Figure 27B:
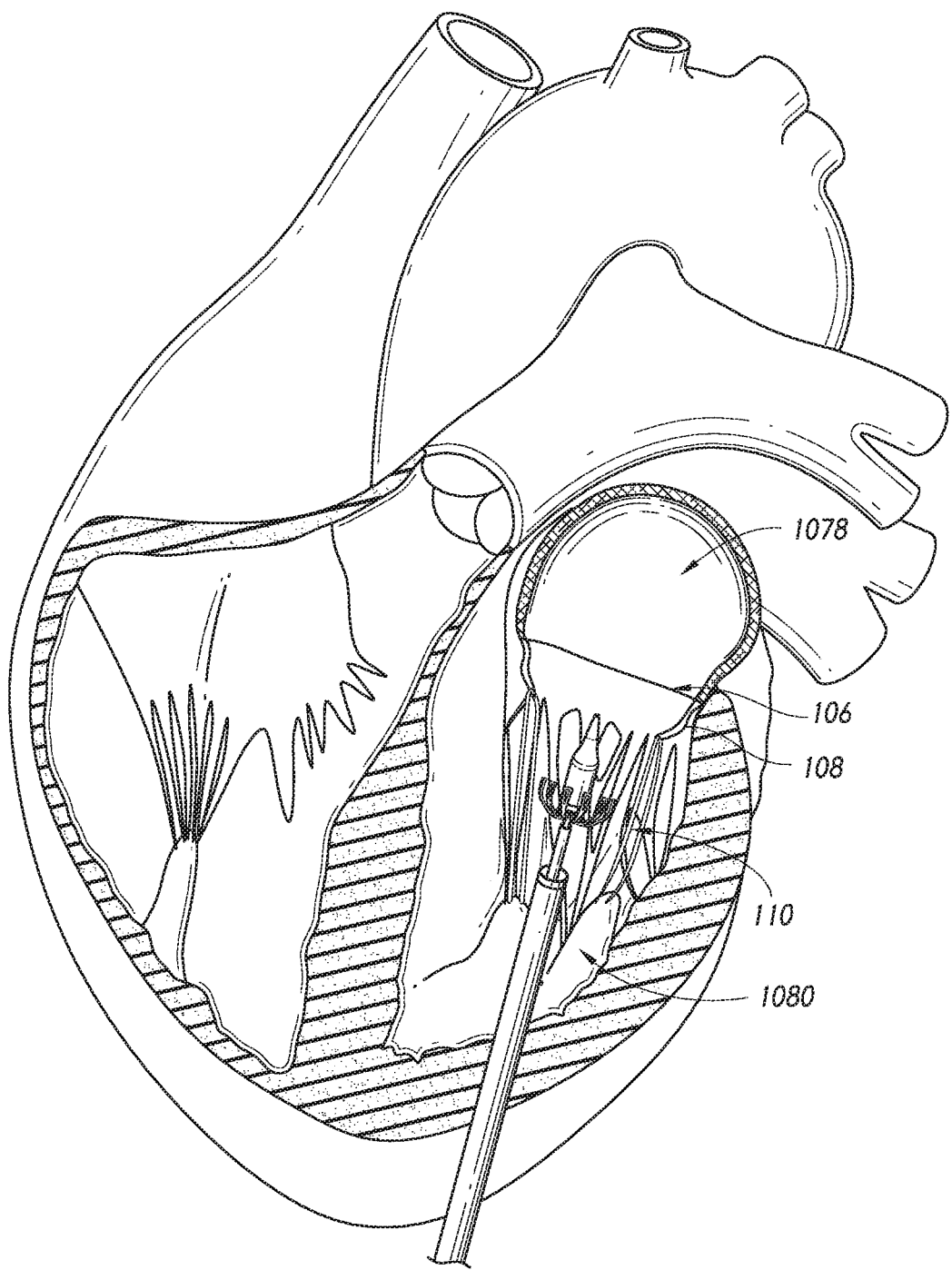

Once the ventricular anchors 80 are released and flipped, the delivery system 100 can be translated back towards the left ventricle 1080 through the mitral valve annulus 106 so that the ventricular anchors 80 enter the left ventricle 1080 as shown in FIG. 27B. In some embodiments, the ventricular anchors 80 compress when passing through the mitral valve annulus 106. In some embodiments, the prosthesis 70 can compress when passing through the mitral valve annulus 106. In some embodiments, the prosthesis 70 does not compress when it passes through the mitral annulus 106. The system 100 can be released anywhere within the left ventricle 1080 between the papillary heads and the leaflets 108.

In some embodiments, the ventricular anchors 80 are fully expanded prior to passing through the mitral valve annulus 106, such as the tether 136 being fully released. In some embodiments, the ventricular anchors 80 are partially expanded prior to passing through the mitral valve annulus 106, such as the tether 136 maintaining tension, and continued operation of the delivery system 100 can fully expand the ventricular anchors 80 in the left ventricle 1080.

When the ventricular anchors 80 enter the left ventricle 1080, the ventricular anchors 80 can pass through the chordae 110 and move behind the mitral valve leaflets 108, thereby capturing the leaflets 108. In some embodiments, the ventricular anchors 80 and/or other parts of the prosthesis 70 can push the chordae 110 and/or the mitral valve leaflets 108 outwards.

Thus, after release of the ventricular anchors 80, the delivery system 100 can then be repositioned as needed so that the ends of the left ventricular anchors 80 are at the same level of the free edge of the native mitral valve leaflets as shown in FIG. 27B. The delivery system 100 can also be positioned to be coaxial to the mitral annulus 106 if possible while still reducing contact with the left ventricular wall, the left atrial wall, and/or the annulus 106.

Figure 27C:
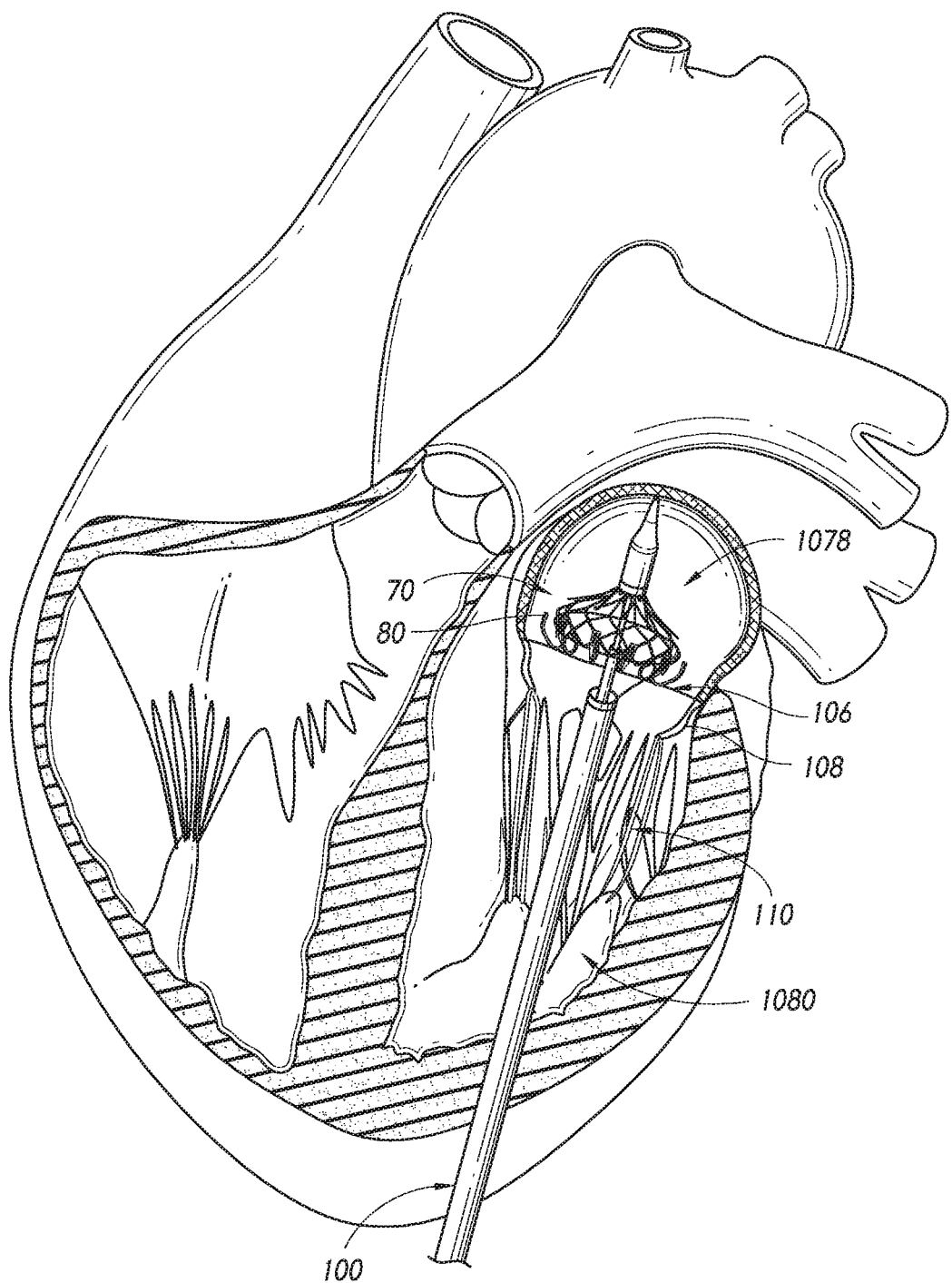
Figure 27D:
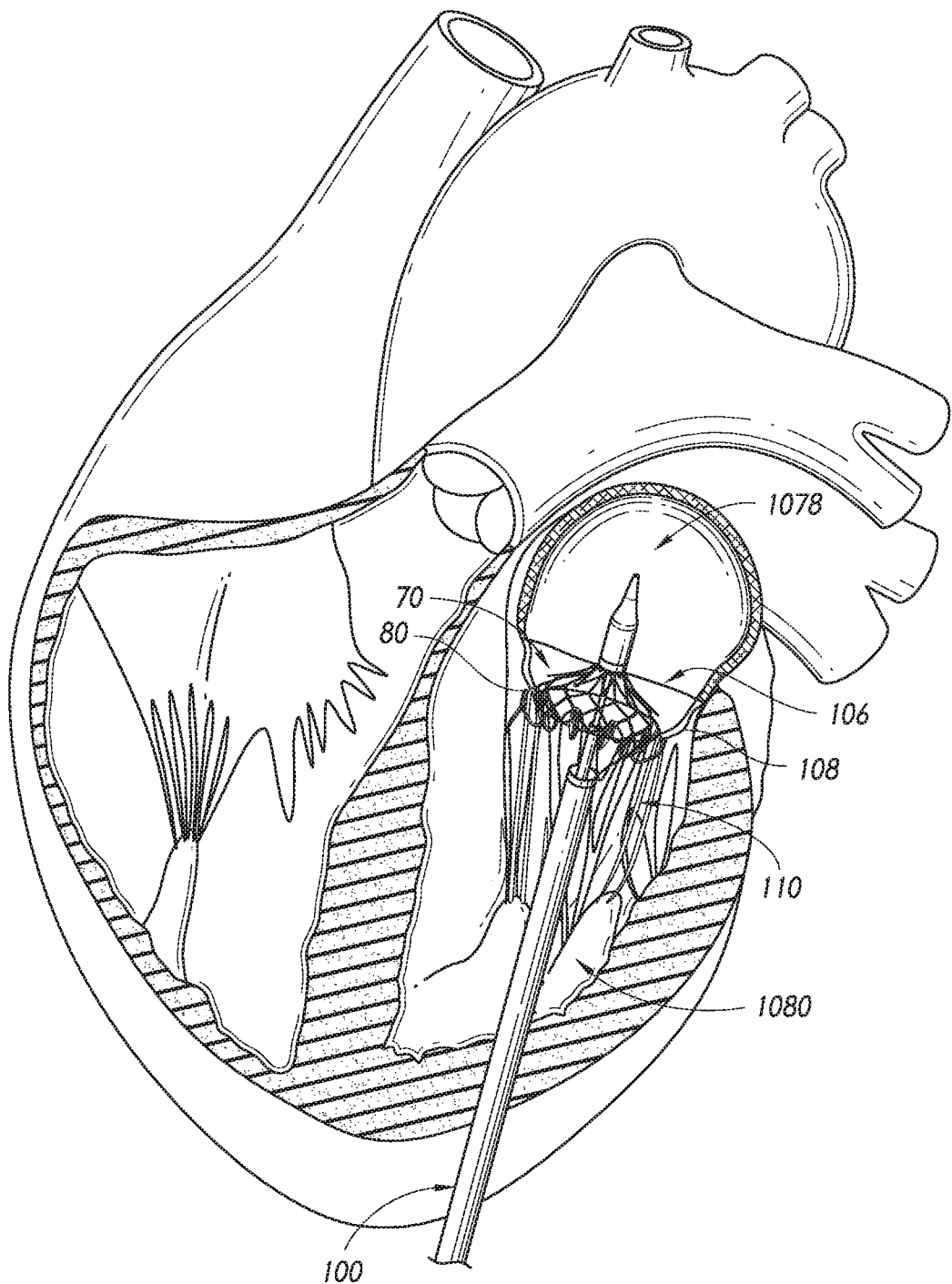

As shown above, in some embodiments, only the ventricular anchors 80 are released in the left atrium 1078 before the prosthesis 1010 is move to a position within, or below, the annulus. In some alternate embodiments, the distal end of the prosthesis 70 can be further expanded in the left atrium 1078, as shown in FIG. 27C. Thus, instead of the ventricular anchors 80 flipping and no portion of the prosthesis 70 body expanding, a portion of the prosthesis 70 can be exposed and allowed to expand in the left atrium 1078. This partially exposed prosthesis 70 can then be passed through the annulus 106 into the left ventricle 1080, such as shown in FIG. 27D. Further, the atrial anchors 82 can be exposed. This is an alternative methodology as compared to FIGS. 27A-B. In some embodiments, the entirety of the prosthesis 70 can be expanded within the left atrium 1078.

To facilitate passage through the annulus 106, the delivery system 100 can include a leader element (not shown) which passes through the annulus 106 prior to the prosthesis 10 passing through the annulus 106. For example, the leader element can include an expandable member, such as an expandable balloon, which can help maintain the shape, or expand, the annulus 106. The leader element can have a tapered or rounded shape (e.g., conical, frustoconical, semi-spherical) to facilitate positioning through and expansion of the annulus 106. In some embodiments, the delivery system 100 can include an engagement element (not shown) which can apply a force on the prosthesis 70 to force the prosthesis 70 through the annulus 106. For example, the engagement element can include an expandable member, such as an expandable balloon, positioned within or above the prosthesis 70. In some embodiments, the engagement element can include one or more tethers.

However, if only the ventricular anchors 80 are flipped, and no other expansion occurs such as shown in FIGS. 27A-B, the expansion shown in FIG. 27C can be skipped and the prosthesis can instead be partially expanded in the ventricle 1080 to the position shown in FIG. 27D. Thus, when the prosthesis 70 is in the proper location, the distal end can be allowed to expand to capture the leaflets 108. If the distal end is already expanded, such as from FIG. 27C, no more expansion may take place or the distal end can be further expanded.

Figure 27E:
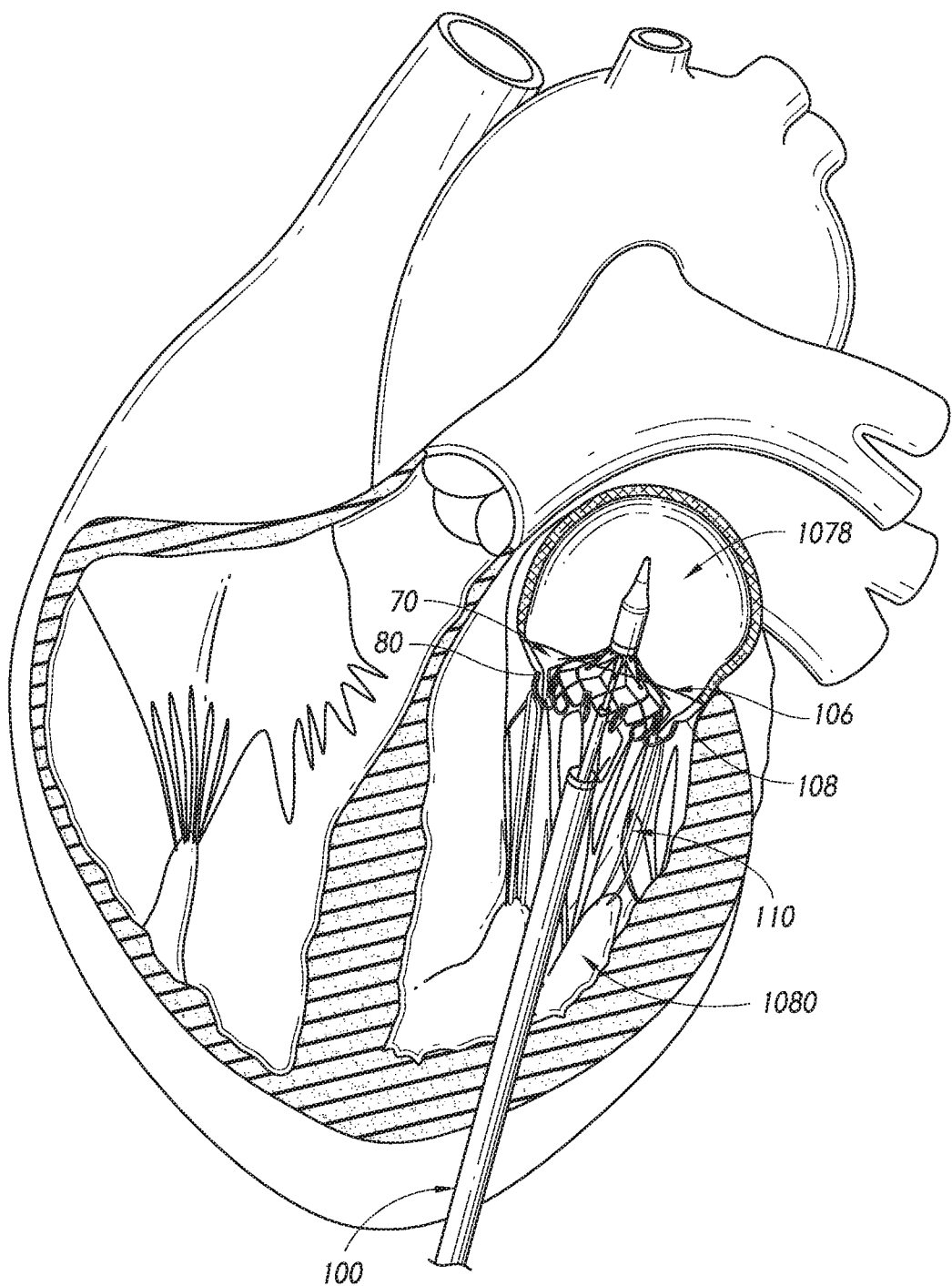

Further, the PML and AML 108 can be captured, for example by adjusting the depth and angle of the prosthesis 70. FIG. 27E shows the position of the prosthesis 70 after capturing the leaflets 108. If a larger prosthesis diameter is needed to capture the leaflets 108, the elongate hollow member shaft 114 can be retracted until the desired diameter of the prosthesis 70 is achieved. Capture of the leaflets 108 can be confirmed through echo imaging. In some embodiments, a user can confirm that the prosthesis 70 is still in the appropriate depth and has not advanced into the left ventricle 1080. The position can be adjusted as needed.

In some embodiments, once the ventricular anchors 80 enter the left ventricle 1080 the system 100 can be pushed upwards (e.g., towards the left atrium 1078) to fully capture the leaflets 108 as shown in FIG. 27E. In some embodiments, the system 100 does not need to be pulled backwards to capture the leaflets 108. In some embodiments, systolic pressure can push the leaflets 108 upwards to be captured by the ventricular anchors 80. In some embodiments, a user can rotate the delivery system 100 and/or prosthesis 1010 prior to and/or while pulling the delivery system 100 backwards. In some instances, this can beneficially engage a greater number of chordae tendineae.

The delivery system 100 can be maneuvered to be coaxial and height relative to the mitral annulus 106, such as by translating or rotating the delivery system 100. As needed, the prosthesis 70 can be repositioned to capture the free edge of the native mitral valve leaflets 108. Once full engagement of the leaflets 108 is confirmed, the prosthesis 70 can be set perpendicular (or generally perpendicular) to the mitral annular plane. The tether 136 can continue to be released to continue expansion of the prosthesis 70.

Figure 27F:
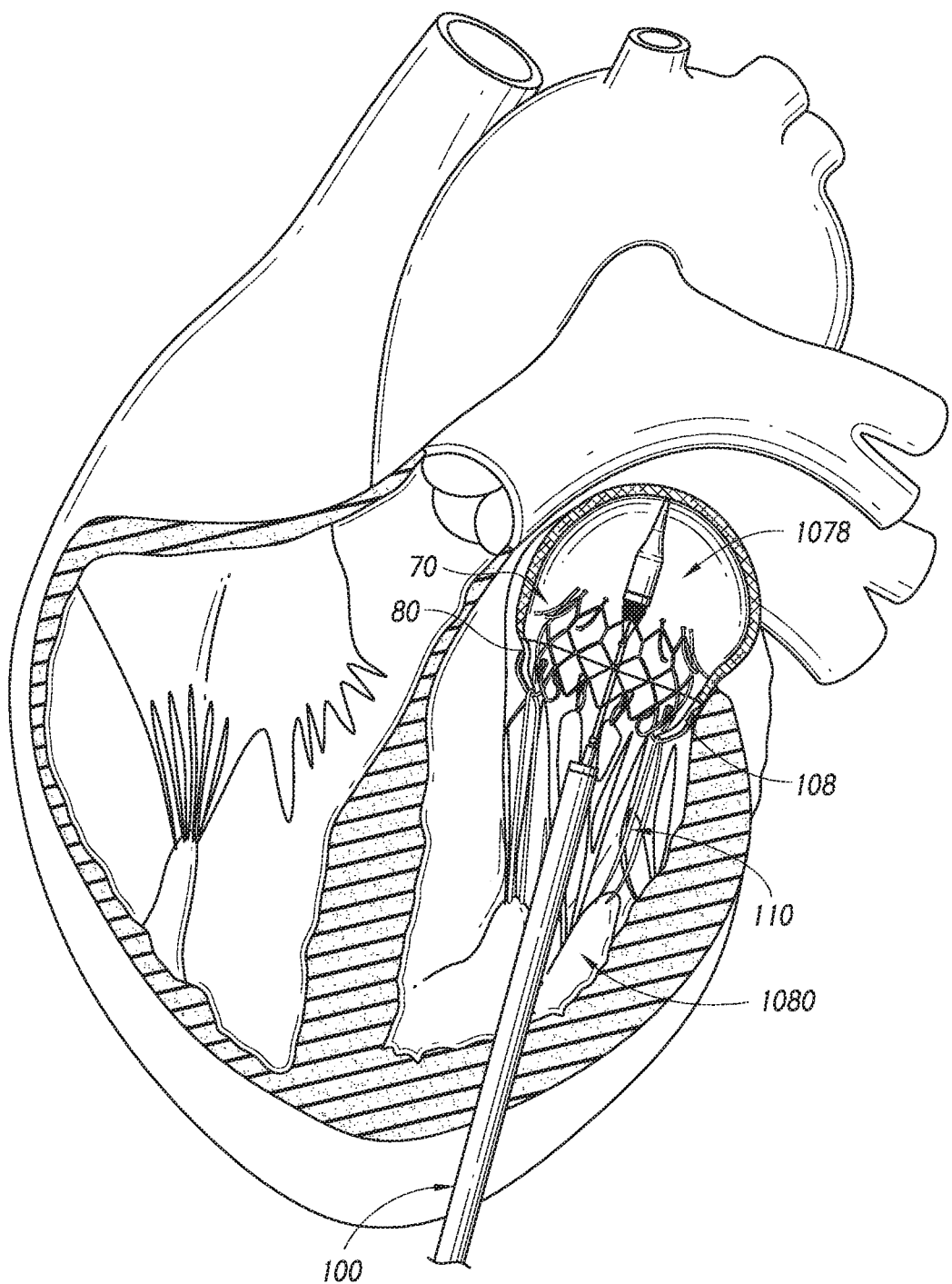

Following, the nose cone 118 can be advanced distally until the first end 301 of the prosthesis 70 and the left atrial anchors 82 are exposed and the prosthesis 70 expanded as shown in FIG. 27F. The nose cone 118 can then be reversed in direction to relieve any tension on the delivery system 100. As discussed in detail above, the prosthesis 70 may still be connected to the delivery system 100 through the tether configuration. If the prosthesis 70 is determined to be in the correct position, the tethers can be released and the prosthesis 70 can be released from the delivery system 100.

In some embodiments, atrial anchors 82 may not be released from the system 10 until the ventricular anchors 80 have captured the leaflets 108. In some embodiments, atrial anchors 82 may be released from the system 10 prior to the ventricular anchors 80 capturing the leaflets 108. In some embodiments, the atrial anchors 82 can be released when the ventricular anchors 80 are super or intra annular and the expanded prosthesis 70 (either partially or fully expanded) can be translated through the mitral annulus 106.

After, the leaflet capture and positioning of the prosthesis 70 can be confirmed, along with the relatively perpendicular position with respect to the mitral annular plane. Proper positioning of the prosthesis 70 can be confirmed using TEE and fluoroscopic imaging.

Following, the delivery system 100 can be centralized within the prosthesis 70. The nose cone 118 can be translated to be flush with the outer elongate hollow member shaft 114. The delivery system 100 can then be retracted into the left atrium 1078 and removed.

This intra-super annulus release can have a number of advantageous. For example, this allows the ventricular anchors 80 to be properly aligned when contacting the chordae 110. If the ventricular anchors 80 were released in the left ventricle 1080, this could cause misalignment or damage to heart tissue, such as the leaflets 108 or chordae 110.

Figure 28A:
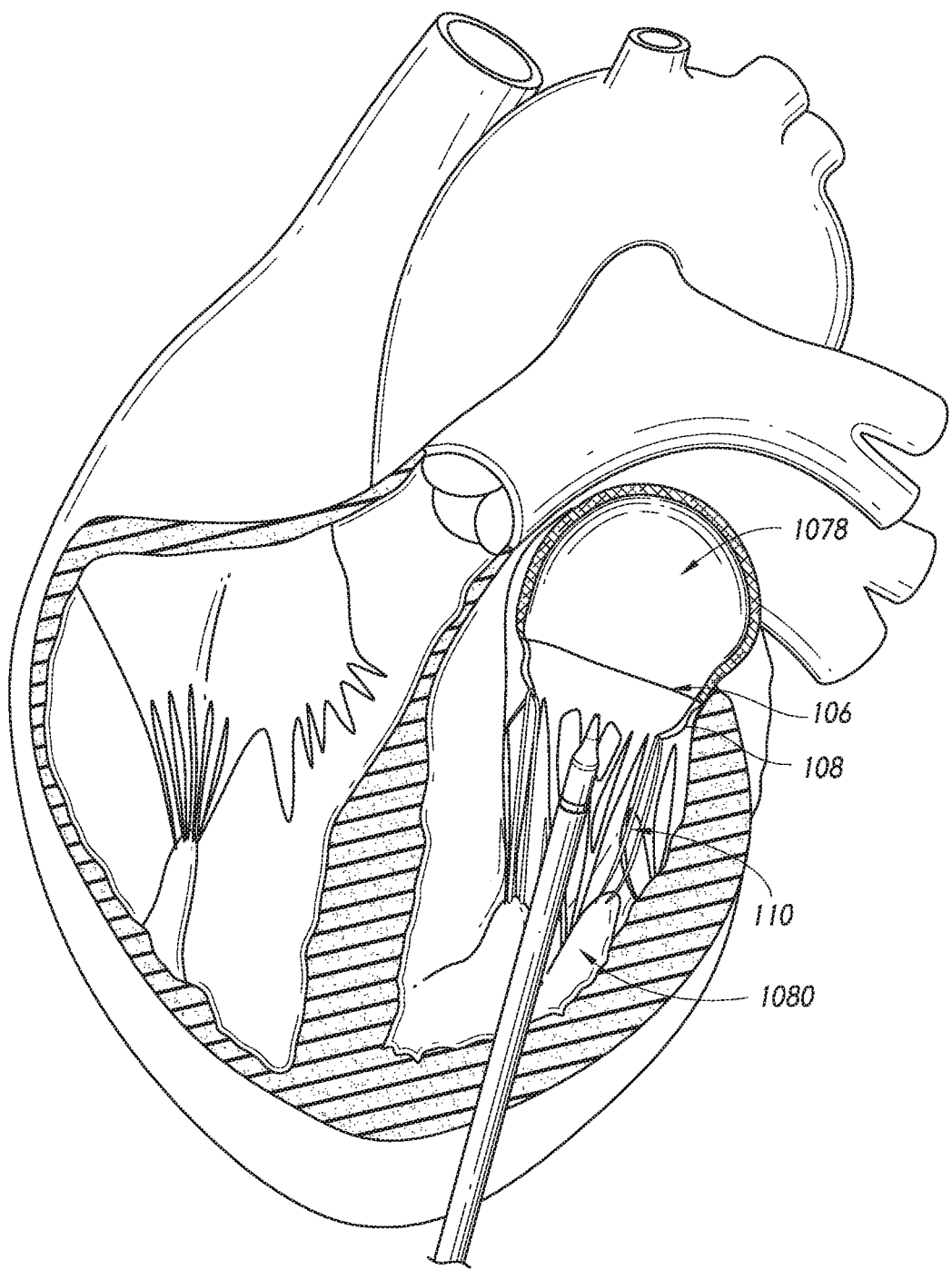
Figure 28B:
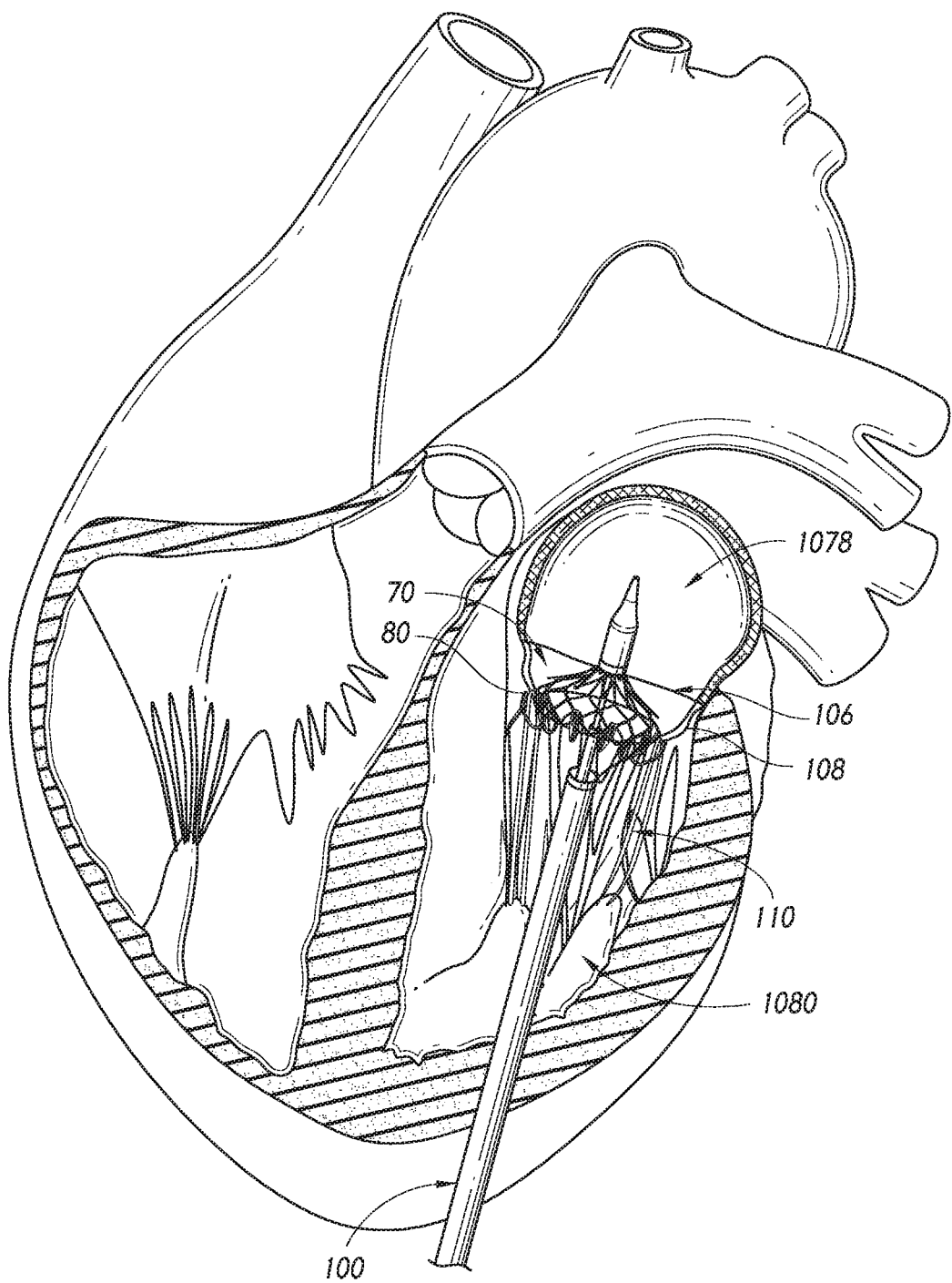

FIGS. 28A-B illustrate an alternate approach to releasing the prosthesis 70. As shown in FIG. 28A, the delivery system 100 can be translated into the left ventricle 1080 prior to release of the prosthesis 70. Thus, the ventricular end of the prosthesis 70, and thus the ventricular anchors 80, can be released and flipped partially, or fully within the left ventricle 1080 as shown in FIG. 28A upon proximal retraction of the outer elongate hollow member shaft 114. Accordingly, in some embodiments the anchors 80 can be released/flipped below the mitral annulus 106, and/or below the free edges of the leaflets 108. Further, the anchors 80 can be released above the papillary heads. Similar methodology as discussed above can then be used to properly position the prosthesis 70 and remove the delivery system 100 to deliver the prosthesis 70 into the position shown in FIG. 27F. In some embodiments, a waist of the prosthesis 70 can be even with the free edge of the leaflets 108 during release. In some embodiments, the ventricular anchors 80 may release in the ventricle 1080 without expansion of the prosthesis 70 body, such as discussed in detail above with respect to FIGS. 27A-B.

In any of the procedures described herein, a user can utilize rapid pacing at any step of the process. In some instances, this can facilitate positioning and/or anchoring of the prosthesis 1010 to native tissue.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z.

Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A delivery system for a replacement valve, the delivery system comprising:
   a tether configured to releasably hold a replacement valve;
   a torqueing manifold configured to retain a first end of the tether;
   an engagement pin configured to move from a locked position to an unlocked position, the engagement pin configured to releasably retain a second end of the tether;
   a manifold shaft having the torqueing manifold on a distal end of the manifold shaft, the torqueing manifold having at least one protrusion extending distally from a distal end of the torqueing manifold;
   a bearing rotatably retained within the torqueing manifold; and
   a pin lock shaft having a release plate located proximal of the bearing and located on a distal end of the pin lock shaft, wherein the pin lock shaft is configured to engage the engagement pin in the locked position and the unlocked position;
   wherein longitudinal translation of the engagement pin from the locked position to the unlocked position releases the second end of the tether and the replacement valve from the delivery system; and
   wherein rotational movement of the torqueing manifold with respect to the engagement pin is configured to crimp or uncrimp a portion of the replacement valve.

2. The delivery system of claim 1, wherein circumferential rotation of the manifold shaft with respect to the pin lock shaft is configured to crimp or uncrimp the portion of the replacement valve.

3. The delivery system of claim 1, wherein the engagement pin extends between the release plate and the bearing in the locked position, and wherein the second end of the tether is retained on the engagement pin between the release plate and the bearing in the locked position.

4. The delivery system of claim 1, wherein the manifold shaft is located within a lumen of the pin lock shaft, wherein the pin lock shaft is configured to longitudinally and rotationally translate with respect to the manifold shaft, and wherein proximal translation of the pin lock shaft releases the engagement pin from the bearing which releases the second end of the tether from the engagement pin.

5. The delivery system of claim 1, wherein the torqueing manifold comprises a plurality of distally extending protrusions extending around an outer circumference of the distal end of the torqueing manifold.

6. The delivery system of claim 1, wherein the engagement pin is generally L-shaped.

7. The delivery system of claim 1, further comprising the replacement valve, wherein the replacement valve is a replacement mitral valve.

8. The delivery system of claim 1, wherein the tether is configured to pass through an eyelet of the replacement valve.

9. A method of releasing a replacement valve from a delivery system, the method comprising:
   expanding the replacement valve from a compressed configuration to an expanded configuration, the replacement valve having a distal end and a proximal end, the replacement valve releasably attached to a manifold of the delivery system at a location distal to the replacement valve through at least one tether releasably retained on an engagement pin connected to the manifold in a locked position;
   rotating a manifold shaft located radially inwards of the replacement valve in a first direction with respect to a locking shaft, wherein the manifold shaft has the manifold on a distal end located distal to the replacement valve, wherein the at least one tether is connected to the manifold and the locking shaft, and wherein the manifold shaft is located within a lumen of the locking shaft, wherein the rotating the manifold shaft in the first direction loosens the at least one tether to uncrimp the distal end of the replacement valve; and
   proximally translating the engagement pin from the locked position to an unlocked position outside of the manifold, thereby releasing the at least one tether and the replacement valve.

10. The method of claim 9, wherein the expanding the replacement valve comprises:
    proximally translating an outer sheath to uncover the proximal end of the replacement valve; and
    distally translating a nosecone to uncover the distal end of the replacement valve.

11. The method of claim 9, further comprising rotating the manifold shaft in a second direction opposite the first direction with respect to the locking shaft to crimp the distal end of the replacement valve.

12. The method of claim 11, further comprising proximally translating a nosecone to cover the distal end of the replacement valve when the replacement valve is crimped.

13. The method of claim 9, further comprising proximally translating the locking shaft with respect to the manifold shaft which proximally translates the engagement pin to the unlocked position.

14. The method of claim 9, wherein the replacement valve is releasably attached to the delivery system via a plurality of tethers connected to a plurality of engagement pins.

15. The method of claim 9, wherein the replacement valve is a replacement mitral valve.

* * * * *